United States Patent
Hodgetts et al.

(10) Patent No.: US 10,787,433 B2
(45) Date of Patent: Sep. 29, 2020

(54) PYRIDAZINE DERIVATIVES AS EAAT2 ACTIVATORS

(71) Applicants: THE BRIGHAM AND WOMEN'S HOSPITAL, INC., Boston, MA (US); OHIO STATE UNIVERSITY, Columbus, OH (US)

(72) Inventors: Kevin Hodgetts, Framingham, MA (US); Chien-Liang Glenn Lin, Columbus, OH (US)

(73) Assignees: THE BRIGHAM AND WOMEN'S HOSPITAL, INC., Boston, MA (US); OHIO STATE UNIVERSITY, Columbus, OH (US)

( * ) Notice: Subject to any disclaimer, the term of this patent is extended or adjusted under 35 U.S.C. 154(b) by 0 days.

(21) Appl. No.: 16/070,393

(22) PCT Filed: Jan. 13, 2017

(86) PCT No.: PCT/US2017/013499
§ 371 (c)(1),
(2) Date: Jul. 16, 2018

(87) PCT Pub. No.: WO2017/123991
PCT Pub. Date: Jul. 20, 2017

(65) Prior Publication Data
US 2019/0040040 A1  Feb. 7, 2019

Related U.S. Application Data

(60) Provisional application No. 62/279,515, filed on Jan. 15, 2016.

(51) Int. Cl.
| | | |
|---|---|---|
| *C07D 401/14* | (2006.01) |
| *C07D 413/14* | (2006.01) |
| *C07D 401/04* | (2006.01) |
| *C07D 237/20* | (2006.01) |
| *C07D 417/14* | (2006.01) |
| *A61P 25/00* | (2006.01) |
| *A61P 35/00* | (2006.01) |
| *A61P 29/00* | (2006.01) |

(52) U.S. Cl.
CPC ............ *C07D 401/14* (2013.01); *A61P 25/00* (2018.01); *A61P 29/00* (2018.01); *A61P 35/00* (2018.01); *C07D 237/20* (2013.01); *C07D 401/04* (2013.01); *C07D 413/14* (2013.01); *C07D 417/14* (2013.01)

(58) Field of Classification Search
CPC .. C07D 237/20; C07D 401/04; C07D 401/14; C07D 413/14; C07D 417/14
See application file for complete search history.

(56) References Cited

U.S. PATENT DOCUMENTS

| 2010/0093703 A1* | 4/2010 | Wagner | C07D 209/04 514/218 |
| 2014/0303174 A1* | 10/2014 | Cuny | A61K 31/501 514/252.03 |
| 2015/0175555 A1 | 6/2015 | Watterson et al. | |

FOREIGN PATENT DOCUMENTS

| EP | 2772485 A1 | 9/2014 |
| WO | 2008070692 A2 | 6/2008 |
| WO | 2011133600 A1 | 10/2011 |
| WO | 2013019938 A1 | 2/2013 |
| WO | 2015193263 A1 | 12/2015 |

OTHER PUBLICATIONS

National Center for Biotechnology Information. PubChem Database. CID=52903538, https://pubchem.ncbi.nlm.nih.gov/compound/2-6-pyridin-2-ylpyridazin-3-yl_ oxyethanamine (accessed on Aug. 19, 2019).*
Chemical Abstracts Registry ( Apr. 2011).*
Partial Supplementary European Search Report issued for European Application No. 17739072, dated Jun. 3, 2019, 16 pages.
Xing, Xuechao, et al. "Structure-activity relationship study of pyridazine derivatives as glutamate transporter EAAT2 activators." Bioorganic & medicinal chemistry letters 21.19 (2011): 5774-5777.
Jones, R. Alan, and Alexander P. Whitmore. "The synthesis and chemical reactivity of 3-chloro-6-(2-pyrrolyl) pyridazine." Tetrahedron 54.33 (1998): 9519-9528.
Steck, Edgar A., R. Pauline Brundage, and Lynn T. Fletcher. "Pyridazines Part 8 Some 6-aryl-3-(basically-substituted) pyridazines." Journal of Heterocyclic Chemistry 12.5 (1975): 1009-1013.

(Continued)

*Primary Examiner* — Valerie Rodriguez-Garcia
(74) *Attorney, Agent, or Firm* — Meunier Carlin & Curfman LLC

(57) ABSTRACT

Pyradizine derivatives that activity the excitatory amino acid transporter 2 (EAAT2) of the formula:

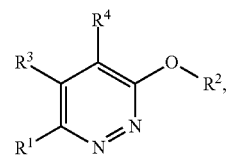

and methods of use thereof for treating or preventing diseases, disorders, and conditions with glutamate toxicity.

11 Claims, 1 Drawing Sheet

(56) References Cited

OTHER PUBLICATIONS

National Center for Biotechnology Information. PubChem Compound Database; CID=79423819, https://pubchem.ncbi.nlm.nih.gov/compound/79423819 (accessed Jul. 12, 2018). 10 pages.
U.S. Patent and Trademark Office. International Search Report and Written Opinion. Application No. PCT/US2017/013499, dated May 25, 2017. 10 pages.
Ayers-Ringler, et al., "Role of astrocytic glutamate transporter in alcohol use disorder", World J. Psychiatry. Mar. 22, 2016;6(1):31-42.
Bacigaluppi, et al., "Neural Stem Cell Transplantation Induces Stroke Recovery by Upregulating Glutamate Transporter GLT-1 in Astrocytes", J. Neurosci. Oct. 12, 2016;36(41):10529-10544.
Chen et al., Presynaptic glutamatergic dysfunction in bipolar disorder, Biol. Pshychiatry, 2010, 67(11): 1007-1009.
Chizh et al., "Novel approaches to targeting glutamate receptors for the treatment of chronic pain: review article", Amino Acids 2002, 23(1-3):169-76.
Cisneros, et al., "HIV-1, Methamphetamine and Astrocyte Glutamate Regulation: Combined Excitotoxic Implications for Neuro-AIDS", Curr. HIV Res. Jul. 2012;10(5):392-406.
De Bartolomeis, et al., "Targeting glutamate system for novel antipsychotic approaches: relevance for residual psychotic symptoms and treatment resistant schizophrenia.", Eur J Pharmacol. May 5, 2012;682(1-3):1-11.
Descalzi et al., "Presynaptic and Postsynaptic Cortical Mechanisms of Chronic Pain", Mol Neurobiol. 2009, 40(3):253-9.
Ende, et la., "Impulsivity and Aggression in Female BPD and ADHD Patients: Association with ACC Glutamate and GABA Concentrations.", Neuropsychopharmacology. Jan. 2016;41(2):410-8.
Gegelashvili, et al., "High-affinity glutamate transporters in chronic pain: an emerging therapeutic target", J. Neurochem. Dec. 2014;131(6):712-30.
Ghanizadeh, et al., "Beta-Lactam Antibiotics as a Possible Novel Therapy for Managing Epilepsy and Autism, A Case Report and Review of Literature", Iran J Child Neurol. 2015 Winter;9(1):99-102.
Guardia, et al., "GABAergic and glutamatergic modulation in binge eating: therapeutic approach", Curr. Pharm. Des. 2011;17(14):1396-409.
Guo et al., "Increased expression of the glial glutamate transporter EAAT2 modulates excitotoxicity and delays the onset but not the outcome of ALS in mice", Hum. Mol. Genet. 2003, 12, 2519.
Hazell, "Excitotoxic mechanisms in stroke: An update of concepts and treatment strategies", Neurochem. Int. 2007 50, 941.
Hu et al., "Glutamate receptors in preclinical research on Alzheimer's disease: Update on recent advances." Pharmacol Biochem Behav. Apr. 22, 2011 [Epub ahead of print, doi:10.1016/j.pbb.2011.04.013.
Berge, Stephen M., Lyle D. Bighley, and Donald C. Monkhouse. "Pharmaceutical salts." Journal of pharmaceutical sciences 66.1 (1977): 1-19.
Kaul and Lipton, "Mechanisms of Neuronal Injury and Death in HIV-1 Associated Dementia", Curr HIV Res. 4(3):307-18 (2006).
Kim et al., "Role of excitatory amino acid transporter-2 (EAAT2) and glutamate in neurodegeneration: opportunities for developing novel therapeutics.", J Cell Physiol. 226(10):2484-93 (2011).
Kong, et al., "Small-molecule activator of glutamate transporter EAAT2 translation provides neuroprotection", J. Clin. Invest. Mar. 2014;124(3):1255-67.
Lapidus, et al., "Novel glutamatergic drugs for the treatment of mood disorders.", Neuropsychiatr Dis Treat. 2013, 9:1101-12.
Larsson, "Ionotropic Glutamate Receptors in Spinal Nociceptive Processing", Mol Neurobiol. 2009, 40(3):260-88.
Lin et al., "Increased glial glutamate transporter EAAT2 expression reduces visceral nociceptive response in mice", Am. J. Physiol. Gastrointest Liver Physiol. 2009, 296, G129-G134.

Mark et al., "Pictorial Review of Glutamate Excitotoxicity: Fundamental Concepts for Neuroimaging", American Journal of Neuroradiology 22:1813-1824 (2001).
Melzer, et al., "A β-Lactam Antibiotic Dampens Excitotoxic Inflammatory CNS Damage in a Mouse Model of Multiple Sclerosis", PLoS One. Sep. 5, 2008;3(9):e3149.
Miller, et al., "Up-regulation of GLT1 reverses the deficit in cortically evoked striatal ascorbate efflux in the R6/2 mouse model of Huntington's disease", J. Neurochem. May 2012;121(4):629-38.
Mineur, et al., "Antidepressant-like effects of ceftriaxone in male C57BL/6J mice.", Biol Psychiatry. Jan. 15, 2007;61(2):250-2.
Myers et al., "Glutamate Receptors in Extinction and Extinction-Based Therapies for Psychiatric Illness", Neuropsychopharmacology. 36(1):274-93 (2011).
Nakagawa, et al., "SLC1 glutamate transporters and diseases: psychiatric diseases and pathological pain.", Curr Mol Pharmacol. Jul. 2013;6(2):66-73.
Nakagawa, et al., "Spinal Astrocytes as Therapeutic Targets for Pathological Pain", J. Pharmacol. Sci. 2010;114(4):347-53.
Nakatsu et al., "Glutamate Excitotoxicity Is Involved in Cell Death Caused by Tributyltin in Cultured Rat Cortical Neurons", Toxicol. Sci. (Jan. 2006) 89 (1): 235-242.
Nanitsos, et al., "Glutamatergic hypothesis of schizophrenia: involvement of Na+/K+-dependent glutamate transport.", J Biomed Sci. Dec. 2005;12(6):975-84.
Noch and Khalili, "Molecular mechanisms of necrosis in glioblastoma. The role of glutamate excitotoxicity", Cancer Biol Ther. 8(19):1791-7 (2009).
Olney, John W. "Role of excitotoxins in developmental neuropathology." Apmis. Supplementum 40 (1993): 103-112.
Owen, "Glutamatergic approaches in major depressive disorder: focus on ketamine, memantine and riluzole.", Drugs today, 2012, 48(7):469-78.
Pittenger, et al., "Glutamate abnormalities in obsessive compulsive disorder: neurobiology, pathophysiology, and treatment.", Pharmacol. Ther. Dec. 2011; 132(3): 314-332.
Jollant, Fabrice, et al. "Spectroscopy markers of suicidal risk and mental pain in depressed patients." Progress in neuro-psychopharmacology and biological psychiatry 73 (2017): 64-71.
Prost et al., "Detection of glutamate/glutamine resonances by 1H magnetic resonance spectroscopy at 0.5 tesla", Magn Reson Med 1997;37:615-618.
Reissner and Kalivas, "Using glutamate homeostasis as a target for treating addictive disorders.", Behav Pharmacol. Sep. 2010;21(5-6):514-22 (2010).
Roberts-Wolfe, et al., "Glutamate Transporter GLT-1 as a Therapeutic Target for Substance Use Disorders", CNS Neurol. Disord. Drug. Targets. 2015;14(6):745-56.
Sattler, et al., "Targeting an old mechanism in a new disease-protection of glutamatergic dysfunction in depression.", Biol Psychiatry. Jan. 15, 2007;61(2):137-8.
Scofield, et al., "Astrocytic dysfunction and addiction: consequences of impaired glutamate homeostasis.", Neuroscientist. Dec. 2014;20(6):610-22.
Seifert et al., "Astrocyte dysfunction in epilepsy", Brain. Res. Rev. 2010, 63, 212-221.
Sheldon and Robinson, "The Role of Glutamate Transporters in Neurodegenerative Diseases and Potential Opportunities for Intervention", Neurochem. Int. 2007, 51, 333.
Stephens, "Glutamate transporter activators as anti-nociceptive agents", Eurasian J Med. Dec. 2011;43(3):182-5.
Takahashi, et al., "Restored glial glutamate transporter EAAT2 function as a potential therapeutic approach for Alzheimer's disease", J. Exp. Med. Mar. 9, 215;212(3):319-32.
Tian et al., "Increased expression of cholesterol 24S-hydroxylase results in disruption of glial glutamate transporter EAAT2 association with lipid rafts: a potential role in Alzheimer's disease", J. Neurochem. 2010, 113, 978.
Tian et al., "Translational control of glial glutamate transporter EAAT2 expression", J. Biol. Chem. 2007, 282, 1727.
Tiwari, et al., "Impact of histamine receptors H1 and H3 polymorphisms on antipsychotic-induced weight gain.", World J. Biol. Psychiatry. Dec. 15, 2016:1-9.

(56) References Cited

OTHER PUBLICATIONS

Torres-Altoro, et al., "Organophosphates dysregulate dopamine signaling, glutamatergic neurotransmission, and induce neuronal injury markers in striatum.", J. Neurochem. Oct. 2011;119(2):303-13.

Tzschentke, "Glutamatergic mechanisms in different disease states: overview and therapeutical implications—an introduction", Amino Acids 23(1-3):147-52 (2002).

Vargas, "Chronic migraine: Current pathophysiologic concepts as targets for treatment", Curr Pain Headache Rep. 13(1):64-6 (2009).

Wang and Qin, "Molecular and cellular mechanisms of excitotoxic neuronal death", Apoptosis. 15(11):1382-402 (2010).

Wilen, S.H., et al., "Strategies in optical resolutions", Tetrahedron 1977, 33:2725-2736.

Yi, et al., "Excitotoxic mechanisms and the role of astrocytic glutamate transporters in traumatic brain injury", Neurochem. Int. Apr. 2006;48(5):394-403.

Yogeeswari et al., "Current approaches with the glutamatergic system as targets in the treatment of neuropathic pain", Expert Opin Ther Targets. 13(8):925-43 (2009).

Yousuf, et al., "The Role of Regulatory Transporters in Neuropathic Pain", Adv. Pharmacol. 2016;75:245-71.

Zhang, et al., Recent Advance in the Relationship between Excitatory Amino Acid Transporters and Parkinson's Disease, Neural. Plast. 2016; Article ID: 8941327.

Zumkehr, J., et al., Ceftriaxone ameliorates tau pathology and cognitive decline via restoration of glial glutamate transporter in a mouse model of Alzheimer's disease. Neurobiol Aging, 2015. 36(7): p. 2260-71.

Extended Search Report issued for Application No. 17739072, dated Sep. 5, 2019.

\* cited by examiner

PYRIDAZINE DERIVATIVES AS EAAT2 ACTIVATORS

CROSS-REFERENCE TO RELATED APPLICATIONS

This application claims the benefit of U.S. Provisional Application Ser. No. 62/279,515, filed Jan. 15, 2016, the disclosure of which is incorporated herein by reference in its entirety.

STATEMENT OF GOVERNMENT SUPPORT

This invention was made with government support under grant numbers NS064275 and NS049339 awarded by the National Institutes of Health. The government has certain rights in the invention.

TECHNICAL FIELD

This present description relates to pyridazine derivatives that activate the excitatory amino acid transporter 2 (EAAT2), and methods of use thereof for treating or preventing diseases, disorders, and conditions associated with glutamate excitotoxicity.

BACKGROUND

Glutamate is a major neurotransmitter in the mammalian central nervous system (CNS) and essential for normal brain function including cognition, memory, and learning. However, the extracellular concentration of glutamate must remain below excitotoxic levels (~1 uM) to avoid overstimulation of glutamate receptors, leading to neuronal damage or death (Sheldon and Robinson, Neurochem. Int. 2007, 51, 333). Excitotoxicity has been associated with multiple acute neurological conditions such as ischemic stroke, epilepsy, and trauma, chronic adult-onset neurodegenerative disorders such as Alzheimer's disease and amyotrophic lateral sclerosis (ALS) (Guo et al., Hum. Mol. Genet. 2003, 12, 2519; Tian et al., J. Biol. Chem. 2007, 282, 1727; Hazell, Neurochem. Int. 2007 50, 941; Seifert et al., Brain. Res. Rev. 2010, 63, 212; Tian et al., J. Neurochem. 2010, 113, 978), and depression. One potential approach to preventing excitotoxicity is to enhance glutamate reuptake. EAAT2 is the major glutamate transporter and functions to remove glutamate from synapses (Lin et al., Am. J. Physiol. Gastrointest Liver Physiol. 2009, 296, 129). An increase in EAAT2 protein expression and function can provide a means to prevent insufficient glutamate reuptake and consequently reduce neuronal damage.

SUMMARY

The present application provides, inter alia, a compound of Formula (I):

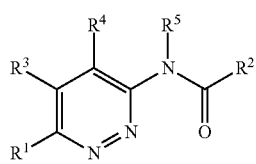

(I)

or a pharmaceutically acceptable salt thereof, wherein:

$R^1$ is selected from the group consisting of 6-10 membered aryl and 5-10 membered heteroaryl, each of which is optionally substituted by 1, 2, 3, or 4 independently selected $R^A$ groups;

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^3$, $R^4$, and $R^5$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is a 6-10 membered aryl which is optionally substituted by 1, 2, 3, or 4 independently selected $R^A$ groups. In some embodiments, $R^1$ is phenyl which is optionally substituted by 1, 2, 3, or 4 independently selected $R^A$ groups. In some embodiments, each $R^A$ is independently selected from the group consisting of halo, $C_{1-6}$ alkyl, and $OR^a$. In some embodiments, each $R^A$ is independently selected from the group consisting of $CH_3$, F, OH, and $OCH_3$. In some embodiments, $R^1$ is a 5-10 membered heteroaryl which is optionally substituted by 1, 2, 3, or 4 independently selected $R^A$ groups. In some embodiments, $R^1$ is pyridyl which is optionally substituted by 1, 2, 3, or 4 independently selected $R^A$ groups.

In some embodiments, wherein $R^2$ is a 6-10 membered aryl which is optionally substituted by 1, 2, 3, or 4 independently selected $R^B$ groups. In some embodiments, $R^2$ is phenyl which is optionally substituted by 1, 2, 3, or 4 independently selected $R^B$ groups. In some embodiments, each $R^B$ is independently selected from the group consisting of halo, $C_{1-6}$ alkyl, and $OR^a$. In some embodiments, each $R^B$ is independently selected from the group consisting of F, Cl, OH, and OCH$_3$. In some embodiments, R$^2$ is a 5-10 membered heteroaryl which is optionally substituted by 1, 2, 3, or 4 independently selected R$^B$ groups. In some embodiments, R$^2$ is selected from the group consisting of pyridyl, pyridazinyl, pyrimidinyl, thiazolyl, and imidazolyl, each of which is optionally substituted by 1, 2, 3, or 4 independently selected R$^B$ groups. In some embodiments, each R$^B$ is independently selected from the group consisting of halo and C$_{1-6}$ alkyl. In some embodiments, each R$^B$ is independently selected from the group consisting of F and CH$_3$. In some embodiments, R$^2$ is a 5-10 membered heterocyclyl which is optionally substituted by 1, 2, 3, or 4 independently selected R$^B$ groups. In some embodiments, R$^2$ is piperidinyl, which is optionally substituted by 1, 2, 3, or 4 independently selected R$^B$ groups.

In some embodiments, R$^3$ and R$^4$ are H.

In some embodiments, R$^5$ is H.

In some embodiments, the compound of Formula (I) is a compound of Formula (Ia):

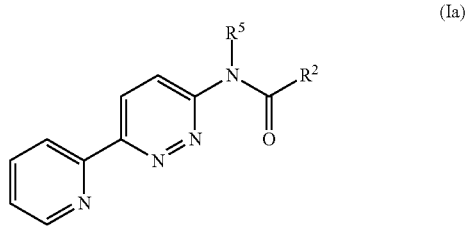

(Ia)

or a pharmaceutically acceptable salt thereof, wherein:

R$^2$ is selected from the group consisting of 6-10 membered aryl, 5-10 membered heteroaryl, 4-10 membered heterocycloalkyl, each of which is optionally substituted by 1, 2, 3, or 4 independently selected R$^B$ groups;

R$^5$ is selected from H and C$_{1-6}$ alkyl;

each R$^B$ is independently selected from halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^6$ groups;

each R$^a$, R$^b$, R$^c$, and R$^d$ is independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl are each optionally substituted with 1, 2, 3, or 4 independently selected R$^6$ groups;

each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl; and each R$^6$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO-alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$alkyl)aminosulfonylamino, aminocarbonylamino, C$_{1-6}$ alkylaminocarbonylamino, and di(C$_{1-6}$ alkyl)aminocarbonylamino.

In some embodiments, R$^2$ is a 6-10 membered aryl which is optionally substituted by 1, 2, 3, or 4 independently selected R$^B$ groups. In some embodiments, R$^2$ is phenyl which is optionally substituted by 1, 2, 3, or 4 independently selected R$^B$ groups. In some embodiments, each R$^B$ is independently selected from the group consisting of halo, C$_{1-6}$ alkyl, and OR$^a$. In some embodiments, each R$^B$ is independently selected from the group consisting of F, Cl, OH, and OCH$_3$. In some embodiments, R$^2$ is a 5-10 membered heteroaryl which is optionally substituted by 1, 2, 3, or 4 independently selected R$^B$ groups. In some embodiments, R$^2$ is selected from the group consisting of pyridyl, pyridazinyl, pyrimidinyl, thiazolyl, and imidazolyl, each of which is optionally substituted by 1, 2, 3, or 4 independently selected R$^B$ groups. In some embodiments, each R$^B$ is independently selected from the group consisting of halo and C$_{1-6}$ alkyl. In some embodiments, each R$^B$ is independently selected from the group consisting of F and CH$_3$. In some embodiments, R$^2$ is a 5-10 membered heterocyclyl which is optionally substituted by 1, 2, 3, or 4 independently selected R$^B$ groups. In some embodiments, R$^2$ is piperidinyl, which is optionally substituted by 1, 2, 3, or 4 independently selected R$^B$ groups.

In some embodiments, the compound of Formula (I) is selected from the group consisting of:

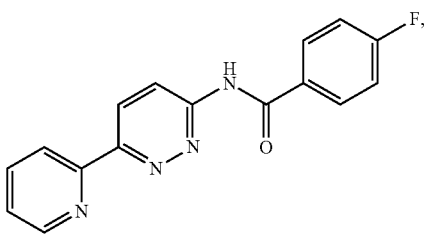

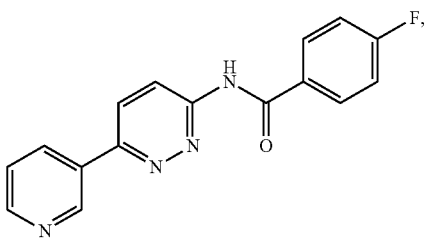

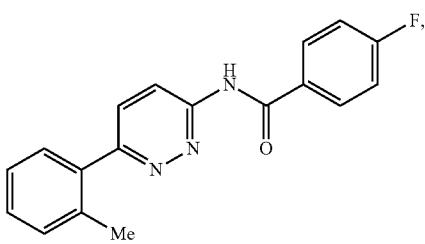

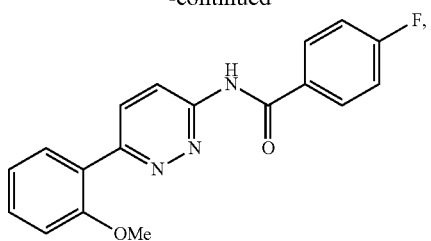
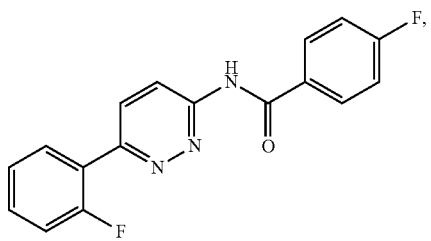
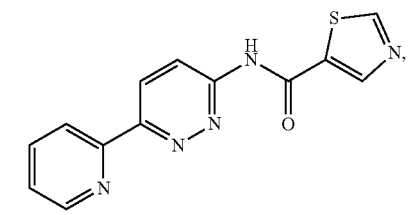
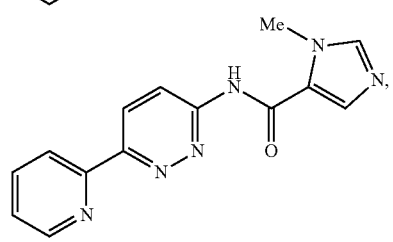
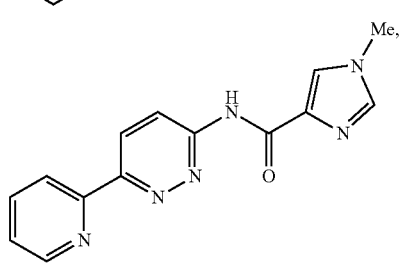
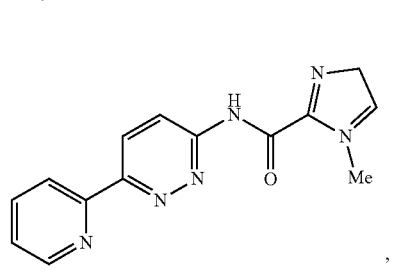
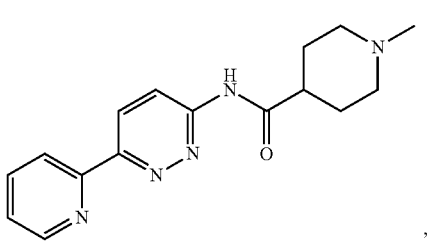
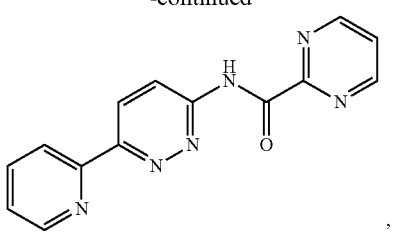
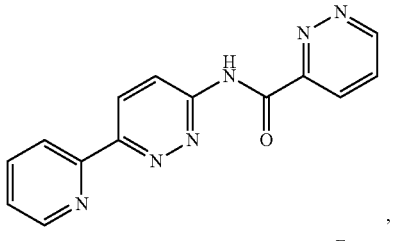
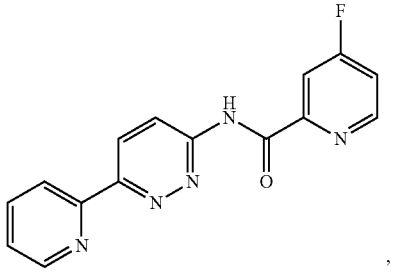
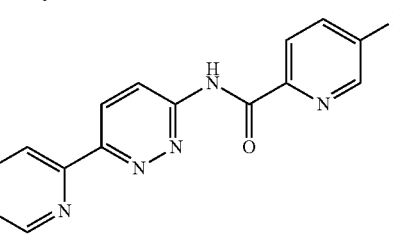
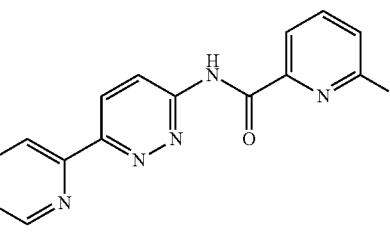
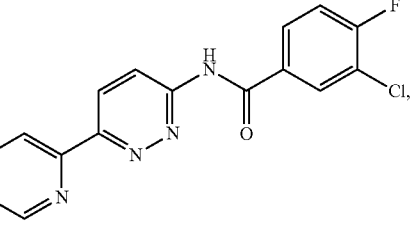
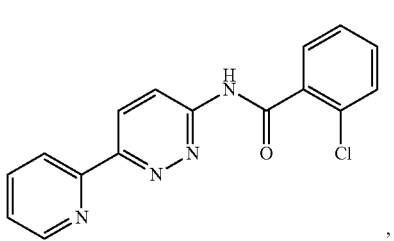

-continued

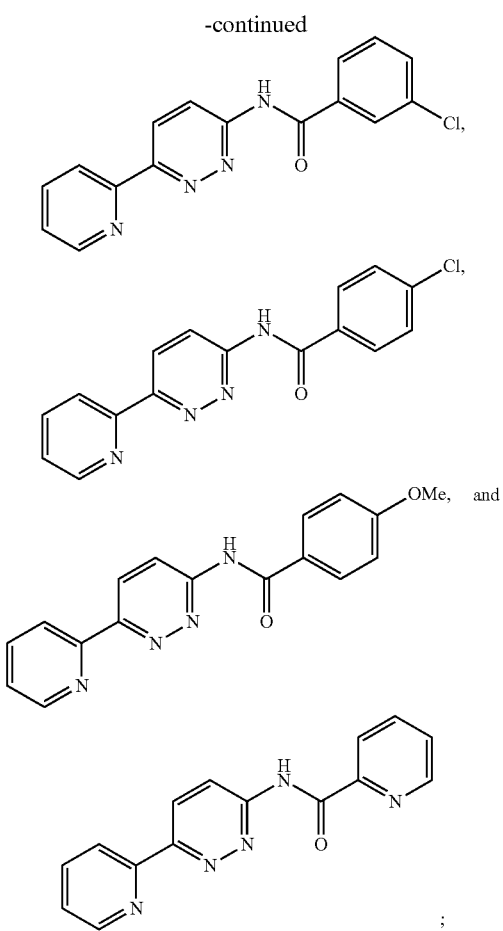

or a pharmaceutically acceptable salt thereof.

The present application further provides a compound of Formula (II):

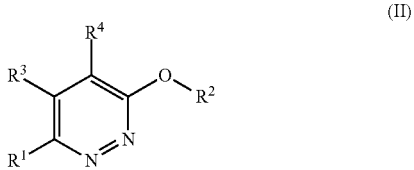

or a pharmaceutically acceptable salt thereof, wherein:

R$^1$ is selected from the group consisting of 6-10 membered aryl and 5-10 membered heteroaryl, each of which is optionally substituted by 1, 2, 3, or 4 independently selected R$^A$ groups;

R$^2$ is —(CHR$^E$)$_n$R$^5$;

R$^5$ is selected from the group consisting of NR$^C$R$^D$, C(O)NR$^C$R$^D$, C(O)OR$^C$, and 5-10 membered heteroaryl, wherein the 5-10 membered heteroaryl is optionally substituted by 1, 2, 3, or 4 independently selected R$^B$ groups;

R$^E$ is H or C$_{1-6}$ alkyl, wherein said C$_{1-6}$ alkyl is optionally substituted by 1, 2, 3, or 4 independently selected R$^6$ groups;

R$^3$ and R$^4$ are independently selected from H and C$_{1-6}$ alkyl;

each R$^A$ and R$^B$ is independently selected from halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected R$^6$ groups;

R$^C$ and R$^D$ are independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, and 5-10 membered heteroaryl-C$_{1-4}$ alkylene are each optionally substituted with 1, 2, 3, or 4 independently selected R$^6$ groups; or alternatively, any R$^C$ and R$^D$ attached to the same N atom, together with the N atom to which they are attached, form a 4-6 membered heterocycloalkyl group or a 5-6 membered heteroaryl group, each optionally substituted with 1, 2, or 3 independently selected R$^6$ groups;

each R$^a$, R$^b$, R$^c$, and R$^d$ is independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl are each optionally substituted with 1, 2, 3, or 4 independently selected R$^6$ groups;

each R$^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl;

each R$^6$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$ alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$ alkyl)aminosulfonyl, aminosulfonylamino, C$_{1-6}$ alkylaminosulfonylamino, di(C$_{1-6}$ alkyl)aminosulfonylamino, aminocarbonylamino, C$_{1-6}$ alkylaminocarbonylamino, and di(C$_{1-6}$ alkyl)aminocarbonylamino; and n is 1, 2, 3, 4, or 5.

In some embodiments, R$^1$ is a 5-10 membered heteroaryl which is optionally substituted by 1, 2, 3, or 4 independently selected R$^A$ groups. In some embodiments, R$^1$ is pyridyl which is optionally substituted by 1, 2, 3, or 4 independently selected R$^A$ groups.

In some embodiments, R$^5$ is a 5-10 membered heteroaryl which is optionally substituted by 1, 2, 3, or 4 independently selected R$^B$ groups. In some embodiments, R$^5$ is selected from oxazolyl and pyridyl, each of which is optionally substituted by 1, 2, 3, or 4 independently selected R$^B$ groups.

In some embodiments, R$^5$ is NR$^C$R$^D$, wherein R$^C$ and R$^D$ independently selected from H and C$_{1-6}$ alkyl. In some embodiments, R$^C$ and R$^D$ are CH$_3$. In some embodiments, $R^5$ is $C(O)NR^CR^D$, wherein $R^C$ and $R^D$ are independently selected from H, $C_{1-6}$ alkyl, and 6-10 membered aryl optionally substituted with 1, 2, 3, or 4 independently selected $R^6$ groups; or alternatively, $R^C$ and $R^D$ attached to the same N atom, together with the N atom to which they are attached, form a 4-6 membered heterocycloalkyl group optionally substituted with 1, 2, or 3 independently selected $R^6$ groups. In some embodiments, $R^C$ and $R^D$ are independently selected from H and $C_{1-6}$ alkyl. In some embodiments, $R^C$ and $R^D$ are independently selected from H, $C_{1-6}$ alkyl, and phenyl optionally substituted with $C_{1-6}$ alkyl. In some embodiments, $R^C$ and $R^D$ attached to the same N atom, together with the N atom to which they are attached, form a 4-6 membered heterocycloalkyl group. In some embodiments, $R^5$ is $C(O)OR^C$, wherein $R^C$ is H or $C_{1-6}$ alkyl.

In some embodiments, $R^3$ and $R^4$ are H.

In some embodiments, n is 1 or 2.

In some embodiments, the compound of Formula (II) is a compound of Formula (IIa):

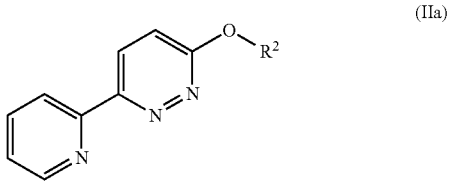

(IIa)

or a pharmaceutically acceptable salt thereof, wherein:
$R^2$ is $-(CHR^E)_nR^5$;
$R^5$ is selected from the group consisting of $NR^CR^D$, $C(O)NR^CR^D$, $C(O)OR^C$, and 5-10 membered heteroaryl, wherein the 5-10 membered heteroaryl is optionally substituted by 1, 2, 3, or 4 independently selected $R^B$ groups;
$R^E$ is H or $C_{1-6}$ alkyl, wherein said $C_{1-6}$ alkyl is optionally substituted by 1, 2, 3, or 4 independently selected $R^6$ groups;
each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^CR^d$, $C(O)OR^a$, $OC(O)R^b$, $OC(O)NR^CR^d$, $NR^CR^d$, $NR^COR^d$, $NR^CC(O)R^b$, $NR^CC(O)OR^a$, $NR^CC(O)NR^CR^d$, $C(=NR^e)R^b$, $C(=NR^e)NR^CR^d$, $NR^CC(=NR^e)NR^CR^d$, $NR^CS(O)R^b$, $NR^CS(O)_2R^b$, $NR^CS(O)_2NR^CR^d$, $S(O)R^b$, $S(O)NR^CR^d$, $S(O)_2R^b$, and $S(O)_2NR^CR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;
$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or
alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;
each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;
each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and
n is 1, 2, 3, 4, or 5.

In some embodiments, $R^5$ is a 5-10 membered heteroaryl which is optionally substituted by 1, 2, 3, or 4 independently selected $R^B$ groups. In some embodiments, $R^5$ is selected from oxazolyl and pyridyl, each of which is optionally substituted by 1, 2, 3, or 4 independently selected $R^B$ groups. In some embodiments, $R^5$ is $NR^CR^D$, wherein $R^C$ and $R^D$ independently selected from H and $C_{1-6}$ alkyl. In some embodiments, $R^C$ and $R^D$ are $CH_3$. In some embodiments, $R^5$ is $C(O)NR^CR^D$, wherein $R^C$ and $R^D$ are independently selected from H, $C_{1-6}$ alkyl, and 6-10 membered aryl optionally substituted with 1, 2, 3, or 4 independently selected $R^6$ groups; or alternatively, $R^C$ and $R^D$ attached to the same N atom, together with the N atom to which they are attached, form a 4-6 membered heterocycloalkyl group optionally substituted with 1, 2, or 3 independently selected $R^6$ groups. In some embodiments, $R^C$ and $R^D$ are independently selected from H and $C_{1-6}$ alkyl. In some embodiments, $R^C$ and $R^D$ are independently selected from H, $C_{1-6}$ alkyl, and phenyl optionally substituted with $C_{1-6}$ alkyl. In some embodiments, $R^C$ and $R^D$ attached to the same N atom, together with the N atom to which they are attached, form a 4-6 membered heterocycloalkyl group. In some embodiments, $R^5$ is $C(O)OR^C$, wherein $R^C$ is H or $C_{1-6}$ alkyl.

In some embodiments, n is 1 or 2.

In some embodiments, the compound of Formula (II) is selected from the group consisting of:

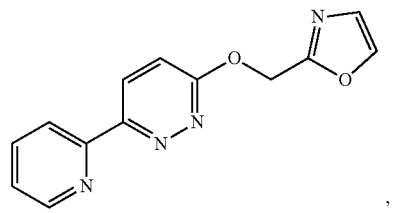

,

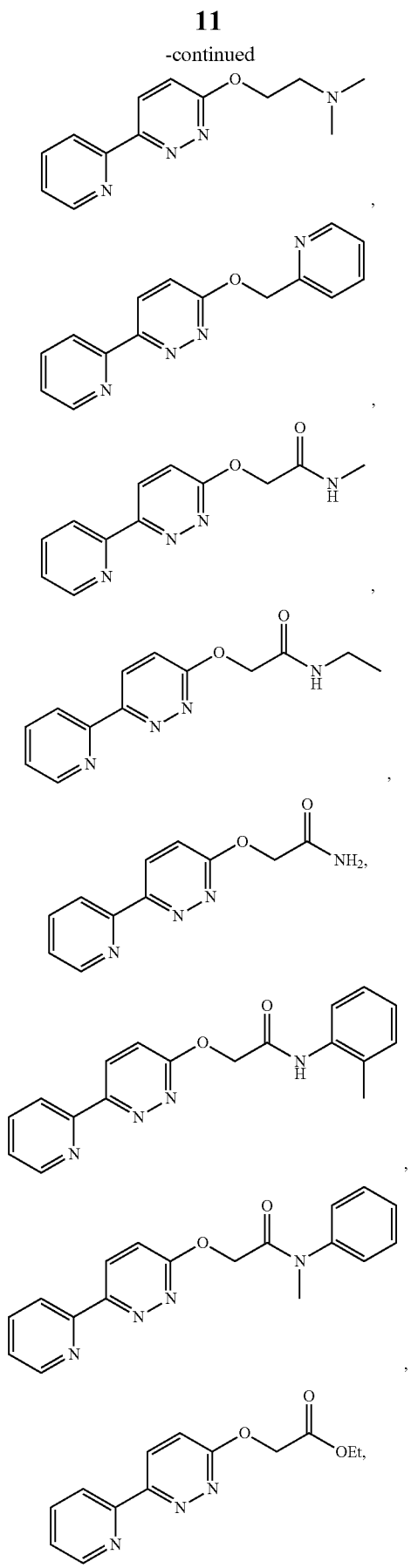

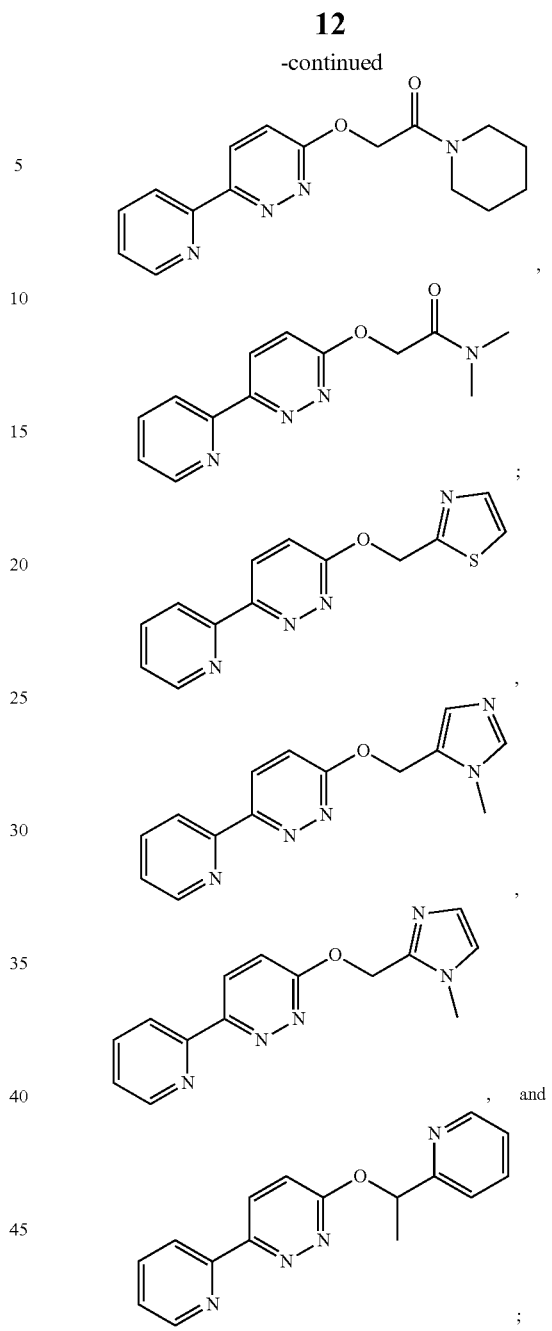

or a pharmaceutically acceptable salt thereof.

The present application further provides a compound of Formula (III):

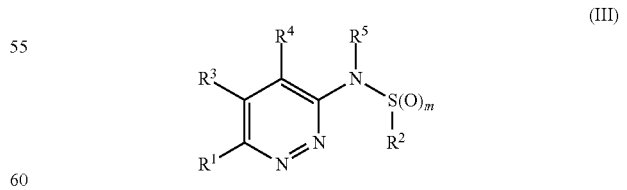

(III)

or a pharmaceutically acceptable salt thereof, wherein:

$R^1$ is selected from the group consisting of 6-10 membered aryl and 5-10 membered heteroaryl, each of which is optionally substituted by 1, 2, 3, or 4 independently selected $R^A$ groups;

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^3$, $R^4$, and $R^5$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and m is 1 or 2.

In some embodiments, $R^1$ is a 5-10 membered heteroaryl which is optionally substituted by 1, 2, 3, or 4 independently selected $R^A$ groups. In some embodiments, $R^1$ is pyridyl which is optionally substituted by 1, 2, 3, or 4 independently selected $R^A$ groups. In some embodiments, $R^1$ is unsubstituted pyridyl.

In some embodiments, $R^2$ is a 6-10 membered aryl which is optionally substituted by 1, 2, 3, or 4 independently selected $R^B$ groups. In some embodiments, $R^2$ is phenyl which is optionally substituted by 1, 2, 3, or 4 independently selected $R^B$ groups.

In some embodiments, each $R^B$ is an independently selected halo group. In some embodiments, each $R^B$ is F.

In some embodiments, $R^3$ and $R^4$ are H.

In some embodiments, $R^5$ is H.

In some embodiments, m is 2.

In some embodiments, the compound of Formula (III) is a compound of Formula (IIIa):

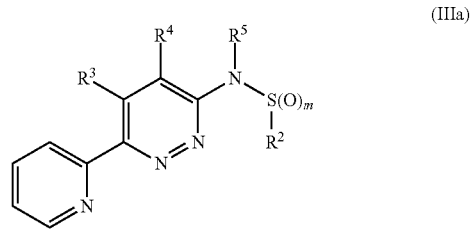

(IIIa)

or a pharmaceutically acceptable salt thereof, wherein:

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^5$ is selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and m is 1 or 2.

In some embodiments, $R^2$ is a 6-10 membered aryl which is optionally substituted by 1, 2, 3, or 4 independently selected $R^B$ groups. In some embodiments, $R^2$ is phenyl which is optionally substituted by 1, 2, 3, or 4 independently selected $R^B$ groups.

In some embodiments, each $R^B$ is an independently selected halo group. In some embodiments, each $R^B$ is F.

In some embodiments, m is 2.

In some embodiments, the compound of Formula (III) is selected from the group consisting of:

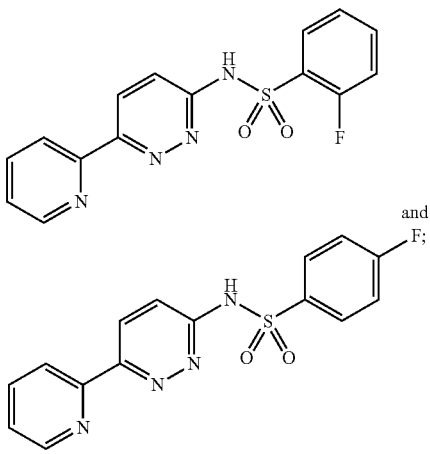

and

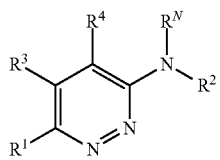

or a pharmaceutically acceptable salt thereof.

The present application further provides a compound of Formula (IV):

(IV)

or a pharmaceutically acceptable salt thereof, wherein:

$R^N$ is selected from the group consisting of H, $C_{1-6}$ alkyl, and $C(O)R^{N1}$;

$R^{N1}$ is a $C_{6-10}$ aryl which is optionally substituted by 1, 2, 3, or 4 independently selected halo groups;

$R^1$ is selected from the group consisting of 6-10 membered aryl and 5-10 membered heteroaryl, each of which is optionally substituted by 1, 2, 3, or 4 independently selected $R^A$ groups;

$R^2$ is —(CHR$^E$)$_n$R$^5$;

$R^5$ is selected from the group consisting of NR$^C$R$^D$, C(O)NR$^C$R$^D$, C(O)OR$^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, NO$_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^N$ is selected from the group consisting of H, $C_{1-6}$ alkyl, and $C(O)R^{N1}$, wherein $R^{N1}$ is a phenyl ring which is optionally substituted by 1, 2, 3, or 4 independently selected halo groups.

In some embodiments, $R^N$ is selected from the group consisting of H, $C_{1-3}$ alkyl, and $C(O)R^{N1}$, wherein $R^{N1}$ is a phenyl ring which is optionally substituted by 1 or 2 fluoro groups.

In some embodiments, $R^N$ is selected from the group consisting of H, methyl, C(O)phenyl, and C(O)(4-fluorophenyl.

In some embodiments, $R^1$ is an unsubstituted 5-6 membered heteroaryl.

In some embodiments, $R^1$ is pyridyl.

In some embodiments, $R^2$ is —(CH$_2$)$_n$R$^5$ and n is 0, 1, 2, or 3.

In some embodiments, $R^3$ is H.

In some embodiments, $R^4$ is H.

In some embodiments, $R^5$ is selected from the group consisting of NR$^C$R$^D$, $C_{6-10}$ aryl, and 5-10 membered heteroaryl, wherein the $C_{6-10}$ aryl and 5-10 membered heteroaryl are each optionally substituted by 1, 2, 3, or 4 independently selected $R^B$ groups. In some embodiments, $R^5$ is selected from the group consisting of $NR^CR^D$, unsubstituted phenyl, and unsubstituted 5-6 membered heteroaryl, wherein $R^C$ and $R^D$ are each an independently selected $C_{1-4}$ alkyl group.

In some embodiments, the compound of Formula (IV) is a compound of Formula (IVa):

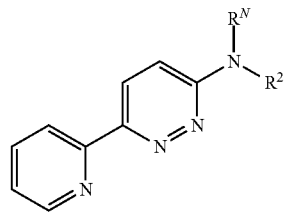

(IVa)

or a pharmaceutically acceptable salt thereof.

In some embodiments, the compound of Formula (IV) is selected from the group consisting of:

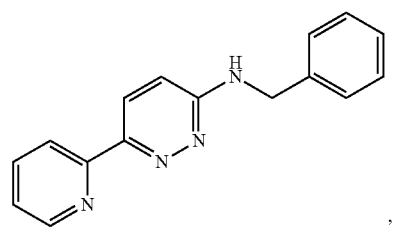

,

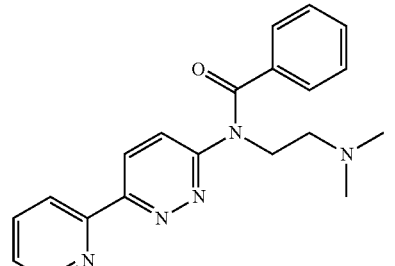

,

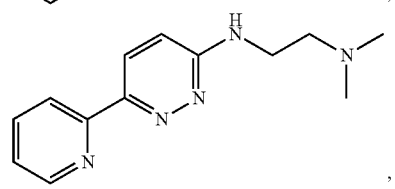

,

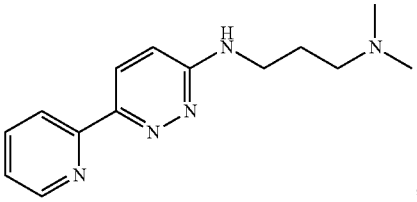

,

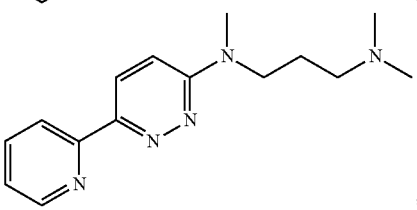

,

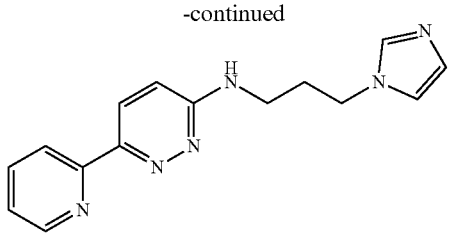

,

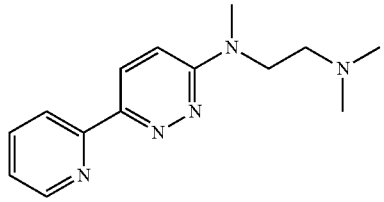

,

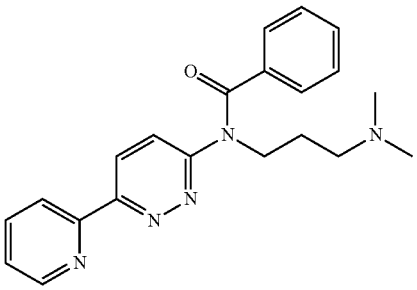

, and

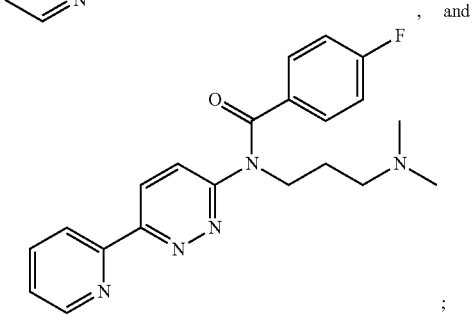

;

or a pharmaceutically acceptable salt thereof.

The present application further provides a pharmaceutical composition comprising a compound provided herein, or a pharmaceutically acceptable salt thereof, and a pharmaceutically acceptable excipient.

The present application further provides a method for treating or preventing glutamate excitotoxicity in a subject in need thereof, the method comprising administering to the subject an effective amount of a compound provided herein, or a pharmaceutically acceptable salt thereof.

The present application further provides a method for increasing EAAT2 protein expression in a cell or a subject in need thereof, the method comprising contacting the cell or administering to the subject an effective amount of a compound provided herein, or a pharmaceutically acceptable salt thereof.

The present application further provides a method for activating the NRF2 pathway in a cell or a subject in need thereof, the method comprising contacting the cell or administering to the subject an effective amount of a compound provided herein, or a pharmaceutically acceptable salt thereof.

The present application further provides a method for treating a disease or disorder selected from the group consisting of ischemic stroke, epilepsy, or a trauma, including blunt trauma, an abrasion, an avulsion, an incision, a laceration, a puncture, a penetration, a surgical trauma, iatrogenic trauma, a spinal cord injury, a traumatic brain injury, or any combination thereof; a chronic neurodegenerative disorder, including mild cognitive impairment, Parkinson's disease, Alzheimer's disease, multiple sclerosis, mesial temporal sclerosis, Huntington's disease, AIDS dementia complex, or amyotrophic lateral sclerosis (ALS); a psychotic disorder including schizophrenia, bipolar disorder, or autism; a pain disorder including migraine, temporomandibular disorders, neuropathic pain, visceral pain, or complex regional pain syndrome; an addiction including alcohol addiction, cocaine addiction, heroin addiction, methamphetamine addiction, or nicotine addiction; or a cancer, including glioblastoma; or a mood disorder, including anxiety disorders, depressive disorders, borderline personality disorder, attention-deficit-hyperactivity disorder, suicidal behavior, eating disorders, posttraumatic stress disorder, gulf war illness, and obsessive-Compulsive Disorder, in a subject in need thereof, the method comprising administering to the subject an effective amount of a compound provided herein, or a pharmaceutically acceptable salt thereof.

Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

DETAILED DESCRIPTION

Figure 1:
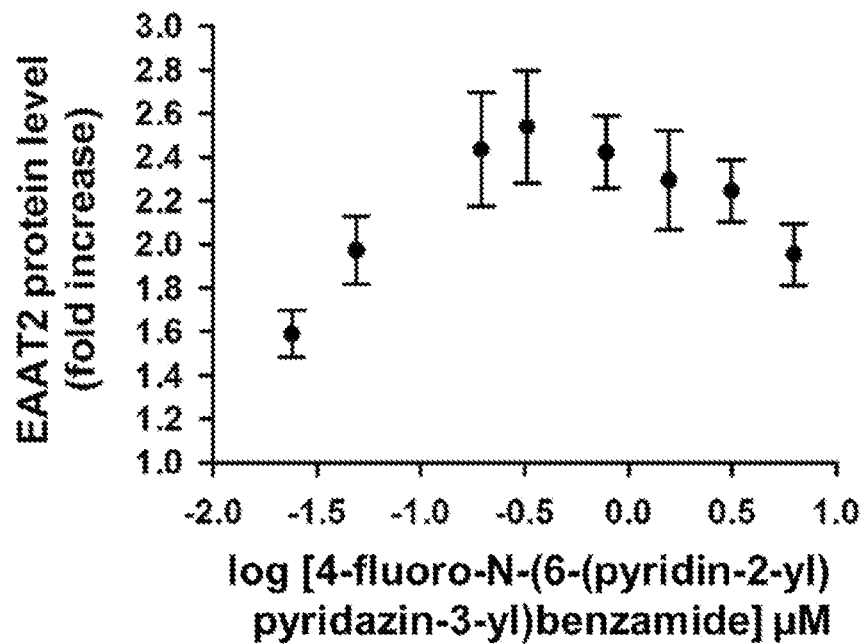
FIG. 1 shows EAAT2 expression in a primary astrocyte cell line upon contacting 4-fluoro-N-(6-(pyridin-2-yl) pyridazin-3-yl)benzamide (i.e., compound of Example 4). Cells were treated with the compound for 24 h and harvested for measuring EAAT2 protein levels by semi-quantitative Western blot analysis (n=4).
Figure 2:
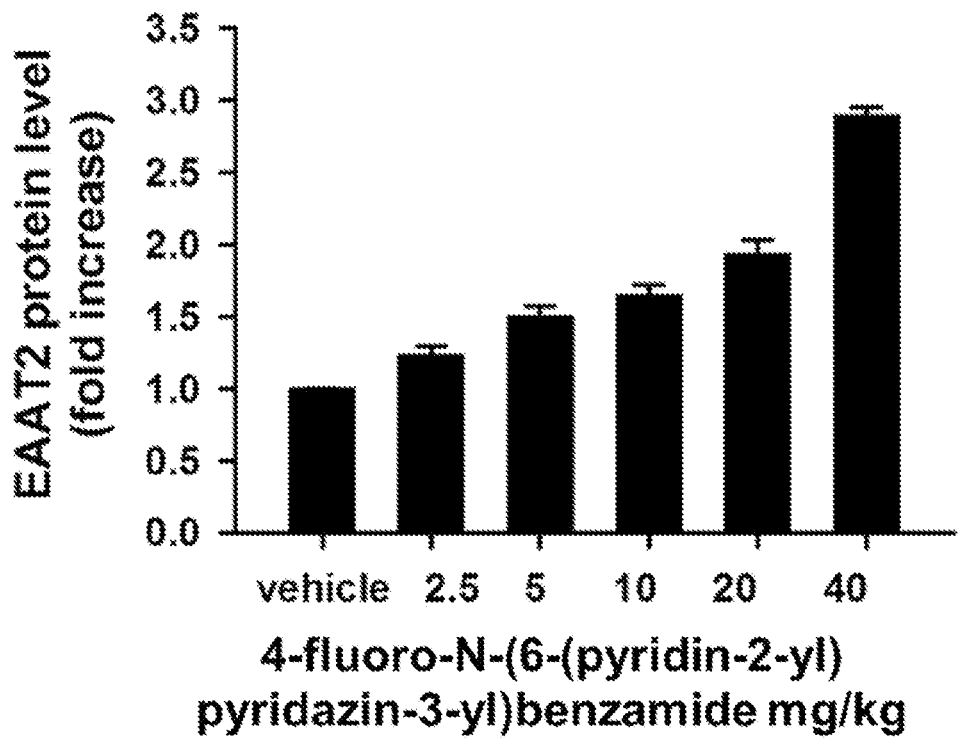
FIG. 2 shows EAAT2 expression in mouse brain upon contacting with 4-fluoro-N-(6-(pyridin-2-yl)pyridazin-3-yl) benzamide (i.e. the compound of Example 4). Mice received a single dose of the compound (n=3/dose) by oral gavage. Brains were harvested at 24 h post-treatment. EAAT2 protein levels were analyzed by semi-quantitative Western blot analysis. The compound dose-dependently increased EAAT2 levels.

The compounds provided herein activate EAAT2, and thus are useful in methods of reducing extracellular glutamate levels, thereby reducing glutamate excitotoxicity in cells and tissues, making them therapeutically useful in treating or preventing conditions associated with glutamate excitotoxicity, e.g., acute neurological conditions such as ischemic stroke, epilepsy, and trauma, as well as chronic adult-onset neurodegenerative disorders such as Alzheimer's disease and amyotrophic lateral sclerosis (ALS). In some embodiments, the compounds provided herein (e.g., compounds of Formula (I), compounds of Formula (Ia), compounds of Formula (II), compounds of Formula (IIa), compounds of Formula (III), compounds of Formula (IIIa), compounds of Formula (IV), and Formula (IVa)), are therapeutically useful in treating or preventing depression.

Compounds

The present application provides, inter alia, a compound of Formula (I):

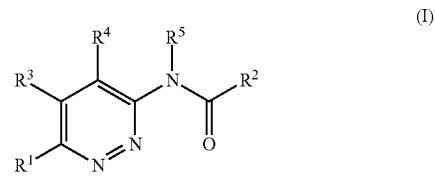

or a pharmaceutically acceptable salt thereof, wherein:

$R^1$ is selected from the group consisting of 6-10 membered aryl and 5-10 membered heteroaryl, each of which is optionally substituted by 1, 2, 3, or 4 independently selected $R^A$ groups;

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^3$, $R^4$, and $R^5$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino.

In some embodiments, $R^1$ is a 6-10 membered aryl which is optionally substituted by 1, 2, 3, or 4 independently selected $R^A$ groups. In some embodiments, $R^1$ is an unsubstituted 6-10 membered aryl. In some embodiments, $R^1$ is a 6-10 membered aryl which is optionally substituted by 1 $R^A$ group. In some embodiments, $R^1$ is a 6-10 membered aryl which is optionally substituted by 2 independently selected $R^A$ groups. In some embodiments, $R^1$ is a 6-10 membered aryl which is optionally substituted by 3 independently selected $R^A$ groups. In some embodiments, $R^1$ is a 6-10 membered aryl which is optionally substituted by 4 independently selected $R^A$ groups. In some embodiments, $R^1$ is phenyl which is optionally substituted by 1, 2, 3, or 4 independently selected $R^A$ groups. In some embodiments, $R^1$ is unsubstituted phenyl. In some embodiments, $R^1$ is phenyl which is optionally substituted by 1 $R^A$ group. In some embodiments, $R^1$ is phenyl which is optionally substituted by 2 independently selected $R^A$ groups. In some embodiments, $R^1$ is phenyl which is optionally substituted by 3 independently selected $R^A$ groups. In some embodiments, $R^1$ is phenyl which is optionally substituted by 4 independently selected $R^A$ groups. In some embodiments, each $R^A$ is independently selected from the group consisting of halo, $C_{1-6}$ alkyl, $OR^a$, and $C_{1-6}$ alkoxy. In some embodiments, each $R^A$ is an independently selected halo group. In some embodiments, each $R^A$ is an independently selected $C_{1-6}$ alkyl group. In some embodiments, each $R^A$ is an independently selected $OR^a$ group. In some embodiments, each $R^A$ is an independently selected $C_{1-6}$ alkoxy group. In some embodiments, each $R^A$ is independently selected from the group consisting of $CH_3$, F, OH, and $OCH_3$. In some embodiments, each $R^A$ is $CH_3$. In some embodiments, each $R^A$ is F. In some embodiments, each $R^A$ is OH. In some embodiments, each $R^A$ is $OCH_3$.

In some embodiments, $R^1$ is a 5-10 membered heteroaryl which is optionally substituted by 1, 2, 3, or 4 independently selected $R^A$ groups. In some embodiments, $R^1$ is an unsubstituted 5-10 membered heteroaryl. In some embodiments, $R^1$ is a 5-10 membered heteroaryl which is optionally substituted by 1 $R^A$ group. In some embodiments, $R^1$ is a 5-10 membered heteroaryl which is optionally substituted by 2 independently selected $R^A$ groups. In some embodiments, $R^1$ is a 5-10 membered heteroaryl which is optionally substituted by 3 independently selected $R^A$ groups. In some embodiments, $R^1$ is a 5-10 membered heteroaryl which is optionally substituted by 4 independently selected $R^A$ groups. In some embodiments, $R^1$ is pyridyl which is optionally substituted by 1, 2, 3, or 4 independently selected $R^A$ groups. In some embodiments, $R^1$ is an unsubstituted pyridyl. In some embodiments, $R^1$ is pyridyl which is optionally substituted by 1, 2, 3, or 4 independently selected $R^A$ groups. In some embodiments, $R^1$ is pyridyl which is optionally substituted by 1 $R^A$ group. In some embodiments, $R^1$ is pyridyl which is optionally substituted by 2 independently selected $R^A$ groups. In some embodiments, $R^1$ is pyridyl which is optionally substituted by 3 independently selected $R^A$ groups. In some embodiments, $R^1$ is pyridyl which is optionally substituted by 4 independently selected $R^A$ groups. In some embodiments, each $R^A$ is independently selected from the group consisting of halo, $C_{1-6}$ alkyl, $OR^a$, and $C_{1-6}$ alkoxy. In some embodiments, each $R^A$ is an independently selected halo group. In some embodiments, each $R^A$ is an independently selected $C_{1-6}$ alkyl group. In some embodiments, each $R^A$ is an independently selected $OR^a$ group. In some embodiments, each $R^A$ is an independently selected $C_{1-6}$ alkoxy group. In some embodiments, each $R^A$ is independently selected from the group consisting of $CH_3$, F, OH, and $OCH_3$. In some embodiments, each $R^A$ is $CH_3$. In some embodiments, each $R^A$ is F. In some embodiments, each $R^A$ is OH. In some embodiments, each $R^A$ is $OCH_3$.

In some embodiments, $R^2$ is a 6-10 membered aryl which is optionally substituted by 1, 2, 3, or 4 independently selected $R^B$ groups. In some embodiments, $R^2$ is an unsubstituted 6-10 membered aryl. In some embodiments, $R^2$ is a 6-10 membered aryl which is optionally substituted by 1 $R^B$ group. In some embodiments, $R^2$ is a 6-10 membered aryl which is optionally substituted by 2 independently selected $R^B$ groups. In some embodiments, $R^2$ is a 6-10 membered aryl which is optionally substituted by 3 independently selected $R^B$ groups. In some embodiments, $R^2$ is a 6-10 membered aryl which is optionally substituted by 4 independently selected $R^B$ groups. In some embodiments, $R^2$ is phenyl which is optionally substituted by 1, 2, 3, or 4 independently selected $R^B$ groups. In some embodiments, $R^2$ is unsubstituted phenyl. In some embodiments, $R^2$ is phenyl which is optionally substituted by 1 $R^B$ group. In some embodiments, $R^2$ is phenyl which is optionally substituted by 2 independently selected $R^B$ groups. In some embodiments, $R^2$ is phenyl which is optionally substituted by 3 independently selected $R^B$ groups. In some embodiments, $R^2$ is phenyl which is optionally substituted by 4 independently selected $R^B$ groups. In some embodiments, each $R^B$ is independently selected from the group consisting of halo, $C_{1-6}$ alkyl, $OR^a$, and $C_{1-6}$ alkoxy. In some embodiments, each $R^B$ is an independently selected halo group. In some embodiments, each $R^B$ is an independently selected $C_{1-6}$ alkyl group. In some embodiments, each $R^B$ is an independently selected $OR^a$ group. In some embodiments, each $R^B$ is an independently selected $C_{1-6}$ alkoxy group. In some embodiments, each $R^B$ is independently selected from the group consisting of F, Cl, OH, and $OCH_3$. In some embodiments, each $R^B$ is F. In some embodiments, each $R^B$ is Cl. In some embodiments, each $R^B$ is OH. In some embodiments, each $R^B$ is $OCH_3$.

In some embodiments, $R^2$ is a 5-10 membered heteroaryl which is optionally substituted by 1, 2, 3, or 4 independently selected $R^B$ groups. In some embodiments, $R^2$ is an unsubstituted 5-10 membered heteroaryl. In some embodiments, $R^2$ is a 5-10 membered heteroaryl which is optionally by 1 $R^B$ group. In some embodiments, $R^2$ is a 5-10 membered heteroaryl which is optionally substituted by 2 independently selected $R^B$ groups. In some embodiments, $R^2$ is a 5-10 membered heteroaryl which is optionally substituted by 3 independently selected $R^B$ groups. In some embodiments, $R^2$ is a 5-10 membered heteroaryl which is optionally substituted by 4 independently selected $R^B$ groups.

In some embodiments, $R^2$ is selected from the group consisting of pyridyl, pyridazinyl, pyrimidinyl, thiazolyl, and imidazolyl, each of which is optionally substituted by 1, 2, 3, or 4 independently selected $R^B$ groups. In some embodiments, $R^2$ is pyridyl which is optionally substituted by 1, 2, 3, or 4 independently selected $R^B$ groups. In some embodiments, $R^2$ is pyridyl which is optionally substituted by 1, 2, 3, or 4 independently selected $R^B$ groups. In some embodiments, $R^2$ is unsubstituted pyridyl. In some embodiments, $R^2$ is pyridyl which is optionally substituted by 1 or 2 independently selected $R^B$ groups. In some embodiments, $R^2$ is pyridazinyl which is optionally substituted by 1, 2, 3, or 4 independently selected $R^B$ groups. In some embodiments, $R^2$ is unsubstituted pyridazinyl. In some embodiments, $R^2$ is pyrimidinyl which is optionally substituted by 1, 2, 3, or 4 independently selected $R^B$ groups. In some embodiments, $R^2$ is unsubstituted pyrimidinyl. In some embodiments, $R^2$ is thiazolyl which is optionally substituted by 1, 2, 3, or 4 independently selected $R^B$ groups. In some embodiments, $R^2$ is unsubstituted thiazolyl. In some embodiments, $R^2$ is imidazolyl which is optionally substituted by 1, 2, 3, or 4 independently selected $R^B$ groups. In some embodiments, $R^2$ is unsubstituted imidazolyl. In some embodiments, each $R^B$ is independently selected from the group consisting of halo and $C_{1-6}$ alkyl. In some embodiments, each $R^B$ is an independently selected halo group. In some embodiments, each $R^B$ is an independently selected $C_{1-6}$ alkyl group. In some embodiments, each $R^B$ is independently selected from the group consisting of F and $CH_3$. In some embodiments, each $R^B$ is F. In some embodiments, each $R^B$ is $CH_3$.

In some embodiments, $R^2$ is a 5-10 membered heterocyclyl which is optionally substituted by 1, 2, 3, or 4 independently selected $R^B$ groups. In some embodiments, $R^2$ is an unsubstituted 5-10 membered heterocyclyl. In some embodiments, $R^2$ is a 5-10 membered heterocyclyl which is optionally substituted by 1 $R^B$ group. In some embodiments, $R^2$ is a 5-10 membered heterocyclyl which is optionally substituted 2 independently selected $R^B$ groups. In some embodiments, $R^2$ is a 5-10 membered heterocyclyl which is optionally substituted 3 independently selected $R^B$ groups. In some embodiments, $R^2$ is a 5-10 membered heterocyclyl which is optionally substituted 4 independently selected $R^B$ groups. In some embodiments, $R^2$ is piperidinyl, which is optionally substituted by 1, 2, 3, or 4 independently selected $R^B$ groups. In some embodiments, $R^2$ is unsubstituted piperidinyl. In some embodiments, $R^2$ is piperidinyl, which is optionally substituted by 1 $R^B$ group. In some embodiments, $R^2$ is piperidinyl which is optionally substituted by $C_{1-6}$ alkyl. In some embodiments, $R^2$ is piperidinyl which is optionally substituted by $CH_3$.

In some embodiments, $R^3$ is H. In some embodiments, $R^4$ is H. In some embodiments, $R^3$ and $R^4$ are H. In some embodiments, $R^5$ is H. In some embodiments, $R^3$, $R^4$, and $R^5$ are H.

In some embodiments, the compound of Formula (I) is a compound of Formula (Ia):

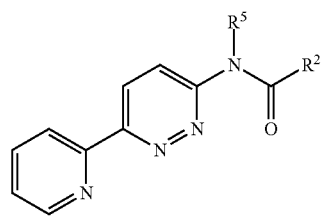

(Ia)

or a pharmaceutically acceptable salt thereof, wherein:

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^5$ is selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl; and each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$alkyl)aminosulfonylamino, aminocarbonylamino, $C_{1-6}$alkylaminocarbonylamino, and di($C_{1-6}$ alkyl)aminocarbonylamino.

In some embodiments, $R^2$ is a 6-10 membered aryl which is optionally substituted by 1, 2, 3, or 4 independently selected $R^B$ groups. In some embodiments, $R^2$ is an unsubstituted 6-10 membered aryl. In some embodiments, $R^2$ is a 6-10 membered aryl which is optionally substituted by 1 $R^B$ group. In some embodiments, $R^2$ is a 6-10 membered aryl which is optionally substituted by 2 independently selected $R^B$ groups. In some embodiments, $R^2$ is a 6-10 membered aryl which is optionally substituted by 3 independently selected $R^B$ groups. In some embodiments, $R^2$ is a 6-10 membered aryl which is optionally substituted by 4 independently selected $R^B$ groups. In some embodiments, $R^2$ is phenyl which is optionally substituted by 1, 2, 3, or 4 independently selected $R^B$ groups. In some embodiments, $R^2$ is unsubstituted phenyl. In some embodiments, $R^2$ is phenyl which is optionally substituted by 1 $R^B$ group. In some embodiments, $R^2$ is phenyl which is optionally substituted by 2 independently selected $R^B$ groups. In some embodiments, $R^2$ is phenyl which is optionally substituted by 3 independently selected $R^B$ groups. In some embodiments, $R^2$ is phenyl which is optionally substituted by 4 independently selected $R^B$ groups. In some embodiments, each $R^B$ is independently selected from the group consisting of halo, $C_{1-6}$ alkyl, $OR^a$, and $C_{1-6}$ alkoxy. In some embodiments, each $R^B$ is an independently selected halo group. In some embodiments, each $R^B$ is an independently selected $C_{1-6}$ alkyl group. In some embodiments, each $R^B$ is an independently selected $OR^a$ group. In some embodiments, each $R^B$ is an independently selected $C_{1-6}$ alkoxy group. In some embodiments, each $R^B$ is independently selected from the group consisting of F, Cl, OH, and $OCH_3$. In some embodiments, each $R^B$ is F. In some embodiments, each $R^B$ is Cl. In some embodiments, each $R^B$ is OH. In some embodiments, each $R^B$ is $OCH_3$.

In some embodiments, $R^2$ is a 5-10 membered heteroaryl which is optionally substituted by 1, 2, 3, or 4 independently selected $R^B$ groups. In some embodiments, $R^2$ is an unsubstituted 5-10 membered heteroaryl. In some embodiments, $R^2$ is a 5-10 membered heteroaryl which is optionally by 1 $R^B$ group. In some embodiments, $R^2$ is a 5-10 membered heteroaryl which is optionally substituted by 2 independently selected $R^B$ groups. In some embodiments, $R^2$ is a 5-10 membered heteroaryl which is optionally substituted by 3 independently selected R$^B$ groups. In some embodiments, R$^2$ is a 5-10 membered heteroaryl which is optionally substituted by 4 independently selected R$^B$ groups.

In some embodiments, R$^2$ is selected from the group consisting of pyridyl, pyridazinyl, pyrimidinyl, thiazolyl, and imidazolyl, each of which is optionally substituted by 1, 2, 3, or 4 independently selected R$^B$ groups. In some embodiments, R$^2$ is pyridyl which is optionally substituted by 1, 2, 3, or 4 independently selected R$^B$ groups. In some embodiments, R$^2$ is pyridyl which is optionally substituted by 1, 2, 3, or 4 independently selected R$^B$ groups. In some embodiments, R$^2$ is unsubstituted pyridyl. In some embodiments, R$^2$ is pyridyl which is optionally substituted by 1 or 2 independently selected R$^B$ groups. In some embodiments, R$^2$ is pyridazinyl which is optionally substituted by 1, 2, 3, or 4 independently selected R$^B$ groups. In some embodiments, R$^2$ is unsubstituted pyridazinyl. In some embodiments, R$^2$ is pyrimidinyl which is optionally substituted by 1, 2, 3, or 4 independently selected R$^B$ groups. In some embodiments, R$^2$ is unsubstituted pyrimidinyl. In some embodiments, R$^2$ is thiazolyl which is optionally substituted by 1, 2, 3, or 4 independently selected R$^B$ groups. In some embodiments, R$^2$ is unsubstituted thiazolyl. In some embodiments, R$^2$ is imidazolyl which is optionally substituted by 1, 2, 3, or 4 independently selected R$^B$ groups. In some embodiments, R$^2$ is unsubstituted imidazolyl. In some embodiments, each R$^B$ is independently selected from the group consisting of halo and C$_{1-6}$ alkyl. In some embodiments, each R$^B$ is an independently selected halo group. In some embodiments, each R$^B$ is an independently selected C$_{1-6}$ alkyl group. In some embodiments, each R$^B$ is independently selected from the group consisting of F and CH$_3$. In some embodiments, each R$^B$ is F. In some embodiments, each R$^B$ is CH$_3$.

In some embodiments, R$^2$ is a 5-10 membered heterocyclyl which is optionally substituted by 1, 2, 3, or 4 independently selected R$^B$ groups. In some embodiments, R$^2$ is an unsubstituted 5-10 membered heterocyclyl. In some embodiments, R$^2$ is a 5-10 membered heterocyclyl which is optionally substituted by 1 R$^B$ group. In some embodiments, R$^2$ is a 5-10 membered heterocyclyl which is optionally substituted 2 independently selected R$^B$ groups. In some embodiments, R$^2$ is a 5-10 membered heterocyclyl which is optionally substituted 3 independently selected R$^B$ groups. In some embodiments, R$^2$ is a 5-10 membered heterocyclyl which is optionally substituted 4 independently selected R$^B$ groups. In some embodiments, R$^2$ is piperidinyl, which is optionally substituted by 1, 2, 3, or 4 independently selected R$^B$ groups. In some embodiments, R$^2$ is unsubstituted piperidinyl. In some embodiments, R$^2$ is piperidinyl, which is optionally substituted by 1 R$^B$ group. In some embodiments, R$^2$ is piperidinyl which is optionally substituted by C$_{1-6}$ alkyl. In some embodiments, R$^2$ is piperidinyl which is optionally substituted by CH$_3$.

In some embodiments, R$^5$ is H.

In some embodiments, the compound of Formula (I) or the compound of Formula (Ia) is selected from the group consisting of:

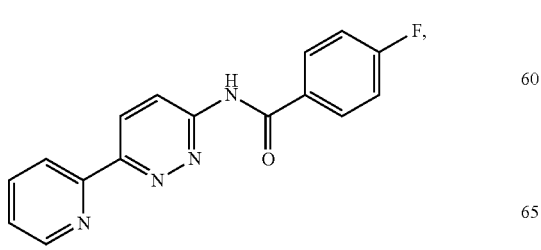

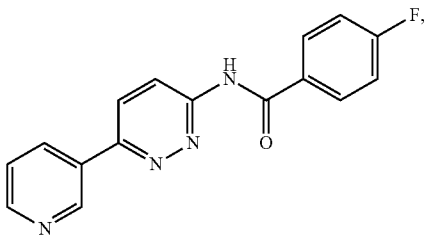

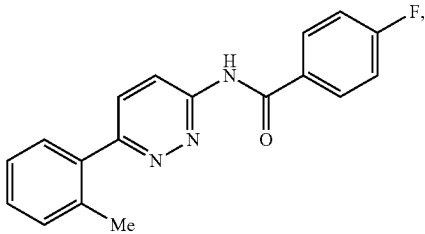

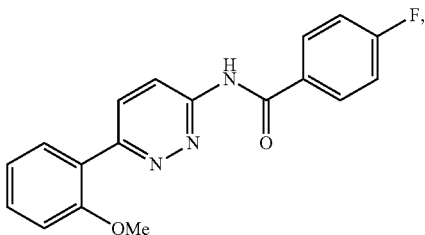

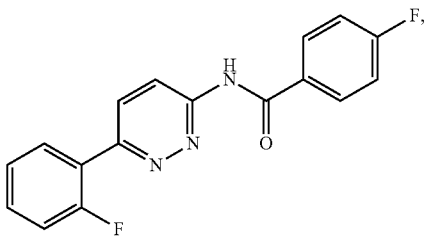

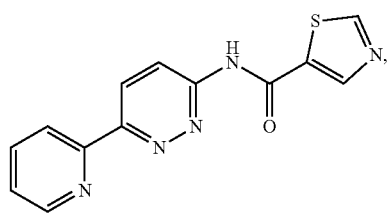

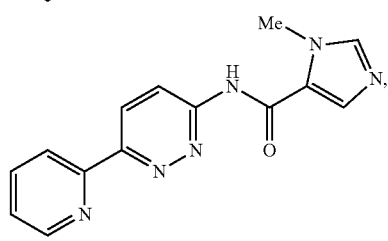

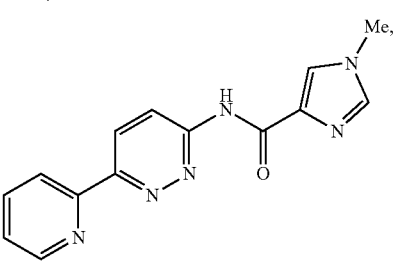

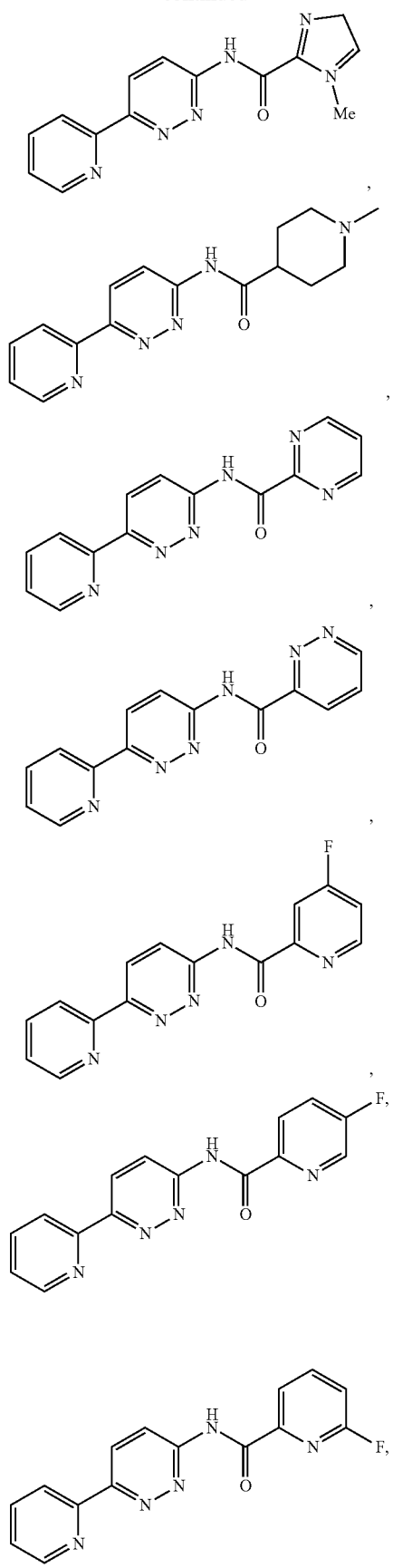
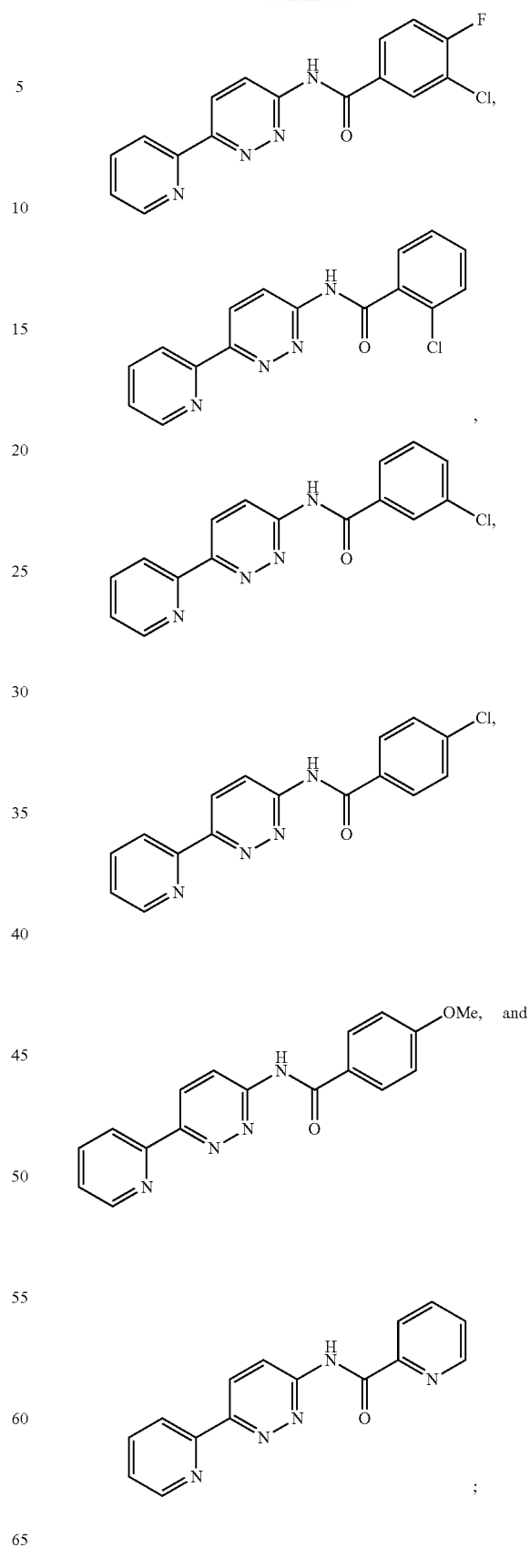
or a pharmaceutically acceptable salt thereof.

The present application further provides a compound of Formula (II):

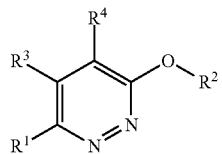

or a pharmaceutically acceptable salt thereof, wherein:

$R^1$ is selected from the group consisting of 6-10 membered aryl and 5-10 membered heteroaryl, each of which is optionally substituted by 1, 2, 3, or 4 independently selected $R^A$ groups;

$R^2$ is $-(CHR^E)_nR^5$;

$R^5$ is selected from the group consisting of $NR^CR^D$, $C(O)NR^CR^D$, $C(O)OR^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments:

$R^1$ is selected from the group consisting of 6-10 membered aryl and 5-10 membered heteroaryl, each of which is optionally substituted by 1, 2, 3, or 4 independently selected $R^A$ groups;

$R^2$ is $-(CHR^E)_nR^5$;

$R^5$ is selected from the group consisting of $NR^CR^D$, $C(O)NR^CR^D$, $C(O)OR^C$, and 5-10 membered heteroaryl, wherein the 5-10 membered heteroaryl is optionally substituted by 1, 2, 3, or 4 independently selected $R^B$ groups;

$R^E$ is H or $C_{1-6}$ alkyl, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 1, 2, 3, 4, or 5.

In some embodiments, $R^1$ is a 5-10 membered heteroaryl which is optionally substituted by 1, 2, 3, or 4 independently selected $R^A$ groups. In some embodiments, $R^1$ is an unsubstituted 5-10 membered heteroaryl. In some embodiments, $R^1$ is a 5-10 membered heteroaryl which is optionally substituted by 1 $R^A$ group. In some embodiments, $R^1$ is a 5-10 membered heteroaryl which is optionally substituted by 2 independently selected $R^A$ groups. In some embodiments, $R^1$ is a 5-10 membered heteroaryl which is optionally substituted by 3 independently selected $R^A$ groups. In some embodiments, $R^1$ is a 5-10 membered heteroaryl which is optionally substituted by 4 independently selected $R^A$ groups. In some embodiments, $R^1$ is pyridyl which is optionally substituted by 1, 2, 3, or 4 independently selected $R^A$ groups. In some embodiments, $R^1$ is unsubstituted pyridyl. In some embodiments, $R^1$ is pyridyl which is optionally substituted by 1 $R^A$ group. In some embodiments, $R^1$ is pyridyl which is optionally substituted by 2 independently selected $R^A$ groups. In some embodiments, $R^1$ is pyridyl which is optionally substituted by 3 independently selected $R^A$ groups. In some embodiments, $R^1$ is pyridyl which is optionally substituted by 4 independently selected $R^A$ groups.

In some embodiments, $R^5$ is selected from the group consisting of $C_{3-6}$ cycloalkyl, phenyl, 4-6 membered heterocycloalkyl, and 5-10 membered heteroaryl, each of which is optionally substituted by 1, 2, 3, or 4 independently selected $R^B$ groups. In some embodiments, $R^5$ is selected from the group consisting of $C_{3-6}$ cycloalkyl, phenyl, 4-6 membered heterocycloalkyl, and 5-10 membered heteroaryl, each of which is optionally substituted by 1 or 2 independently selected $R^B$ groups. In some embodiments, $R^5$ is selected from the group consisting of cyclopentyl, cyclohexyl, phenyl, isoxazolyl, isoquinolinyl, benzo[d]oxazolyl, pyrazolyl, pyrrolidinyl, imidazolyl, pyrrolyl, benzo[d]imidazolyl, pyrrolyl-2,5-dione, and pyrrolidinyl-2-one, each of which is optionally substituted by 1 or 2 $R^B$ groups. In some embodiments, $R^5$ is selected from the group consisting of cyclopentyl, 2-(dimethylamino)cyclopentyl, 2-aminocyclohexyl, 2-(dimethylamino)cyclohexyl, phenyl, isoxazolyl, isoquinolinyl, benzo[d]oxazolyl, pyrazolyl, pyrrolidinyl, 1-methylpyrrolidinyl, imidazolyl, pyrrolyl, benzo[d]imidazolyl, 2-methyl-1H-benzo[d]imidazolyl, pyrrolyl-2,5-dione, and pyrrolidinyl-2-one.

In some embodiments, $R^5$ is a 5-10 membered heteroaryl which is optionally substituted by 1, 2, 3, or 4 independently selected $R^B$ groups. In some embodiments, $R^5$ is an unsubstituted 5-10 membered heteroaryl. In some embodiments, $R^5$ is a 5-10 membered heteroaryl which is optionally substituted by 1 $R^B$ group. In some embodiments, $R^5$ is a 5-10 membered heteroaryl which is optionally substituted by 2 independently selected $R^B$ groups. In some embodiments, $R^5$ is a 5-10 membered heteroaryl which is optionally substituted by 3 independently selected $R^B$ groups. In some embodiments, $R^5$ is a 5-10 membered heteroaryl which is optionally substituted by 4 independently selected $R^B$ groups. In some embodiments, $R^5$ is selected from oxazolyl and pyridyl, each of which is optionally substituted by 1, 2, 3, or 4 independently selected $R^B$ groups. In some embodiments, $R^5$ is oxazolyl which is optionally substituted by 1, 2, 3, or 4 independently selected $R^B$ groups. In some embodiments, $R^5$ is an unsubstituted oxazolyl. In some embodiments, $R^5$ is pyridyl which is optionally substituted by 1, 2, 3, or 4 independently selected $R^B$ groups. In some embodiments, $R^5$ is unsubstituted pyridyl.

In some embodiments, $R^5$ is $NR^CR^D$, wherein $R^C$ and $R^D$ independently selected from H and $C_{1-6}$ alkyl. In some embodiments, $R^C$ and $R^D$ are each an independently selected $C_{1-6}$ alkyl group. In some embodiments, $R^C$ and $R^D$ are $CH_3$. In some embodiments, $R^C$ and $R^D$ are H.

In some embodiments, $R^5$ is $C(O)NR^CR^D$, wherein $R^C$ and $R^D$ are independently selected from H, $C_{1-6}$ alkyl, and 6-10 membered aryl optionally substituted with 1, 2, 3, or 4 independently selected $R^6$ groups; or alternatively, $R^C$ and $R^D$ attached to the same N atom, together with the N atom to which they are attached, form a 4-6 membered heterocycloalkyl group optionally substituted with 1, 2, or 3 independently selected $R^6$ groups. In some embodiments, $R^5$ is $C(O)NR^CR^D$, wherein $R^C$ and $R^D$ are independently selected from H, $C_{1-6}$ alkyl, and 6-10 membered aryl optionally substituted with 1, 2, 3, or 4 independently selected $R^6$ groups. In some embodiments, $R^C$ and $R^D$ are independently selected from H and $C_{1-6}$ alkyl. In some embodiments, $R^C$ and $R^D$ are independently selected from H, $C_{1-6}$ alkyl, and phenyl optionally substituted with $C_{1-6}$ alkyl. In some embodiments, $R^C$ and $R^D$ are independently selected from H, $C_{1-6}$ alkyl, and phenyl optionally substituted with $CH_3$. In some embodiments, $R^5$ is $C(O)NR^CR^D$, wherein $R^C$ and $R^D$ attached to the same N atom, together with the N atom to which they are attached, form a 4-6 membered heterocycloalkyl group optionally substituted with 1, 2, or 3 independently selected $R^6$ groups. In some embodiments, $R^C$ and $R^D$ attached to the same N atom, together with the N atom to which they are attached, form a 4-6 membered heterocycloalkyl group. In some embodiments, $R^5$ is $C(O)OR^C$, wherein $R^C$ is H or $C_{1-6}$ alkyl.

In some embodiments, each $R^E$ is independently selected from the group consisting of H, $C_{1-3}$ alkyl, $C_{1-3}$ alkoxy, and amino. In some embodiments, each $R^E$ is independently selected from the group consisting of H, methyl, methoxy, and amino.

In some embodiments, $R^E$ is H. In some embodiments, $R^E$ is $C_{1-6}$ alkyl which is optionally substituted by 1, 2, 3, or 4 independently selected $R^6$ groups.

In some embodiments, $R^3$ is H. In some embodiments, $R^4$ is H. In some embodiments, $R^3$ and $R^4$ are H.

In some embodiments, n is 0, 1, 2, 3, or 4. In some embodiments, n is 0, 1, 2, or 3. In some embodiments, n is 0, 1, or 2. In some embodiments, n is 0 or 1. In some embodiments, n is 1, 2, 3, or 4. In some embodiments, n is 1, 2, or 3. In some embodiments, n is 1 or 2. In some embodiments, n is 2, 3, 4, or 5. In some embodiments, n is 2, 3, or 4. In some embodiments, n is 2 or 3. In some embodiments, n is 3, 4, or 5. In some embodiments, n is 3 or 4. In some embodiments, n is 4 or 5. In some embodiments, n is 0. In some embodiments, n is 1 or 2. In some embodiments, n is 1. In some embodiments, n is 2. In some embodiments, n is 3. In some embodiments, n is 4. In some embodiments, n is 5.

In some embodiments, the compound of Formula (II) is a compound of Formula (IIa):

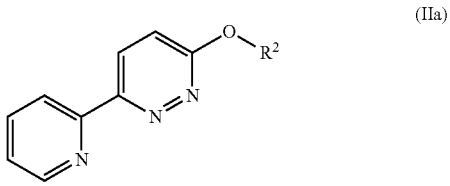

(IIa)

or a pharmaceutically acceptable salt thereof, wherein:

$R^2$ is —(CHR$^E$)$_n$R$^5$;

$R^5$ is selected from the group consisting of NR$^C$R$^D$, C(O)NR$^C$R$^D$, C(O)OR$^C$, C$_{3-10}$ cycloalkyl, C$_{6-10}$ aryl, 4-10 membered heterocycloalkyl, and 5-10 membered heteroaryl, wherein the C$_{3-10}$ cycloalkyl, C$_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, C$_{1-6}$ alkyl, C$_{1-6}$ alkoxy, and amino, wherein said C$_{1-6}$ alkyl is optionally substituted by 1, 2, 3, or 4 independently selected $R^6$ groups;

$R^3$ and $R^4$ are independently selected from H and C$_{1-6}$ alkyl;

each $R^B$ is independently selected from halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^a$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected $R^6$ groups;

$R^C$ and $R^D$ are independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, and 5-10 membered heteroaryl-C$_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, C$_{1-6}$ alkyl, C$_{1-6}$ haloalkyl, C$_{1-6}$ alkylthio, C$_{1-6}$ alkylsulfonyl, C$_{1-6}$ alkylcarbonyl, C$_{1-6}$ alkylaminosulfonyl, carbamyl, C$_{1-6}$ alkylcarbamyl, di(C$_{1-6}$ alkyl)carbamyl, aminosulfonyl, C$_{1-6}$ alkylaminosulfonyl, and di(C$_{1-6}$ alkyl)aminosulfonyl;

each $R^6$ is independently selected from OH, NO$_2$, CN, halo, C$_{1-6}$ alkyl, C$_{2-6}$ alkenyl, C$_{2-6}$ alkynyl, C$_{1-4}$ haloalkyl, C$_{1-6}$ alkoxy, C$_{1-6}$ haloalkoxy, cyano-C$_{1-3}$ alkyl, HO—C$_{1-3}$ alkyl, amino, C$_{1-6}$ alkylamino, di(C$_{1-6}$ alkyl)amino, thio, C$_{1-6}$ alkylthio, C$_{1-6}$ alkylsulfinyl, C$_{1-6}$ alkylsulfonyl, carbamyl, C$_{1-6}$ alkylcarbamyl, di(C$_{1-6}$alkyl)carbamyl, carboxy, C$_{1-6}$ alkylcarbonyl, C$_{1-6}$ alkoxycarbonyl, C$_{1-6}$ alkylcarbonylamino, C$_{1-6}$ alkylsulfonylamino, aminosulfonyl, C$_{1-6}$ alkylaminosulfonyl, di(C$_{1-6}$alkyl)aminosulfonyl, aminosulfonylamino, C$_{1-6}$ alkylaminosulfonylamino, di(C$_{1-6}$alkyl)aminosulfonylamino, aminocarbonylamino, C$_{1-6}$ alkylaminocarbonylamino, and di(C$_{1-6}$ alkyl)aminocarbonylamino; and n is 0, 1, 2, 3, 4, or 5.

In some embodiments, the compound of Formula (II) is a compound of Formula (IIa):

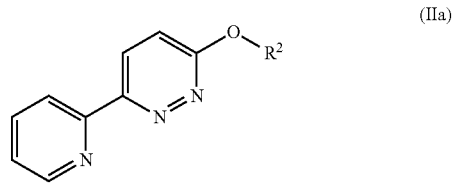

(IIa)

or a pharmaceutically acceptable salt thereof, wherein:

$R^2$ is —(CHR$^E$)$_n$R$^5$;

$R^5$ is selected from the group consisting of NR$^C$R$^D$, C(O)NR$^C$R$^D$, C(O)OR$^C$, and 5-10 membered heteroaryl, wherein the 5-10 membered heteroaryl is optionally substituted by 1, 2, 3, or 4 independently selected $R^B$ groups;

$R^E$ is H or C$_{1-6}$ alkyl, wherein said C$_{1-6}$ alkyl is optionally substituted by 1, 2, 3, or 4 independently selected $R^6$ groups;

each $R^B$ is independently selected from halo, C$_{1-6}$ alkyl, C$_{2-6}$ alkenyl, C$_{2-6}$ alkynyl, C$_{1-4}$ haloalkyl, CN, NO$_2$, OR$^a$, SR$^a$, C(O)R$^b$, C(O)NR$^c$R$^d$, C(O)OR$^a$, OC(O)R$^b$, OC(O)NR$^c$R$^d$, NR$^c$R$^d$, NR$^c$OR$^d$, NR$^c$C(O)R$^b$, NR$^c$C(O)OR$^d$, NR$^c$C(O)NR$^c$R$^d$, C(=NR$^e$)R$^b$, C(=NR$^e$)NR$^c$R$^d$, NR$^c$C(=NR$^e$)NR$^c$R$^d$, NR$^c$S(O)R$^b$, NR$^c$S(O)$_2$R$^b$, NR$^c$S(O)$_2$NR$^c$R$^d$, S(O)R$^b$, S(O)NR$^c$R$^d$, S(O)$_2$R$^b$, and S(O)$_2$NR$^c$R$^d$; wherein said C$_{1-6}$ alkyl, C$_{2-6}$ alkenyl, C$_{2-6}$ alkynyl, and C$_{1-4}$ haloalkyl are optionally substituted with 1, 2, 3, or 4 independently selected $R^6$ groups;

$R^C$ and $R^D$ are independently selected from H, C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, 5-10 membered heteroaryl-C$_{1-4}$ alkylene; wherein the C$_{1-6}$ alkyl, C$_{2-6}$ alkenyl, C$_{2-6}$ alkynyl, C$_{1-4}$ haloalkyl, C$_{3-10}$ cycloalkyl, 6-10 membered aryl, 5-10 membered heteroaryl, 4-10 membered heterocycloalkyl, C$_{3-10}$ cycloalkyl-C$_{1-4}$ alkylene, 4-10 membered heterocycloalkyl-C$_{1-4}$ alkylene, 6-10 membered aryl-C$_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 1, 2, 3, 4, or 5.

In some embodiments, $R^5$ is selected from the group consisting of $C_{3-6}$ cycloalkyl, phenyl, 4-6 membered heterocycloalkyl, and 5-10 membered heteroaryl, each of which is optionally substituted by 1, 2, 3, or 4 independently selected $R^B$ groups. In some embodiments, $R^5$ is selected from the group consisting of $C_{3-6}$ cycloalkyl, phenyl, 4-6 membered heterocycloalkyl, and 5-10 membered heteroaryl, each of which is optionally substituted by 1 or 2 independently selected $R^B$ groups. In some embodiments, $R^5$ is selected from the group consisting of cyclopentyl, cyclohexyl, phenyl, isoxazolyl, isoquinolinyl, benzo[d]oxazolyl, pyrazolyl, pyrrolidinyl, imidazolyl, pyrrolyl, benzo[d]imidazolyl, pyrrolyl-2,5-dione, and pyrrolidinyl-2-one, each of which is optionally substituted by 1 or 2 $R^B$ groups. In some embodiments, $R^5$ is selected from the group consisting of cyclopentyl, 2-(dimethylamino)cyclopentyl, 2-aminocyclohexyl, 2-(dimethylamino)cyclohexyl, phenyl, isoxazolyl, isoquinolinyl, benzo[d]oxazolyl, pyrazolyl, pyrrolidinyl, 1-methylpyrrolidinyl, imidazolyl, pyrrolyl, benzo[d]imidazolyl, 2-methyl-1H-benzo[d]imidazolyl, pyrrolyl-2,5-dione, and pyrrolidinyl-2-one.

In some embodiments, $R^5$ is a 5-10 membered heteroaryl which is optionally substituted by 1, 2, 3, or 4 independently selected $R^B$ groups. In some embodiments, $R^5$ is an unsubstituted 5-10 membered heteroaryl. In some embodiments, $R^5$ is a 5-10 membered heteroaryl which is optionally substituted by 1 $R^B$ group. In some embodiments, $R^5$ is a 5-10 membered heteroaryl which is optionally substituted by 2 independently selected $R^B$ groups. In some embodiments, $R^5$ is a 5-10 membered heteroaryl which is optionally substituted by 3 independently selected $R^B$ groups. In some embodiments, $R^5$ is a 5-10 membered heteroaryl which is optionally substituted by 4 independently selected $R^B$ groups. In some embodiments, $R^5$ is selected from oxazolyl and pyridyl, each of which is optionally substituted by 1, 2, 3, or 4 independently selected $R^B$ groups. In some embodiments, $R^5$ is oxazolyl which is optionally substituted by 1, 2, 3, or 4 independently selected $R^B$ groups. In some embodiments, $R^5$ is an unsubstituted oxazolyl. In some embodiments, $R^5$ is pyridyl which is optionally substituted by 1, 2, 3, or 4 independently selected $R^B$ groups. In some embodiments, $R^5$ is unsubstituted pyridyl.

In some embodiments, $R^5$ is $NR^CR^D$, wherein $R^C$ and $R^D$ independently selected from H and $C_{1-6}$ alkyl. In some embodiments, $R^C$ and $R^D$ are each an independently selected $C_{1-6}$ alkyl group. In some embodiments, $R^C$ and $R^D$ are $CH_3$. In some embodiments, $R^C$ and $R^D$ are H.

In some embodiments, $R^5$ is $C(O)NR^CR^D$, wherein $R^C$ and $R^D$ are independently selected from H, $C_{1-6}$ alkyl, and 6-10 membered aryl optionally substituted with 1, 2, 3, or 4 independently selected $R^6$ groups; or alternatively, $R^C$ and $R^D$ attached to the same N atom, together with the N atom to which they are attached, form a 4-6 membered heterocycloalkyl group optionally substituted with 1, 2, or 3 independently selected $R^6$ groups. In some embodiments, $R^5$ is $C(O)NR^CR^D$, wherein $R^C$ and $R^D$ are independently selected from H, $C_{1-6}$ alkyl, and 6-10 membered aryl optionally substituted with 1, 2, 3, or 4 independently selected $R^6$ groups. In some embodiments, $R^C$ and $R^D$ are independently selected from H and $C_{1-6}$ alkyl. In some embodiments, $R^C$ and $R^D$ are independently selected from H, $C_{1-6}$ alkyl, and phenyl optionally substituted with $C_{1-6}$ alkyl. In some embodiments, $R^C$ and $R^D$ are independently selected from H, $C_{1-6}$ alkyl, and phenyl optionally substituted with $CH_3$. In some embodiments, $R^5$ is $C(O)NR^CR^D$, wherein $R^C$ and $R^D$ attached to the same N atom, together with the N atom to which they are attached, form a 4-6 membered heterocycloalkyl group optionally substituted with 1, 2, or 3 independently selected $R^6$ groups. In some embodiments, $R^C$ and $R^D$ attached to the same N atom, together with the N atom to which they are attached, form a 4-6 membered heterocycloalkyl group. In some embodiments, $R^5$ is $C(O)OR^C$, wherein $R^C$ is H or $C_{1-6}$ alkyl.

In some embodiments, each $R^E$ is independently selected from the group consisting of H, $C_{1-3}$ alkyl, $C_{1-3}$ alkoxy, and amino. In some embodiments, each $R^E$ is independently selected from the group consisting of H, methyl, methoxy, and amino. In some embodiments, $R^E$ is H. In some embodiments, $R^E$ is $C_{1-6}$ alkyl which is optionally substituted by 1, 2, 3, or 4 independently selected $R^6$ groups.

In some embodiments, n is 0, 1, 2, 3, or 4. In some embodiments, n is 0, 1, 2, or 3. In some embodiments, n is 0, 1, or 2. In some embodiments, n is 0 or 1. In some embodiments, n is 1, 2, 3, or 4. In some embodiments, n is 1, 2, or 3. In some embodiments, n is 1 or 2. In some embodiments, n is 2, 3, 4, or 5. In some embodiments, n is 2, 3, or 4. In some embodiments, n is 2 or 3. In some embodiments, n is 3, 4, or 5. In some embodiments, n is 3 or 4. In some embodiments, n is 4 or 5. In some embodiments, n is 1 or 2. In some embodiments, n is 1. In some embodiments, n is 2. In some embodiments, n is 3. In some embodiments, n is 4. In some embodiments, n is 5.

In some embodiments, the compound of Formula (II) or the compound of Formula (IIa) is selected from the group consisting of:

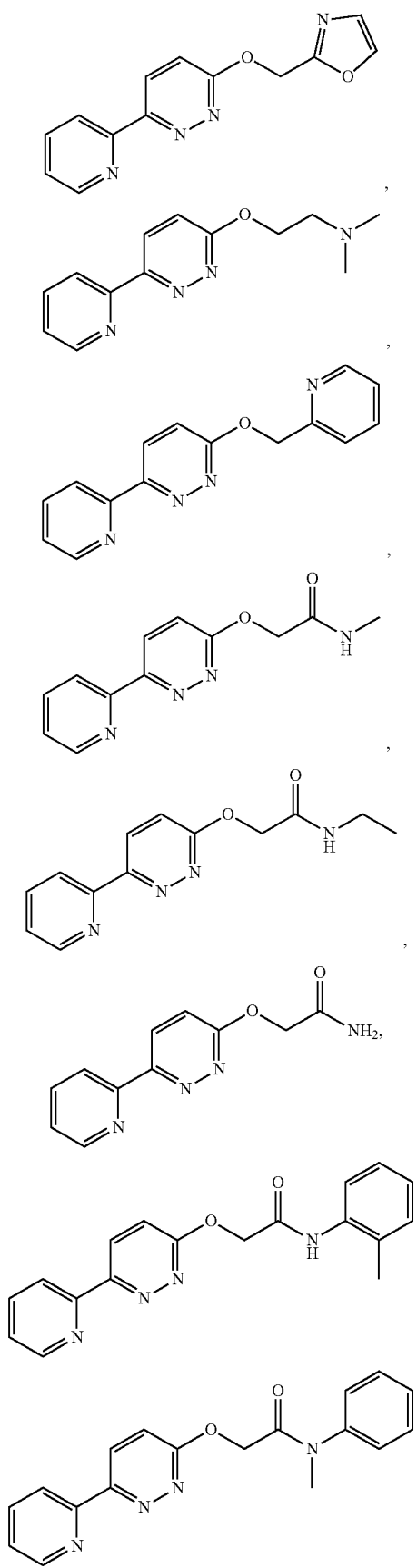
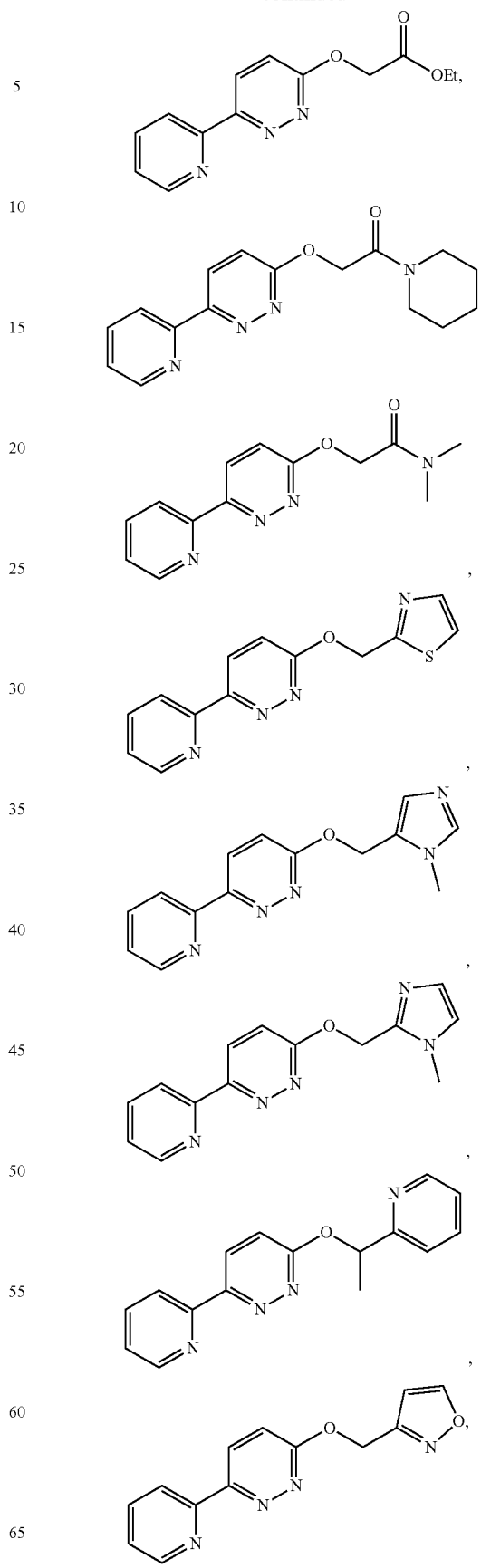

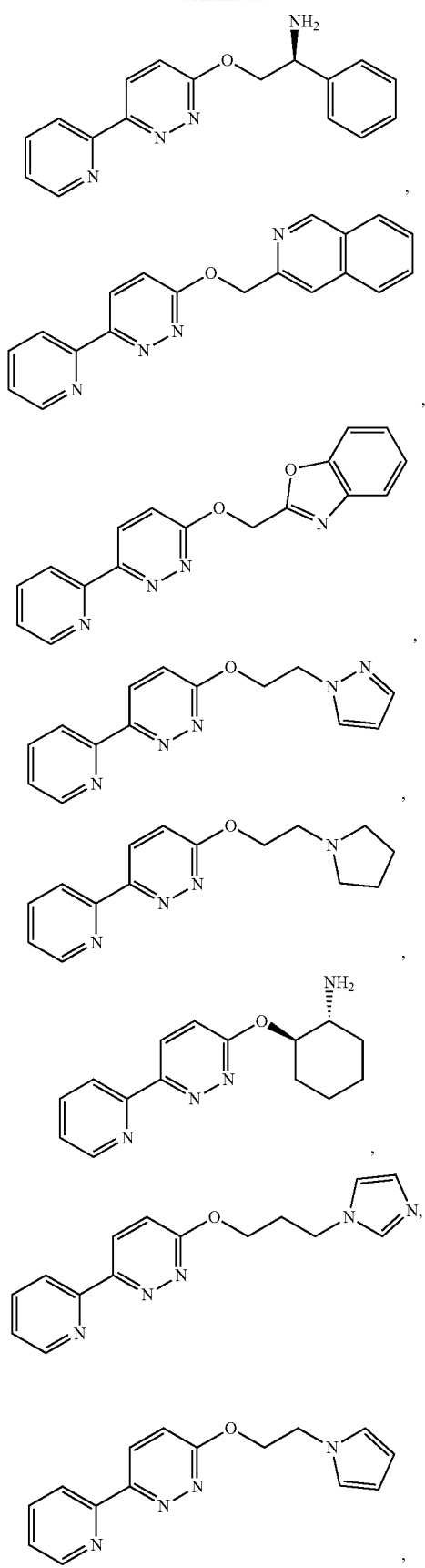
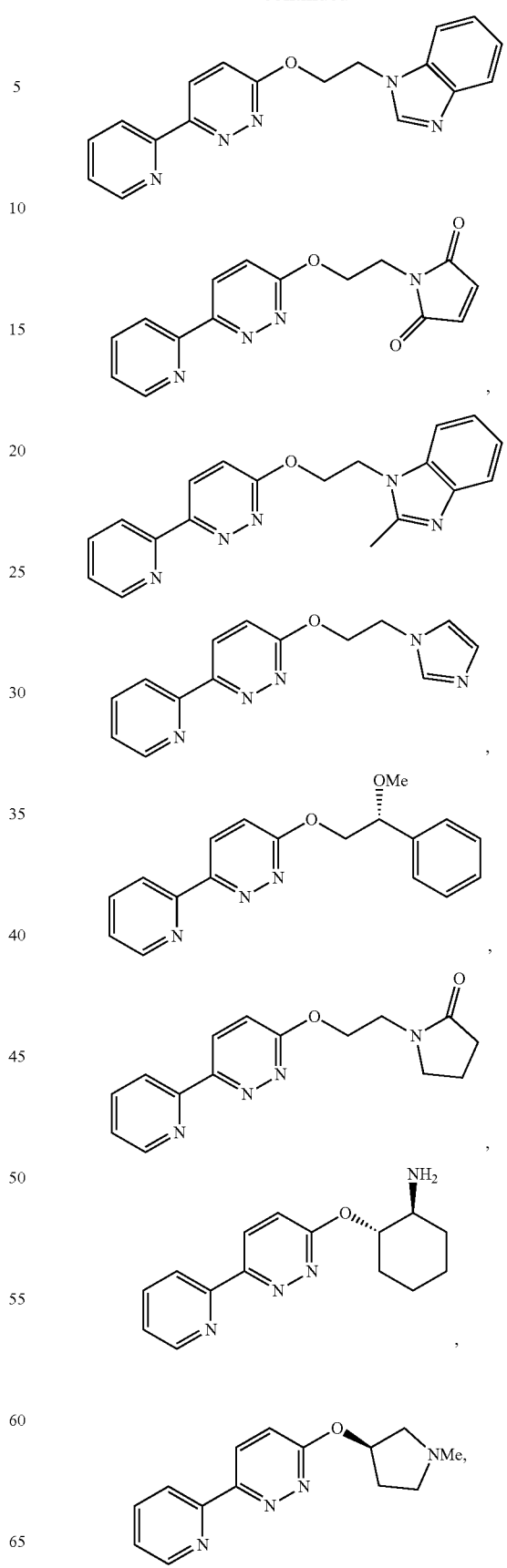

-continued
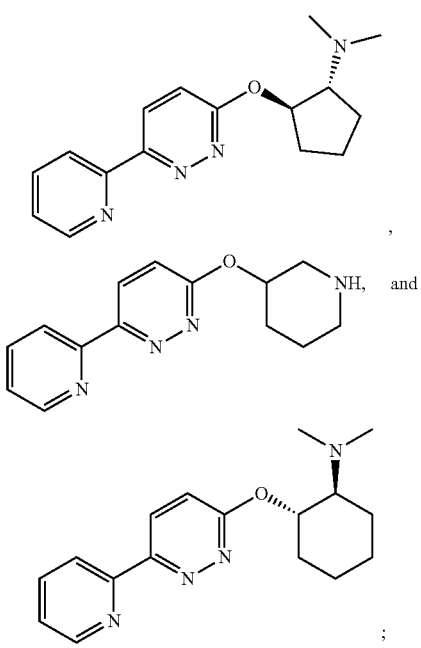
or a pharmaceutically acceptable salt thereof.
In some embodiments, the compound of Formula (II) or the compound of Formula (IIa) is selected from the group consisting of:
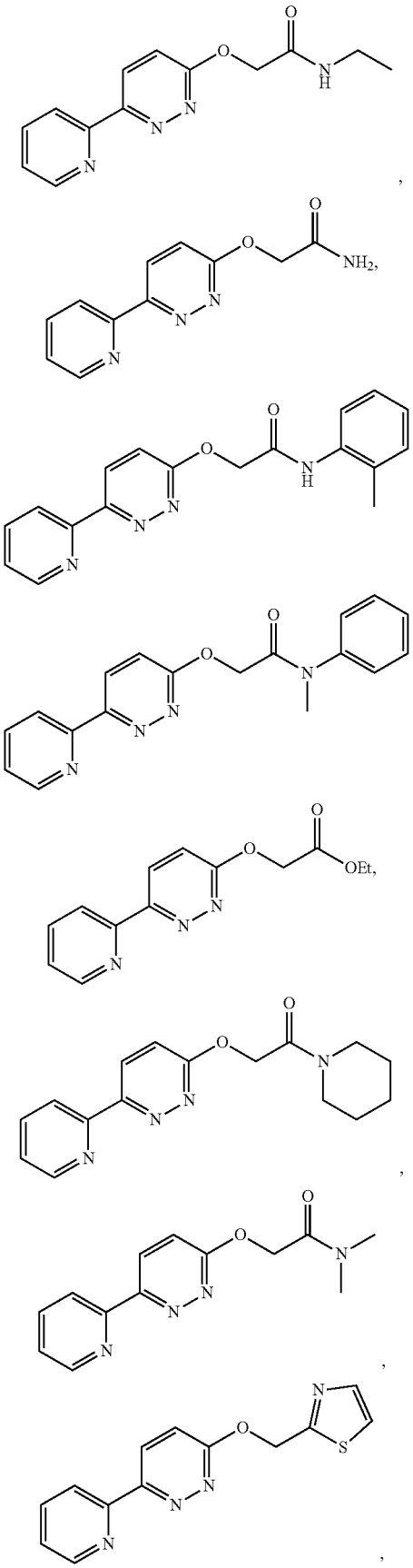

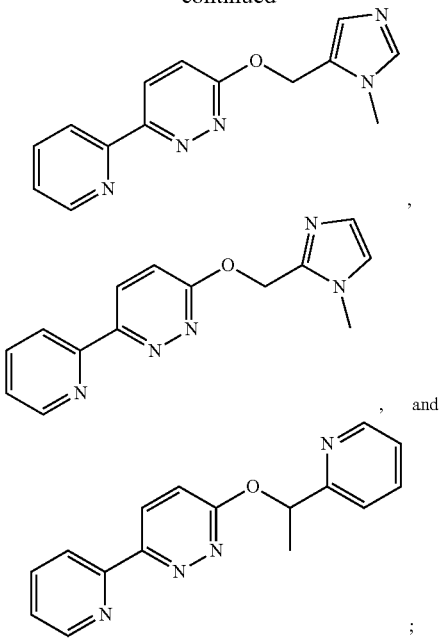

, and

; or a pharmaceutically acceptable salt thereof.

The present application further provides a compound of Formula (III):

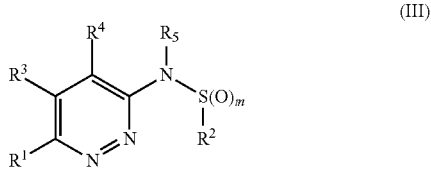

or a pharmaceutically acceptable salt thereof, wherein:

$R^1$ is selected from the group consisting of 6-10 membered aryl and 5-10 membered heteroaryl, each of which is optionally substituted by 1, 2, 3, or 4 independently selected $R^A$ groups;

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^3$, $R^4$, and $R^5$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and m is 1 or 2.

In some embodiments, $R^1$ is a 5-10 membered heteroaryl which is optionally substituted by 1, 2, 3, or 4 independently selected $R^A$ groups. In some embodiments, $R^1$ is an unsubstituted 5-10 membered heteroaryl. In some embodiments, $R^1$ is a 5-10 membered heteroaryl which is optionally substituted by 1 $R^A$ group. In some embodiments, $R^1$ is a 5-10 membered heteroaryl which is optionally substituted by 2 independently selected $R^A$ groups. In some embodiments, $R^1$ is a 5-10 membered heteroaryl which is optionally substituted by 3 independently selected $R^A$ groups. In some embodiments, $R^1$ is a 5-10 membered heteroaryl which is optionally substituted by 4 independently selected $R^A$ groups. In some embodiments, $R^1$ is pyridyl which is optionally substituted by 1, 2, 3, or 4 independently selected $R^A$ groups. In some embodiments, $R^1$ is unsubstituted pyridyl.

In some embodiments, $R^2$ is a 6-10 membered aryl which is optionally substituted by 1, 2, 3, or 4 independently selected $R^B$ groups. In some embodiments, $R^2$ is an unsubstituted 6-10 membered aryl. In some embodiments, $R^2$ is phenyl which is optionally substituted by 1, 2, 3, or 4 independently selected $R^B$ groups. In some embodiments, $R^2$ is an unsubstituted phenyl. In some embodiments, $R^2$ is phenyl which is optionally substituted by 1 $R^B$ group. In some embodiments, $R^2$ is phenyl which is optionally substituted by 2 independently selected $R^B$ groups. In some embodiments, $R^2$ is phenyl which is optionally substituted by 3 independently selected $R^B$ groups. In some embodiments, $R^2$ is phenyl which is optionally substituted by 4 independently selected $R^B$ groups.

In some embodiments, each $R^B$ is an independently selected halo group. In some embodiments, each $R^B$ is F.

In some embodiments, $R^3$ is H. In some embodiments, $R^4$ is H. In some embodiments, $R^3$ and $R^4$ are H. In some embodiments, $R^5$ is H. In some embodiments, $R^3$, $R^4$, and $R^5$ are H.

In some embodiments, m is 1. In some embodiments, m is 2.

In some embodiments, the compound of Formula (III) is a compound of Formula (IIIa):

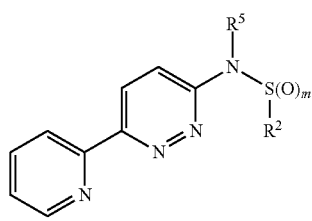

(IIIa)

or a pharmaceutically acceptable salt thereof, wherein:

$R^2$ is selected from the group consisting of 6-10 membered aryl, 5-10 membered heteroaryl, 4-10 membered heterocycloalkyl, each of which is optionally substituted by 1, 2, 3, or 4 independently selected $R^B$ groups;

$R^5$ is selected from H and $C_{1-6}$ alkyl;

each $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and m is 1 or 2.

In some embodiments, $R^2$ is a 6-10 membered aryl which is optionally substituted by 1, 2, 3, or 4 independently selected $R^B$ groups. In some embodiments, $R^2$ is an unsubstituted 6-10 membered aryl. In some embodiments, $R^2$ is phenyl which is optionally substituted by 1, 2, 3, or 4 independently selected $R^B$ groups. In some embodiments, $R^2$ is an unsubstituted phenyl. In some embodiments, $R^2$ is phenyl which is optionally substituted by 1 $R^B$ group. In some embodiments, $R^2$ is phenyl which is optionally substituted by 2 independently selected $R^B$ groups. In some embodiments, $R^2$ is phenyl which is optionally substituted by 3 independently selected $R^B$ groups. In some embodiments, $R^2$ is phenyl which is optionally substituted by 4 independently selected $R^B$ groups.

In some embodiments, each $R^B$ is an independently selected halo group. In some embodiments, each $R^B$ is F.

In some embodiments, $R^5$ is H.

In some embodiments, m is 1. In some embodiments, m is 2.

In some embodiments, the compound of Formula (III) or compound of Formula (IIIa) is selected from the group consisting of:

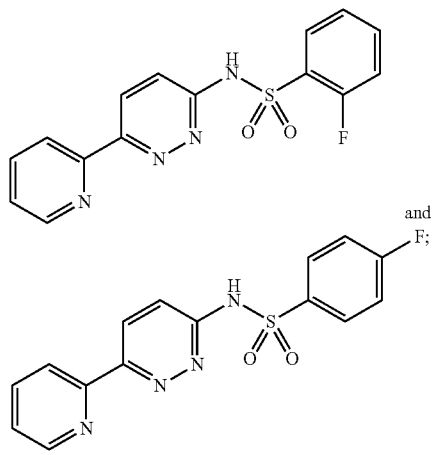

or a pharmaceutically acceptable salt thereof.

The present application further provides a compound of Formula (IV):

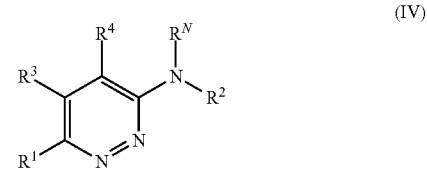

(IV)

or a pharmaceutically acceptable salt thereof, wherein:

$R^N$ is selected from the group consisting of H, $C_{1-6}$ alkyl, and $C(O)R^{N1}$;

$R^{N1}$ is a $C_{6-10}$ aryl which is optionally substituted by 1, 2, 3, or 4 independently selected halo groups;

$R^1$ is selected from the group consisting of 6-10 membered aryl and 5-10 membered heteroaryl, each of which is optionally substituted by 1, 2, 3, or 4 independently selected $R^A$ groups;

$R^2$ is —$(CHR^E)_nR^5$;

$R^5$ is selected from the group consisting of $NR^CR^D$, $C(O)NR^CR^D$, $C(O)OR^C$, $C_{3-10}$ cycloalkyl, $C_{6-10}$ aryl, 4-10 membered heterocycloalkyl, and 5-10 membered heteroaryl, wherein the $C_{3-10}$ cycloalkyl, $C_{6-10}$ aryl, 4-10 membered heterocycloalkyl, and 5-10 membered heteroaryl are each optionally substituted by 1, 2, 3, or 4 independently selected $R^B$ groups;

$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;

$R^3$ and $R^4$ are independently selected from H and $C_{1-6}$ alkyl;

each $R^A$ and $R^B$ is independently selected from halo, $C_{1-6}$ alkyl, $C_{2-6}$ alkenyl, $C_{2-6}$ alkynyl, $C_{1-4}$ haloalkyl, CN, $NO_2$, $OR^a$, $SR^a$, $C(O)R^b$, $C(O)NR^cR^d$, $C(O)OR^a$, $OC(O)R^b$, $OC(O)NR^cR^d$, $NR^cR^d$, $NR^cOR^d$, $NR^cC(O)R^b$, $NR^cC(O)$ $OR^a$, $NR^cC(O)NR^cR^d$, $C(=NR^e)R^b$, $C(=NR^e)NR^cR^d$, $NR^cC(=NR^e)NR^cR^d$, $NR^cS(O)R^b$, $NR^cS(O)_2R^b$, $NR^cS(O)_2NR^cR^d$, $S(O)R^b$, $S(O)NR^cR^d$, $S(O)_2R^b$, and $S(O)_2NR^cR^d$; wherein said $C_{1-6}$ alkyl, $C_{2-6}$ alkenyl, $C_{2-6}$ alkynyl, and $C_{1-4}$ haloalkyl are optionally substituted with 1, 2, 3, or 4 independently selected $R^6$ groups;

$R^C$ and $R^D$ are independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, 5-10 membered heteroaryl-$C_{1-4}$ alkylene; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, 4-10 membered heterocycloalkyl, $C_{3-10}$ cycloalkyl-$C_{1-4}$ alkylene, 4-10 membered heterocycloalkyl-$C_{1-4}$ alkylene, 6-10 membered aryl-$C_{1-4}$ alkylene, and 5-10 membered heteroaryl-$C_{1-4}$ alkylene are each optionally substituted with 1, 2, 3, or 4 independently selected $R^6$ groups; or alternatively, any $R^C$ and $R^D$ attached to the same N atom, together with the N atom to which they are attached, form a 4-6 membered heterocycloalkyl group or a 5-6 membered heteroaryl group, each optionally substituted with 1, 2, or 3 independently selected $R^6$ groups;

each $R^a$, $R^b$, $R^c$, and $R^d$ is independently selected from H, $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl; wherein the $C_{1-6}$ alkyl, $C_{2-6}$ alkenyl, $C_{2-6}$ alkynyl, $C_{1-4}$ haloalkyl, $C_{3-10}$ cycloalkyl, 6-10 membered aryl, 5-10 membered heteroaryl, and 4-10 membered heterocycloalkyl are each optionally substituted with 1, 2, 3, or 4 independently selected $R^6$ groups;

each $R^e$ is independently selected from H, CN, $C_{1-6}$ alkyl, $C_{1-6}$ haloalkyl, $C_{1-6}$ alkylthio, $C_{1-6}$ alkylsulfonyl, $C_{1-6}$ alkylcarbonyl, $C_{1-6}$ alkylaminosulfonyl, carbamyl, $C_{1-6}$ alkylcarbamyl, di($C_{1-6}$ alkyl)carbamyl, aminosulfonyl, $C_{1-6}$ alkylaminosulfonyl, and di($C_{1-6}$ alkyl)aminosulfonyl;

each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$ alkyl)aminocarbonylamino; and n is 0, 1, 2, 3, 4, or 5.

In some embodiments, $R^N$ is selected from the group consisting of H, $C_{1-6}$ alkyl, and $C(O)R^{N1}$, wherein $R^{N1}$ is a phenyl ring which is optionally substituted by 1, 2, 3, or 4 independently selected halo groups. In some embodiments, $R^N$ is selected from the group consisting of H, $C_{1-6}$ alkyl, and $C(O)R^{N1}$, wherein $R^{N1}$ is a phenyl ring which is optionally substituted by 1 or two independently selected halo groups. In some embodiments, $R^N$ is selected from the group consisting of H, $C_{1-3}$ alkyl, and $C(O)R^{N1}$, wherein $R^{N1}$ is a phenyl ring which is optionally substituted by 1 or 2 fluoro groups. In some embodiments, $R^N$ is selected from the group consisting of H, methyl, C(O)phenyl, and C(O)(4-fluorophenyl).

In some embodiments, $R^1$ is selected from the group consisting of phenyl and 5-6 membered heteroaryl, each of which is optionally substituted by 1, 2, 3, or 4 independently selected $R^A$ groups. In some embodiments, $R^1$ is a 5-6 membered heteroaryl, which is optionally substituted by 1, 2, 3, or 4 independently selected $R^A$ groups. In some embodiments, $R^1$ is an unsubstituted 5-6 membered heteroaryl. In some embodiments, $R^1$ is pyridyl.

In some embodiments, $R^2$ is —$(CH_2)_nR^5$. In some embodiments, n is 0, 1, 2, or 3. In some embodiments, n is 1, 2, or 3. In some embodiments, n is 0. In some embodiments, n is 1. In some embodiments, n is 2. In some embodiments, n is 3. In some embodiments, n is 4. In some embodiments, n is 5.

In some embodiments, $R^3$ is H. In some embodiments, $R^4$ is H. In some embodiments, $R^3$ and $R^4$ are each H.

In some embodiments, $R^5$ is selected from the group consisting of $NR^CR^D$, $C_{6-10}$ aryl, and 5-10 membered heteroaryl, wherein the $C_{6-10}$ aryl and 5-10 membered heteroaryl are each optionally substituted by 1, 2, 3, or 4 independently selected $R^B$ groups. In some embodiments, $R^5$ is selected from the group consisting of $NR^CR^D$, phenyl, and 5-6 membered heteroaryl, wherein the phenyl and 5-6 membered heteroaryl are each optionally substituted by 1, 2, 3, or 4 independently selected $R^B$ groups. In some embodiments, $R^5$ is selected from the group consisting of $NR^CR^D$, unsubstituted phenyl, and unsubstituted 5-6 membered heteroaryl. In some embodiments, $R^5$ is selected from the group consisting of $N(CH_3)_2$, unsubstituted phenyl, and unsubstituted imidazolyl.

In some embodiments, $R^C$ is selected from the group consisting of H, $C_{1-6}$ alkyl, $C_{2-6}$ alkenyl, $C_{2-6}$ alkynyl, $C_{1-4}$ haloalkyl. In some embodiments, $R^C$ is selected from the group consisting of H and $C_{1-6}$ alkyl. In some embodiments, $R^C$ is $C_{1-4}$ alkyl. In some embodiments, $R^C$ is methyl. In some embodiments, $R^D$ is selected from the group consisting of H, $C_{1-6}$ alkyl, $C_{2-6}$ alkenyl, $C_{2-6}$ alkynyl, $C_{1-4}$ haloalkyl. In some embodiments, $R^D$ is selected from the group consisting of H and $C_{1-6}$ alkyl. In some embodiments, $R^D$ is $C_{1-4}$ alkyl. In some embodiments, $R^D$ is methyl. In some embodiments, $R^C$ and $R^D$ are each methyl.

In some embodiments:

$R^N$ is selected from the group consisting of H, $C_{1-6}$ alkyl, and $C(O)R^{N1}$, wherein $R^{N1}$ is a phenyl ring which is optionally substituted by 1, 2, 3, or 4 independently selected halo groups;

$R^1$ is selected from the group consisting of phenyl and 5-6 membered heteroaryl, each of which is optionally substituted by 1, 2, 3, or 4 independently selected $R^A$ groups;

$R^2$ is —$(CH_2)_nR^5$;

$R^5$ is selected from the group consisting of $NR^CR^D$, $C_{6-10}$ aryl, and 5-10 membered heteroaryl, wherein the $C_{6-10}$ aryl and 5-10 membered heteroaryl are each optionally substituted by 1, 2, 3, or 4 independently selected $R^B$ groups;

$R^C$ is selected from the group consisting of H, $C_{1-6}$ alkyl, $C_{2-6}$ alkenyl, $C_{2-6}$ alkynyl, $C_{1-4}$ haloalkyl;

$R^D$ is selected from the group consisting of H, $C_{1-6}$ alkyl, $C_{2-6}$ alkenyl, $C_{2-6}$ alkynyl, $C_{1-4}$ haloalkyl; and n is 1, 2, or 3.

In some embodiments:

$R^N$ is selected from the group consisting of H, $C_{1-6}$ alkyl, and $C(O)R^{N1}$, wherein $R^{N1}$ is a phenyl ring which is optionally substituted by 1 or 2 or two independently selected halo groups;

$R^1$ is an unsubstituted 5-6 membered heteroaryl;
$R^2$ is —$(CH_2)_nR^5$;
$R^3$ and $R^4$ are each H;
$R^5$ is selected from the group consisting of $NR^CR^D$, unsubstituted phenyl, and unsubstituted 5-6 membered heteroaryl;
$R^C$ is selected from the group consisting of H and $C_{1-6}$ alkyl;
$R^D$ is selected from the group consisting of H and $C_{1-6}$ alkyl; and
n is 1, 2, or 3.

In some embodiments:
$R^N$ is selected from the group consisting of H, $C_{1-3}$ alkyl, and $C(O)R^{N1}$, wherein $R^{N1}$ is a phenyl ring which is optionally substituted by 1 or 2 fluoro groups;
$R^1$ is an unsubstituted pyridyl;
$R^2$ is —$(CH_2)_nR^5$;
$R^3$ and $R^4$ are each H;
$R^5$ is selected from the group consisting of $NR^CR^D$, unsubstituted phenyl, and unsubstituted 5-6 membered heteroaryl;
$R^C$ is selected from the group consisting of H and $C_{1-6}$ alkyl;
$R^D$ is selected from the group consisting of H and $C_{1-6}$ alkyl; and
n is 1, 2, or 3.

In some embodiments, the compound of Formula (IV) is a compound of Formula (IVa):

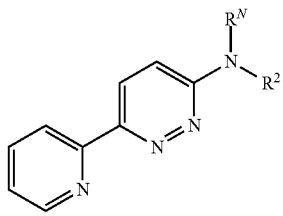

(IVa)

or a pharmaceutically acceptable salt thereof, wherein variables $R^2$ and $R^N$ are defined according to the definitions provided herein for compounds of Formula IV.

In some embodiments, the compound of Formula (IV) or compound of Formula (IVa) is selected from the group consisting of:

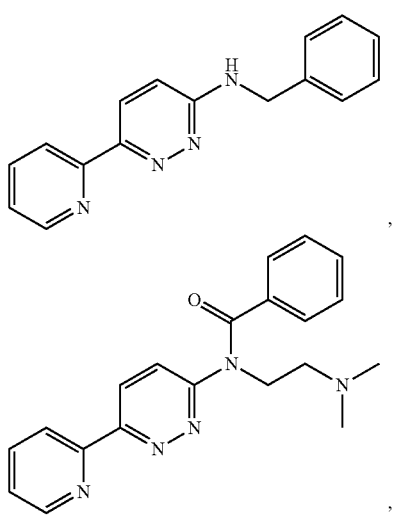

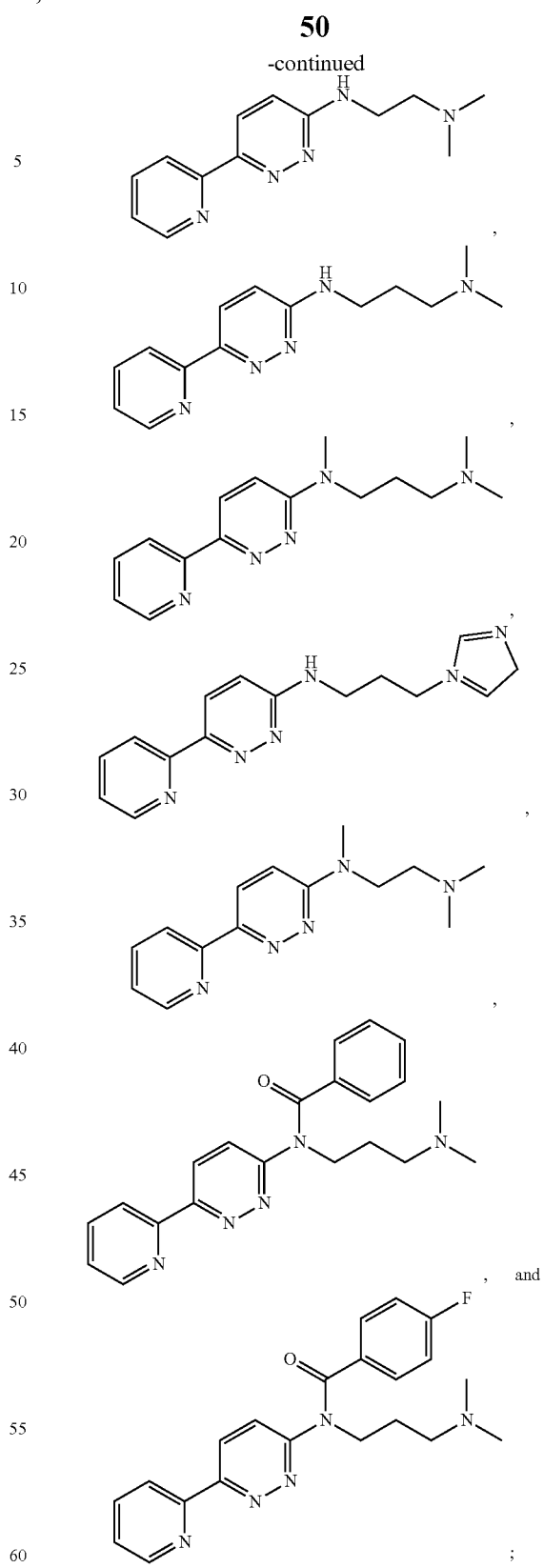

or a pharmaceutically acceptable salt thereof.

Synthesis

As will be appreciated, the compounds provided herein (e.g., compounds of Formula (I), compounds of Formula (Ia), compounds of Formula (II), compounds of Formula (IIa), compounds of Formula (III), compounds of Formula (IIIa) compounds of Formula (IV), and Formula (IVa)), including salts thereof, can be prepared using known organic synthesis techniques and can be synthesized according to any of numerous possible synthetic routes.

Compounds of Formula (I) and compounds of Formula (Ia) may be prepared, for example, according to the procedure shown in Scheme 1. An amine-substituted piperazine (i) can be reacted with carboxylic acid (ii) in the presence of a C—N coupling agent and a base (e.g., 1-[bis-(dimethylamino)methylene]-1H-1,2,3-triazolo[4,5-b]pyridinium 3-oxid hexafluorophosphate (HATU) and N,N-diisopropylethylamine) to form the amide-substituted piperazine analog (iii).

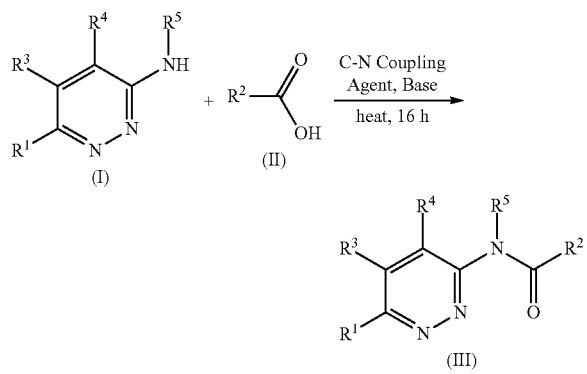

Compounds of Formula (II) and compounds of Formula (IIa) may be prepared, for example, according to the procedure shown in Scheme 2. A halo-substituted piperazine (iv) (where $X^1$ is halo, e.g., chloro, bromo, or iodo) can be reacted with alcohol (v) in the presence of a base (e.g., sodium tert-butoxide) to form the ether-substituted piperazine analog (vi).

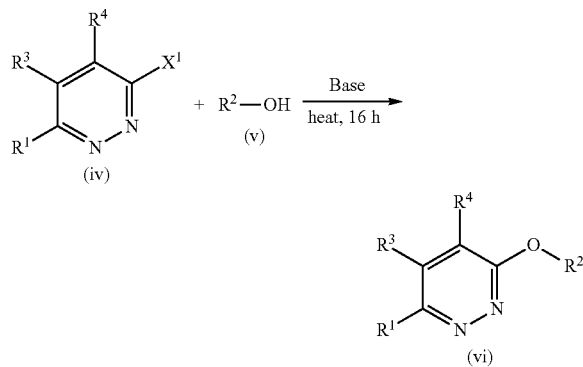

Compounds of Formula (IV) and compounds of Formula (IVa) may be prepared, for example, according to the procedure shown in Scheme 3. For example, a halo substituted piperazine (vii) (where $X^1$ is halo, e.g., chloro, bromo, or iodo) can be reacted with an appropriately substituted amine (viii) (e.g., in the presence of KEIMDS and Brett-phos, or ammonium chloride) and heated to form the amine-substituted piperazine analog (ix).

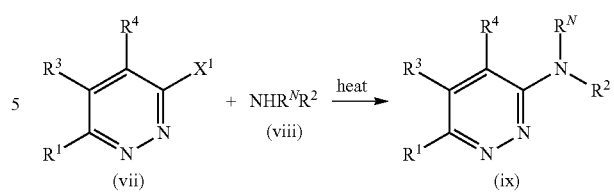

It will be appreciated by one skilled in the art that the processes described are not the exclusive means by which compounds provided herein may be synthesized and that a broad repertoire of synthetic organic reactions is available to be potentially employed in synthesizing compounds provided herein. The person skilled in the art knows how to select and implement appropriate synthetic routes. Suitable synthetic methods of starting materials, intermediates and products may be identified by reference to the literature, including reference sources such as: *Advances in Heterocyclic Chemistry*, Vols. 1-107 (Elsevier, 1963-2012); *Journal of Heterocyclic Chemistry* Vols. 1-49 (Journal of Heterocyclic Chemistry, 1964-2012); Carreira, et al. (Ed.) *Science of Synthesis*, Vols. 1-48 (2001-2010) and Knowledge Updates KU2010/1-4; 2011/1-4; 2012/1-2 (Thieme, 2001-2012); Katritzky, et al. (Ed.) *Comprehensive Organic Functional Group Transformations*, (Pergamon Press, 1996); Katritzky et al. (Ed.); *Comprehensive Organic Functional Group Transformations II* (Elsevier, $2^{nd}$ Edition, 2004); Katritzky et al. (Ed.), *Comprehensive Heterocyclic Chemistry* (Pergamon Press, 1984); Katritzky et al., *Comprehensive Heterocyclic Chemistry II*, (Pergamon Press, 1996); Smith et al., *March's Advanced Organic Chemistry: Reactions, Mechanisms, and Structure*, $6^{th}$ Ed. (Wiley, 2007); Trost et al. (Ed.), *Comprehensive Organic Synthesis* (Pergamon Press, 1991).

The reactions for preparing compounds described herein can be carried out in suitable solvents which can be readily selected by one of skill in the art of organic synthesis. Suitable solvents can be substantially non-reactive with the starting materials (reactants), the intermediates, or products at the temperatures at which the reactions are carried out, (e.g., temperatures which can range from the solvent's freezing temperature to the solvent's boiling temperature). A given reaction can be carried out in one solvent or a mixture of more than one solvent. Depending on the particular reaction step, suitable solvents for a particular reaction step can be selected by the skilled artisan.

Preparation of compounds described herein can involve the protection and deprotection of various chemical groups. The need for protection and deprotection, and the selection of appropriate protecting groups, can be readily determined by one skilled in the art. The chemistry of protecting groups can be found, for example, in T. W. Greene and P. G. M. Wuts, *Protective Groups in Organic Synthesis*, $3^{rd}$ Ed., Wiley & Sons, Inc., New York (1999).

Reactions can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatographic methods such as high performance liquid chromatography (HPLC), liquid chromatography-mass spectroscopy (LCMS), or thin layer chromatography (TLC). Compounds can be purified by those skilled in the art by a variety of methods, including high performance liquid chromatography (HPLC) and normal phase silica chromatography.

At various places in the present specification, divalent linking substituents are described. Where the structure clearly requires a linking group, the Markush variables listed for that group are understood to be linking groups.

The term "n-membered" where n is an integer typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring, and 1,2,3,4-tetrahydro-naphthalene is an example of a 10-membered cycloalkyl group.

As used herein, the phrase "optionally substituted" means unsubstituted or substituted. As used herein, the term "substituted" means that a hydrogen atom is removed and replaced by a substituent. It is to be understood that substitution at a given atom is limited by valency.

Throughout the definitions, the term "$C_{n-m}$" indicates a range which includes the endpoints, wherein n and m are integers and indicate the number of carbons. Examples include $C_{1-4}$, $C_{1-6}$, and the like.

As used herein, the term "$C_{n-m}$ alkyl", employed alone or in combination with other terms, refers to a saturated hydrocarbon group that may be straight-chain or branched, having n to m carbons. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl, and the like. In some embodiments, the alkyl group contains from 1 to 6 carbon atoms, from 1 to 4 carbon atoms, from 1 to 3 carbon atoms, or 1 to 2 carbon atoms.

As used herein, "$C_{n-m}$ alkenyl" refers to an alkyl group having one or more double carbon-carbon bonds and having n to m carbons. Example alkenyl groups include, but are not limited to, ethenyl, n-propenyl, isopropenyl, n-butenyl, sec-butenyl, and the like. In some embodiments, the alkenyl moiety contains 2 to 6, 2 to 4, or 2 to 3 carbon atoms.

As used herein, "$C_{n-m}$ alkynyl" refers to an alkyl group having one or more triple carbon-carbon bonds and having n to m carbons. Example alkynyl groups include, but are not limited to, ethynyl, propyn-1-yl, propyn-2-yl, and the like. In some embodiments, the alkynyl moiety contains 2 to 6, 2 to 4, or 2 to 3 carbon atoms.

As used herein, the term "$C_{n-m}$ alkylene", employed alone or in combination with other terms, refers to a divalent alkyl linking group having n to m carbons. Examples of alkylene groups include, but are not limited to, ethan-1,2-diyl, propan-1,3-diyl, propan-1,2-diyl, butan-1,4-diyl, butan-1,3-diyl, butan-1,2-diyl, 2-methyl-propan-1,3-diyl, and the like. In some embodiments, the alkylene moiety contains 2 to 6, 2 to 4, 2 to 3, 1 to 6, 1 to 4, or 1 to 2 carbon atoms.

As used herein, the term "$C_{n-m}$ alkoxy", employed alone or in combination with other terms, refers to a group of formula —O-alkyl, wherein the alkyl group has n to m carbons. Example alkoxy groups include methoxy, ethoxy, propoxy (e.g., n-propoxy and isopropoxy), tert-butoxy, and the like. In some embodiments, the alkyl group has 1 to 6, 1 to 4, or 1 to 3 carbon atoms.

As used herein, the term "$C_{n-m}$ alkylamino" refers to a group of formula —NH(alkyl), wherein the alkyl group has n to m carbon atoms. In some embodiments, the alkyl group has 1 to 6, 1 to 4, or 1 to 3 carbon atoms.

As used herein, the term "$C_{n-m}$ alkoxycarbonyl" refers to a group of formula —C(O)O-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonyl" refers to a group of formula —C(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylcarbonylamino" refers to a group of formula —NHC(O)-alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonylamino" refers to a group of formula —NHS(O)$_2$-alkyl, wherein the alkyl group has n to m carbon atoms. In some embodiments, the alkyl group has 1 to 6, 1 to 4, or 1 to 3 carbon atoms.

As used herein, the term "aminosulfonyl" refers to a group of formula —S(O)$_2$NH$_2$.

As used herein, the term "$C_{n-m}$ alkylaminosulfonyl" refers to a group of formula —S(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonyl" refers to a group of formula —S(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminosulfonylamino" refers to a group of formula —NHS(O)$_2$NH$_2$.

As used herein, the term "$C_{n-m}$ alkylaminosulfonylamino" refers to a group of formula —NHS(O)$_2$NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminosulfonylamino" refers to a group of formula —NHS(O)$_2$N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "aminocarbonylamino", employed alone or in combination with other terms, refers to a group of formula —NHC(O)NH$_2$.

As used herein, the term "$C_{n-m}$ alkylaminocarbonylamino" refers to a group of formula —NHC(O)NH(alkyl), wherein the alkyl group has n to m carbon atoms. In some embodiments, the alkyl group has 1 to 6, 1 to 4, or 1 to 3 carbon atoms.

As used herein, the term "di($C_{n-m}$ alkyl)aminocarbonylamino" refers to a group of formula —NHC(O)N(alkyl)$_2$, wherein each alkyl group independently has n to m carbon atoms. In some embodiments, each alkyl group has, independently, 1 to 6, 1 to 4, or 1 to 3 carbon atoms.

As used herein, the term "$C_{n-m}$ alkylcarbamyl" refers to a group of formula —C(O)—NH(alkyl), wherein the alkyl group has n to m carbon atoms. In some embodiments, the alkyl group has 1 to 6, 1 to 4, or 1 to 3 carbon atoms.

As used herein, the term "thio" refers to a group of formula —SH.

As used herein, the term "$C_{n-m}$ alkylsulfinyl" refers to a group of formula —S(O)— alkyl, wherein the alkyl group has n to m carbon atoms. In some embodiments, the alkyl group has 1 to 6, 1 to 4, or 1 to 3 carbon atoms.

As used herein, the term "$C_{n-m}$ alkylsulfonyl" refers to a group of formula —S(O)$_2$-alkyl, wherein the alkyl group has n to m carbon atoms. In some embodiments, the alkyl group has 1 to 6, 1 to 4, or 1 to 3 carbon atoms.

As used herein, the term "amino" refers to a group of formula NH$_2$.

As used herein, the term "aryl," employed alone or in combination with other terms, refers to an aromatic hydrocarbon group, which may be monocyclic or polycyclic (e.g., having 2, 3 or 4 fused rings). The term "$C_{n-m}$ aryl" refers to an aryl group having from n to m ring carbon atoms. Aryl groups include, e.g., phenyl, naphthyl, anthracenyl, phenanthrenyl, indanyl, indenyl, and the like. In some embodiments, aryl groups have from 6 to about 20 carbon atoms, from 6 to about 15 carbon atoms, or from 6 to about 10 carbon atoms. In some embodiments, the aryl group is a substituted or unsubstituted phenyl.

As used herein, the term "carbamyl" to a group of formula $C(O)NH_2$.

As used herein, the term "carbonyl", employed alone or in combination with other terms, refers to a —C(=O)— group, which may also be written as C(O).

As used herein, the term "di($C_{n-m}$-alkyl)amino" refers to a group of formula —N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "di($C_{n-m}$-alkyl)carbamyl" refers to a group of formula —C(O)N(alkyl)$_2$, wherein the two alkyl groups each has, independently, n to m carbon atoms. In some embodiments, each alkyl group independently has 1 to 6, 1 to 4, or 1 to 3 carbon atoms.

As used herein, the term "halo" refers to F, Cl, Br, or I. In some embodiments, a halo is F, Cl, or Br. In some embodiments, a halo is F or Cl.

As used herein, "$C_{n-m}$ haloalkoxy" refers to a group of formula —O-haloalkyl having n to m carbon atoms. An example haloalkoxy group is $OCF_3$. In some embodiments, the haloalkoxy group is fluorinated only. In some embodiments, the alkyl group has 1 to 6, 1 to 4, or 1 to 3 carbon atoms.

As used herein, the term "$C_{n-m}$ haloalkyl", employed alone or in combination with other terms, refers to an alkyl group having from one halogen atom to 2s+1 halogen atoms which may be the same or different, where "s" is the number of carbon atoms in the alkyl group, wherein the alkyl group has n to m carbon atoms. In some embodiments, the haloalkyl group is fluorinated only. In some embodiments, the alkyl group has 1 to 6, 1 to 4, or 1 to 3 carbon atoms.

As used herein, "cycloalkyl" refers to non-aromatic cyclic hydrocarbons including cyclized alkyl and/or alkenyl groups. Cycloalkyl groups can include mono- or polycyclic (e.g., having 2, 3 or 4 fused rings) groups and spirocycles. Cycloalkyl groups can have 3, 4, 5, 6, 7, 8, 9, or 10 ring-forming carbons ($C_{3-10}$). Ring-forming carbon atoms of a cycloalkyl group can be optionally substituted by oxo or sulfido (e.g., C(O) or C(S)). Cycloalkyl groups also include cycloalkylidenes. Example cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, and the like. In some embodiments, cycloalkyl is cyclopropyl, cyclobutyl, cyclopentyl, cyclohexyl, cyclopentyl, or adamantyl. In some embodiments, the cycloalkyl has 6-10 ring-forming carbon atoms. In some embodiments, cycloalkyl is adamantyl. Also included in the definition of cycloalkyl are moieties that have one or more aromatic rings fused (i.e., having a bond in common with) to the cycloalkyl ring, for example, benzo or thienyl derivatives of cyclopentane, cyclohexane, and the like. A cycloalkyl group containing a fused aromatic ring can be attached through any ring-forming atom including a ring-forming atom of the fused aromatic ring.

As used herein, "heteroaryl" refers to a monocyclic or polycyclic aromatic heterocycle having at least one heteroatom ring member selected from sulfur, oxygen, and nitrogen. In some embodiments, the heteroaryl ring has 1, 2, 3, or 4 heteroatom ring members independently selected from nitrogen, sulfur and oxygen. In some embodiments, any ring-forming N in a heteroaryl moiety can be an N-oxide. In some embodiments, the heteroaryl has 5-10 ring atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. A five-membered heteroaryl ring is a heteroaryl with a ring having five ring atoms wherein one or more (e.g., 1, 2, or 3) ring atoms are independently selected from N, O, and S. Exemplary five-membered ring heteroaryls are thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl, and 1,3,4-oxadiazolyl. A six-membered heteroaryl ring is a heteroaryl with a ring having six ring atoms wherein one or more (e.g., 1, 2, or 3) ring atoms are independently selected from N, O, and S. Exemplary six-membered ring heteroaryls are pyridyl, pyrazinyl, pyrimidinyl, triazinyl and pyridazinyl.

As used herein, "heterocycloalkyl" refers to non-aromatic monocyclic or polycyclic heterocycles having one or more ring-forming heteroatoms selected from O, N, or S. Included in heterocycloalkyl are monocyclic 4-, 5-, 6-, and 7-membered heterocycloalkyl groups. Heterocycloalkyl groups can also include spirocycles. Example heterocycloalkyl groups include pyrrolidin-2-one, 1,3-isoxazolidin-2-one, pyranyl, tetrahydropuran, oxetanyl, azetidinyl, morpholino, thiomorpholino, piperazinyl, tetrahydrofuranyl, tetrahydrothienyl, piperidinyl, pyrrolidinyl, isoxazolidinyl, isothiazolidinyl, pyrazolidinyl, oxazolidinyl, thiazolidinyl, imidazolidinyl, azepanyl, benzazapene, and the like. Ring-forming carbon atoms and heteroatoms of a heterocycloalkyl group can be optionally substituted by oxo or sulfido (e.g., C(O), S(O), C(S), or S(O)$_2$, etc.). The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the cycloalkyl ring, for example, benzo or thienyl derivatives of piperidine, morpholine, azepine, etc. A heterocycloalkyl group containing a fused aromatic ring can be attached through any ring-forming atom including a ring-forming atom of the fused aromatic ring. In some embodiments, the heterocycloalkyl has 4-10, 4-7 or 4-6 ring atoms with 1 or 2 heteroatoms independently selected from nitrogen, oxygen, or sulfur and having one or more oxidized ring members.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas a pyridin-3-yl ring is attached at the 3-position.

The term "compound" as used herein is meant to include all stereoisomers, geometric isomers, tautomers, and isotopes of the structures depicted. Compounds herein identified by name or structure as one particular tautomeric form are intended to include other tautomeric forms unless otherwise specified.

Compounds provided herein also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge. Example prototropic tautomers include ketone-enol pairs, amide-imidic acid pairs, lactam-lactim pairs, enamine-imine pairs, and annular forms where a proton can occupy two or more positions of a heterocyclic system, for example, 1H- and 3H-imidazole, 1H-, 2H- and 4H-1,2,4-triazole, 1H- and 2H-isoindole, and 1H- and 2H-pyrazole. Tautomeric forms can be in equilibrium or sterically locked into one form by appropriate substitution.

In some embodiments, the compounds described herein can contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms can be present in a substituent, such as an alkyl group. All such isomeric forms, as well as mixtures thereof, of these compounds are expressly included in the present description. The compounds described herein can also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present description. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, NY, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that the compounds described herein include all possible regioisomers, and mixtures thereof, which can be obtained in pure form by standard separation procedures known to those skilled in the art, and include, but are not limited to, column chromatography, thin-layer chromatography, and high-performance liquid chromatography.

Unless specifically defined, compounds provided herein can also include all isotopes of atoms occurring in the intermediates or final compounds. Isotopes include those atoms having the same atomic number but different mass numbers. Unless otherwise stated, when an atom is designated as an isotope or radioisotope (e.g., deuterium, [$^{11}$C], [$^{18}$F]), the atom is understood to comprise the isotope or radioisotope in an amount at least greater than the natural abundance of the isotope or radioisotope. For example, when an atom is designated as "D" or "deuterium", the position is understood to have deuterium at an abundance that is at least 3000 times greater than the natural abundance of deuterium, which is 0.015% (i.e., at least 45% incorporation of deuterium).

All compounds, and pharmaceutically acceptable salts thereof, can be found together with other substances such as water and solvents (e.g. hydrates and solvates) or can be isolated.

In some embodiments, preparation of compounds can involve the addition of acids or bases to affect, for example, catalysis of a desired reaction or formation of salt forms such as acid addition salts.

Example acids can be inorganic or organic acids and include, but are not limited to, strong and weak acids. Some example acids include hydrochloric acid, hydrobromic acid, sulfuric acid, phosphoric acid, p-toluenesulfonic acid, 4-nitrobenzoic acid, methanesulfonic acid, benzenesulfonic acid, trifluoroacetic acid, and nitric acid. Some weak acids include, but are not limited to acetic acid, propionic acid, butanoic acid, benzoic acid, tartaric acid, pentanoic acid, hexanoic acid, heptanoic acid, octanoic acid, nonanoic acid, and decanoic acid.

Example bases include lithium hydroxide, sodium hydroxide, potassium hydroxide, lithium carbonate, sodium carbonate, potassium carbonate, and sodium bicarbonate. Some example strong bases include, but are not limited to, hydroxide, alkoxides, metal amides, metal hydrides, metal dialkylamides and arylamines, wherein; alkoxides include lithium, sodium and potassium salts of methyl, ethyl and t-butyl oxides; metal amides include sodium amide, potassium amide and lithium amide; metal hydrides include sodium hydride, potassium hydride and lithium hydride; and metal dialkylamides include lithium, sodium, and potassium salts of methyl, ethyl, n-propyl, iso-propyl, n-butyl, tert-butyl, trimethylsilyl and cyclohexyl substituted amides.

In some embodiments, the compounds provided herein, or salts thereof, are substantially isolated. By "substantially isolated" is meant that the compound is at least partially or substantially separated from the environment in which it was formed or detected. Partial separation can include, for example, a composition enriched in the compounds provided herein. Substantial separation can include compositions containing at least about 50%, at least about 60%, at least about 70%, at least about 80%, at least about 90%, at least about 95%, at least about 97%, or at least about 99% by weight of the compounds provided herein, or salt thereof. Methods for isolating compounds and their salts are routine in the art.

The expressions, "ambient temperature" and "room temperature" or "rt" as used herein, are understood in the art, and refer generally to a temperature, e.g. a reaction temperature, that is about the temperature of the room in which the reaction is carried out, for example, a temperature from about 20° C. to about 30° C.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The present application also includes pharmaceutically acceptable salts of the compounds described herein. As used herein, "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present application include the conventional non-toxic salts of the parent compound formed, for example, from non-toxic inorganic or organic acids. The pharmaceutically acceptable salts of the present application can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol, or butanol) or acetonitrile (MeCN) are preferred. Lists of suitable salts are found in *Remington's Pharmaceutical Sciences,* 17th ed., Mack Publishing Company, Easton, Pa., 1985, p. 1418 and *Journal of Pharmaceutical Science,* 66, 2 (1977). Conventional methods for preparing salt forms are described, for example, in *Handbook of Pharmaceutical Salts: Properties, Selection, and Use,* Wiley-VCH, 2002.

Methods of Use

The present application further provides methods for the treatment of disorders associated with glutamate excitotoxicity in a subject in need thereof. A number of such disorders are known in the art, and can be readily identified by one of skill in the art. In some embodiments, the methods is a method for treating or preventing glutamate excitotoxicity in a subject in need thereof, the method comprising administering to the subject a therapeutically effective amount of a compound provided herein (e.g., a compound of Formula (I), a compound of Formula (Ia), a compound of Formula (II), a compound of Formula (IIa), a compound of Formula (III), or a compound of Formula (IIIa)), or a pharmaceutically acceptable salt thereof. As used herein, the term "subject," refers to any animal, including mammals. For example, the term "subject" includes, but is not limited to, mice, rats, other rodents, rabbits, dogs, cats, swine, cattle, sheep, horses, primates, and humans. In some embodiments, the subject is a human.

In some embodiments, the methods described herein can include in vitro methods, e.g., contacting a sample (e.g., a cell or tissue) with a compound provided herein, or a pharmaceutically acceptable salt thereof.

In some embodiments, the disorder is an acute neurological condition such as ischemic stroke, epilepsy, hypoglycemia, hypoxia, or trauma (see e.g., J. Neurosci. 2016 Oct. 12; 36(41):10529-10544; J. Clin. Invest. 2014 March; 124(3): 1255-67; and Neurochem. Int. 2006 April; 48(5):394-403).

In some embodiments, the disorder is a chronic neurodegenerative disorder such as Parkinson's disease, Alzheimer's disease, multiple sclerosis, mesial temporal sclerosis, Huntington's disease, AIDS dementia complex, or amyotrophic lateral sclerosis (ALS) (see, e.g., Hu et al., "Glutamate receptors in preclinical research on Alzheimer's disease: Update on recent advances." Pharmacol Biochem Behav. 2011 Apr. 22 [Epub ahead of print, doi:10.1016/j.pbb.2011.04.013]; Wang and Qin, Apoptosis. 15(11):1382-402 (2010); Kaul and Lipton, Curr HIV Res. 4(3):307-18 (2006); Kim et al., J Cell Physiol. 226(10):2484-93 (2011); Sheldon and Robinson, Neurochem Int. 51(6-7):333-55 (2007); Guo et al., Hum. Mol. Genet. 2003, 12, 2519; Tian et al., J. Biol. Chem. 282:1727 (2007); Hazell, Neurochem. Int. 50:941 (2007); Seifert et al., Brain. Res. Rev.63:212 (2010); Tian et al., J. Neurochem. 113:978 (2010); Olney, "Neurotoxicity of excitatory amino acids." In: McGeer E, Olney J, McGeer P, eds. *Kainic Acid as a Tool in Neurobiology*. New York: Raven Press; 1978:95-121; Olney, APMIS Suppl 40:103-112 (2010); J. Exp. Med. 2015 Mar. 9; 212 (3):319-32; Neurobiol. Aging. 2015 July; 36(7):2260-71; Neural. Plast. 2016; 2016:8941327; PLoS One. 2008 Sep. 5; 3(9):e3149; J. Clin. Invest. 2014 March; 124(3):1255-67; J. Neurochem. 2012 May; 121(4):629-38; and Curr. HIV Res. 2012 July; 10(5):392-406).

In some embodiments, the disorder is depression (see, e.g., Chen et al., Presynaptic glutamatergic dysfunction in bipolar disorder, Biol. Pshychiatry, 67(11): 1007-1009 (2010)).

In some embodiments, glutamate excitotoxicity can be a result of an environmental toxin, e.g., Tributyltin (Nakatsu et al., Toxicol. Sci. (January 2006) 89 (1): 235-242), lead, and domoic acid.

In some embodiments, excessive glutamate is associated with chronic pain disorders including migraine, fibromyalgia, temporomandibular disorders, neuropathic pain, visceral pain, or complex regional pain syndrome (see, e.g., Chizh et al., Amino Acids, 23(1-3):169-76 (2002); Descalzi et al., Mol Neurobiol. 40(3):253-9. Epub 2009 Oct. 11 (2009); Larsson, Mol Neurobiol. 40(3):260-88 (2009); Yogeswaari et al., Expert Opin Ther Targets. 13(8):925-43 (2009); Vargas, Curr Pain Headache Rep. 13(1):64-6 (2009); Adv. Pharmacol. 2016; 75:245-71; J. Neurochem. 2014 December; 131(6):712-30; Eurasian J Med. 2011 December; 43(3):182-5; and J. Pharmacol. Sci. 2010; 114(4):347-53).

Disruptions in glutamate homeostasis are associated with addictive disorders. As substance abuse develops into addiction, neurochemistry shifts from dopamine-based to predominantly glutamate-based. Thus, subjects suffering from drug addiction and dependence, including alcohol and cocaine addiction, can also be treated using the methods described herein. See, e.g., Tzschentke, Amino Acids 23(1-3):147-52 (2002); Reissner and Kalivas, Behav Pharmacol. 2010 September; 21(5-6):514-22 (2010); Myers et al., Neuropsychopharmacology. 36(1):274-93 (2011); World J. Psychiatry. 2016 Mar. 22; 6(1):31-42; CNS Neurol. Disord. Drug. Targets. 2015; 14(6):745-56; Neuroscientist. 2014 December; 20(6):610-22; and Behav. Pharmacol. 2010 September; 21(5-6):514-22.

Glutamate has also been shown to play a role in some psychotic disorders, including schizophrenia, bipolar disorder, and autism (see e.g., Curr Mol Pharmacol. 2013 July; 6(2):66-73; Eur J Pharmacol. 2012 May 5; 682(1-3):1-11; Iran J Child Neurol. 2015 Winter; 9(1):99-102; J Biomed Sci. 2005 December; 12(6):975-84. The methods and compounds described herein can be used to treat subjects with psychotic disorders such as schizophrenia, bipolar disorder, and autism.

Glutamate has also been shown to play a role in some cancers, including necrosis in glioblastoma, which is associated with poor prognosis. See, e.g., Noch and Khalili, Cancer Biol Ther. 8(19):1791-7 (2009). Thus, the compounds and compositions described herein can be used to treat subjects with cancers, e.g., brain cancers such as glioblastoma and glioma.

Glutamate has been shown to play a role in modulating various mood disorders, for example, major depressive disorder (Owen, Drugs today, 2012, 48(7):469-78), anxiety disorders (see e.g., Neuropsychiatr Dis Treat. 2013; 9:1101-12), depressive disorders (see e.g., Expert Rev Clin Pharmacol. 2016 Oct. 26; Biol Psychiatry. 2007 Jan. 15; 61(2): 250-2; and Biol Psychiatry. 2007 Jan. 15; 61(2):137-8), borderline personality disorder (see e.g., Neuropsychopharmacology. 2016 January; 41(2):410-8), attention-deficit-hyperactivity disorder (see e.g., Neuropsychopharmacology.

2016 January; 41(2):410-8; and World J. Biol. Psychiatry. 2016 Dec. 15:1-9), suicidal behavior (see e.g., Prog. Neuropsychopharmacol Biol. Psychiatry. 2016 Oct. 27), eating disorders (see e.g., Curr. Pharm. Des. 2011; 17(14):1396-409), posttraumatic stress disorder (see e.g., Neurosci. Lett. 2016 Dec. 1), gulf war illness (see e.g., J. Neurochem. 2011 October; 119(2):303-13), and obsessive-Compulsive Disorder (see e.g., Pharmacol. Ther. 2011 December; 132(3): 314-332).

The presence of a disorder associated with glutamate excitotoxicity can be diagnosed or determined using methods known in the art, including spectroscopy at 0.5 T to observe the combined glutamate and glutamine (glx) peak (see, e.g., Prost et al., Magn Reson Med 1997; 37:615-618; Mark et al., American Journal of Neuroradiology 22:1813-1824 (2001)). Other known clinical diagnostic methods can also be used to diagnose the presence of a disorder known to be associated with glutamate excitotoxicity, e.g., as described herein.

In some embodiments, glutamate excitotoxicity (and subsequent neurological damage) can be a result of an environmental toxin, e.g., Tributyltin (Nakatsu et al., Toxicol. Sci. (January 2006) 89 (1): 235-242), lead, and domoic acid. Subjects who have been or will be exposed to such toxins can be considered to have a disorder associated with glutamate excitotoxicity and can be treated using the methods described herein. In some embodiments subjects who have been exposed to an environmental toxin known to cause or contribute to glutamate excitotoxicity can be treated using the methods described herein before the onset of clinical (e.g., neurological) symptoms, to prevent or reduce the risk of a disorder associated with glutamate excitotoxicity.

In some embodiments, the present application provides a method for treating a disease or disorder selected from the group consisting of ischemic stroke, epilepsy, trauma, a chronic neurodegenerative disorder, a psychotic disorder, a pain disorder, an addiction, a cancer, a mood disorder, or depression in a subject in need thereof, the method comprising administering to the subject an effective amount of a compound provided herein, or a pharmaceutically acceptable salt thereof.

In some embodiments, the present application provides a method for treating a disease or disorder selected from the group consisting of ischemic stroke, epilepsy, trauma, a chronic neurodegenerative disorder, a psychotic disorder, a pain disorder, an addiction, a cancer, or depression in a subject in need thereof, the method comprising administering to the subject an effective amount of a compound provided herein, or a pharmaceutically acceptable salt thereof.

Example traumas include, but are not limited to, blunt trauma, an abrasion, an avulsion, an incision, a laceration, a puncture, a penetration, a surgical trauma, iatrogenic trauma, a spinal cord injury, a traumatic brain injury, or any combination thereof.

In some embodiments, the chronic neurodegenerative disorder is selected from the group consisting of mild cognitive impairment, Parkinson's disease, Alzheimer's disease, multiple sclerosis, mesial temporal sclerosis, Huntington's disease, AIDS dementia complex, and amyotrophic lateral sclerosis (ALS).

In some embodiments, the psychotic disorder is selected from the group consisting of schizophrenia, bipolar disorder, and autism.

In some embodiments, the pain disorder is selected from the group consisting of migraine, a temporomandibular disorder, neuropathic pain, visceral pain, or complex regional pain syndrome.

In some embodiments, the addiction is selected from the group consisting of alcohol addition, cocaine addiction, heroin addiction, methamphetamine addiction, and nicotine addiction. In some embodiments, the addiction is selected from the group consisting of alcohol addiction and cocaine addiction.

In some embodiments, the cancer is selected from the group consisting of brain cancer, glioblastoma, and glioma. In some embodiments, the cancer is glioblastoma. In some embodiments, the cancer is glioma.

In some embodiments, the mood disorder is selected from the group consisting of an anxiety disorder, a depressive disorder, borderline personality disorder, attention-deficit-hyperactivity disorder, suicidal behavior, an eating disorder, posttraumatic stress disorder, gulf war illness, and obsessive-Compulsive Disorder.

In some embodiments, the depression comprises major depressive disorder. In some embodiments, the depression is major depressive disorder.

In some embodiments, the present application provides a method for treating a disease or disorder selected from the group consisting of ischemic stroke, epilepsy, trauma, or a chronic neurodegenerative disorder, including mild cognitive impairment, Parkinson's disease, Alzheimer's disease, multiple sclerosis, mesial temporal sclerosis, Huntington's disease, AIDS dementia complex, or amyotrophic lateral sclerosis (ALS); a psychotic disorder including schizophrenia, bipolar disorder, and autism, a pain disorder including migraine, temporomandibular disorders, neuropathic pain, visceral pain, or complex regional pain syndrome; an addiction including alcohol addiction, cocaine addiction, heroin addiction, methamphetamine addiction, and nicotine addiction; or a cancer, including glioblastoma; or depression in a subject in need thereof, the method comprising administering to the subject an effective amount of a compound provided herein, or a pharmaceutically acceptable salt thereof.

The present application further provides a method for increasing EAAT2 protein expression in a cell or a subject in need thereof, the method comprising contacting the cell or administering to the subject an effective amount of a compound provided herein, or a pharmaceutically acceptable salt thereof.

The present application further provides a method for activating the NRF2 pathway in a cell or a subject in need thereof, the method comprising contacting the cell or administering to the subject an effective amount of a compound provided herein, or a pharmaceutically acceptable salt thereof.

As used herein, the phrase "effective amount" refers to the amount of active compound or pharmaceutical agent that elicits the biological or medicinal response that is being sought in a tissue, system, animal, individual or human by a researcher, veterinarian, medical doctor or other clinician. An effective amount of a compound provided herein can range, for example, from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

As used herein, to "treat" means to ameliorate at least one symptom of the disorder associated with glutamate excitotoxicity. Often, glutamate excitotoxicity results in neuronal cell death; thus, a treatment can result in a reduction in the rate or amount of neuronal cell death.

Combination Therapies

In some embodiments, the methods provided herein further comprise administering one or more additional therapeutic agents to the subject. In some embodiments, each of the one or more additional therapeutic agents is independently selected from the group consisting of a steroid, an anti-allergic agent, an anesthetic (e.g., for use in combination with a surgical procedure), an immunosuppressant, an anti-microbial agent, an anti-inflammatory agent, and a chemotherapeutic agent.

Example steroids include, but are not limited to, corticosteroids such as cortisone, dexamethasone, hydrocortisone, methylprednisolone, prednisolone, and prednisone.

Example anesthetics include, but are not limited to local anesthetics such as lidocaine, procain, and ropivacaine.

Example immunosuppressants include, but are not limited to, azathioprine, chlorambucil, cyclophosphamide, cyclosporine, daclizumab, infliximab, methotrexate, and tacrolimus.

Example anti-microbial agents include, but are not limited to, aminoglycosides (e.g., gentamicin, neomycin, and streptomycin), penicillins (e.g., amoxicillin and ampicillin), and macrolides (e.g., erythromycin).

Example anti-inflammatory agents include, but are not limited to, aspirin, choline salicylates, celecoxib, diclofenac potassium, diclofenac sodium, diclofenac sodium with misoprostol, diflunisal, etodolac, fenoprofen, flurbiprofen, ibuprofen, ketoprofen, meclofenamate sodium, mefenamic acid, nabumetone, naproxen, naproxen sodium, oxaprozin, piroxican, rofecoxib, salsalate, sodium salicylate, sulindac, tolmetin sodium, and valdecoxib.

Example chemotherapeutics include, but are not limited to, proteosome inhibitors (e.g., bortezomib), thalidomide, revlimid, and DNA-damaging agents such as melphalan, doxorubicin, cyclophosphamide, vincristine, etoposide, carmustine, and the like. For example, one or more of the following agents may be used in combination with the compounds provided herein and are presented as a non-limiting list: a cytostatic agent, cisplatin, taxol, etoposide, irinotecan, topotecan, paclitaxel, docetaxel, epothilones, tamoxifen, 5-fluorouracil, temozolomide, cyclophosphamide, gefitinib, erlotinib hydrochloride, imatinib mesylate, gemcitabine, uracil mustard, chlormethine, ifosfamide, chlorambucil, pipobroman, triethylenemelamine, triethylenethiophosphoramine, busulfan, lomustine, streptozocin, dacarbazine, floxuridine, cytarabine, 6-mercaptopurine, 6-thioguanine, fludarabine phosphate, oxaliplatin, folinic acid, pentostatin, vinblastine, vindesine, bleomycin, dactinomycin, daunorubicin, doxorubicin, epirubicin, idarubicin, mithramycin, deoxycoformycin, mitomycin-C, L-asparaginase, teniposide, 17α-ethinylestradiol, diethylstilbestrol, testosterone, prednisone, fluoxymesterone, dromostanolone propionate, testolactone, megestrol acetate, methyltestosterone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, vinorelbine, anastrazole, letrozole, capecitabine, reloxafine, hexamethylmelamine, bevacizumab, bexxar, velcade, zevalin, trisenox, xeloda, porfimer, erbitux, thiotepa, altretamine, trastuzumab, fulvestrant, exemestane, ifosfamide, rituximab, alemtuzumab, clofarabine, cladribine, aphidicolin, sunitinib, dasatinib, tezacitabine, triapine, trimidox, amidox, bendamustine, and ofatumumab.

Pharmaceutical Compositions

When employed as pharmaceuticals, the compounds provided herein (e.g., compounds of Formula (I), compounds of Formula (Ia), compounds of Formula (II), compounds of Formula (IIa), compounds of Formula (III), compounds of Formula (IIIa), compounds of Formula (IV), and Formula (IVa)), can be administered in the form of pharmaceutical compositions. These compositions can be prepared as described herein or elsewhere, and can be administered by a variety of routes, depending upon whether local or systemic treatment is desired and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral, or parenteral. Parenteral administration includes intravenous, intraarterial, subcutaneous, intraperitoneal intramuscular or injection or infusion; or intracranial, (e.g., intrathecal or intraventricular, administration). Parenteral administration can be in the form of a single bolus dose, or may be, for example, by a continuous perfusion pump. In some embodiments, the compounds provided herein, or a pharmaceutically acceptable salt thereof, are suitable for parenteral administration. In some embodiments, the compounds provided herein are suitable for intravenous administration. In some embodiments, the compounds provided herein are suitable for oral administration. In some embodiments, the compounds provided herein are suitable for topical administration.

Pharmaceutical compositions and formulations for topical administration may include, but are not limited to, transdermal patches, ointments, lotions, creams, gels, drops, suppositories, sprays, liquids and powders. Conventional pharmaceutical carriers, aqueous, powder or oily bases, thickeners and the like may be necessary or desirable. In some embodiments, the pharmaceutical compositions provided herein are suitable for parenteral administration. In some embodiments, the pharmaceutical compositions provided herein are suitable for intravenous administration. In some embodiments, the pharmaceutical compositions provided herein are suitable for oral administration. In some embodiments, the pharmaceutical compositions provided herein are suitable for topical administration.

Also provided are pharmaceutical compositions which contain, as the active ingredient, a compound provided herein, or a pharmaceutically acceptable salt thereof, in combination with one or more pharmaceutically acceptable carriers (e.g. excipients). In making the pharmaceutical compositions provided herein, the active ingredient is typically mixed with an excipient, diluted by an excipient or enclosed within such a carrier in the form of, for example, a capsule, sachet, paper, or other container. When the excipient serves as a diluent, it can be a solid, semi-solid, or liquid material, which acts as a vehicle, carrier or medium for the active ingredient. Thus, the compositions can be, for example, in the form of tablets, pills, powders, lozenges, sachets, cachets, elixirs, suspensions, emulsions, solutions, syrups, aerosols (as a solid or in a liquid medium), ointments, soft and hard gelatin capsules, suppositories, sterile injectable solutions, and sterile packaged powders.

Some examples of suitable excipients include, without limitation, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include, without limitation, lubricating agents such as talc, magnesium stearate, and mineral oil; wetting agents; emulsifying and suspending agents; preserving agents such as methyl- and propylhydroxy-benzoates; sweetening agents; flavoring agents, or combinations thereof.

The active compound can be effective over a wide dosage range and is generally administered in an effective amount. It will be understood, however, that the amount of the compound actually administered will usually be determined by a physician, according to the relevant circumstances, including the condition to be treated, the chosen route of administration, the actual compound administered, the age, weight, and response of the individual subject, the severity of the subject's symptoms, and the like.

The compositions provided herein can be administered one from one or more times per day to one or more times per week; including once every other day. The skilled artisan will appreciate that certain factors can influence the dosage and timing required to effectively treat a subject, including, but not limited to, the severity of the disease or disorder, previous treatments, the general health and/or age of the subject, and other diseases present. Moreover, treatment of a subject with a therapeutically effective amount of a compound described herein can include a single treatment or a series of treatments.

Dosage, toxicity and therapeutic efficacy of the compounds provided herein can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit high therapeutic indices are preferred. While compounds that exhibit toxic side effects can be used, care should be taken to design a delivery system that targets such compounds to the site of affected tissue in order to minimize potential damage to uninfected cells and, thereby, reduce side effects.

EXAMPLES

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results.

Example 1. General Procedure for Synthesis of Amide Analogs

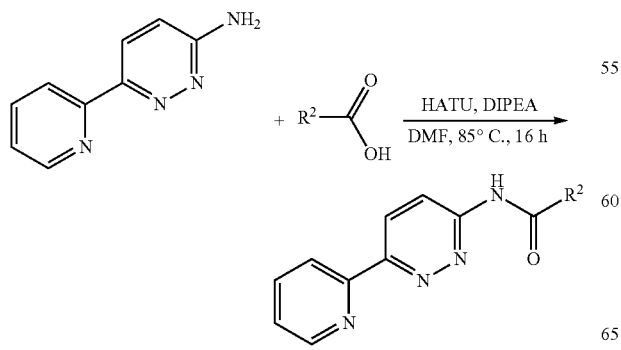

N,N-Diisopropylethylamine (DIPEA) (258 mg, 2.0 mmol) was slowly added dropwise to a solution of 1-[bis (dimethylamino)methylene]-1H-1,2,3-triazolo[4,5-b]pyridinium 3-oxid hexafluorophosphate (HATU) (456 mg, 1.2 mmol) in DMF (2.0 mL). The solution was stirred for 5 minutes and then added dropwise to a mixture of the appropriate carboxylic acid (1.0 mmol) and 6-(pyridin-2-yl) pyridazin-3-amine (172 mg, 1.0 mmol) in a reaction vial. The solution was stirred at 85° C. for 16 hours. The reaction was monitored by TLC or LCMS. The product was isolated and purified by silica gel chromatography eluting with the cyclohexane and ethyl acetate mixtures.

Example 2. General Procedure for Synthesis of Ether Analogs

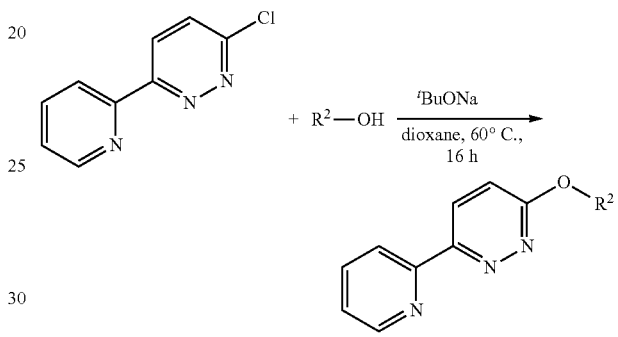

To a solution of the appropriate alcohol (1 mmol) and anhydrous 1,4-dioxane (1 mL) was added sodium tert-butoxide (106 mg, 1.1 mmol). The tube was flushed with argon, capped, and the mixture was stirred at room temperature for five minutes. A solution of 3-chloro-6-(pyridin-2-yl)pyridazine (192 mg, 1 mmol) in anhydrous 1,4-dioxane (1 mL) was then added and the mixture was stirred at 65° C. for 16 hours. The mixture was partitioned between ethyl acetate (3×5 mL) and 5% aqueous $NaH_2PO_4$ (5 mL). The organic layer was evaporated and the residue was purified by silica gel chromatography eluting with cyclohexane and ethyl acetate.

The compounds of Example 3-57 were prepared according to the general procedure described in Example 1 or Example 2 using the appropriate starting materials.

Example 3.
N-(6-(Pyridin-2-yl)pyridazin-3-yl)picolinamide

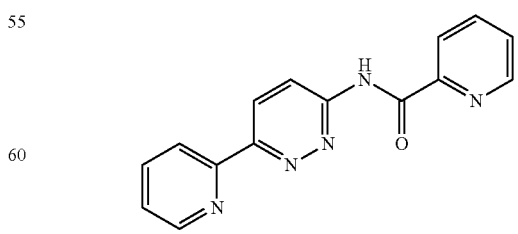

$^1$H NMR (500 MHz, CDCl$_3$): 11.1 (s, 1H), 8.81 (d, J=9.3 Hz, 1H), 8.72 (m, 1H), 8.65 (d, J=3.0 Hz, 1H), 8.63 (d, J=4.3 Hz, 1H), 8.33 (d, J=7.8 Hz, H), 7.96 (td, J=7.7, 1.6 Hz, 1H), 7.88 (td, J=7.8, 1.7 Hz, 1H), 7.56 (ddd, J=7.4, 4.8, 0.8 Hz, 1H), 7.38 (ddd, J=7.4, 4.9, 0.8 Hz, 1H). [M+1]$^+$=278.1.

Example 4. 4-Fluoro-N-(6-(pyridin-2-yl)pyridazin-3-yl)benzamide

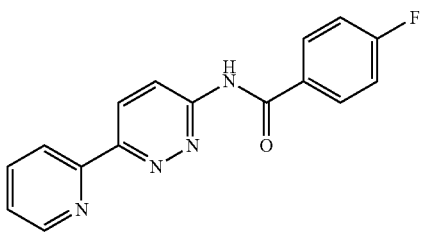 [SMILES: O=C(Nc1ccc(-c2ccccn2)nn1)c1ccc(F)cc1]

$^1$H NMR (500 MHz, DMSO-d6): 11.68 (s, 1H), 8.75 (ddd, J=4.7, 1.3, 0.7 Hz, 1H), 8.58 (q, J=9.4 Hz, 2H), 8.52 (dd, J=7.9, 0.8 Hz, 1H), 8.18 (m, 2H), 8.02 (td, J=7.7, 1.6 Hz, 1H), 7.54 (ddd, J=7.4, 4.8, 1.0 Hz, 1H), 7.39 (t, J=8.8 Hz, 2H). [M+1]$^+$=295.1.

Example 5. 4-Methoxy-N-(6-(pyridin-2-yl)pyridazin-3-yl)benzamide

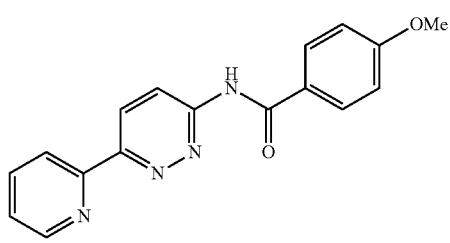 [SMILES: COc1ccc(C(=O)Nc2ccc(-c3ccccn3)nn2)cc1]

$^1$H NMR (500 MHz, DMSO-d6): 11.46 (s, 1H), 8.75 (ddd, J=4.8, 1.8, 1.0 Hz, 1H), 8.57 (d, J=9.4 Hz, 1H), 8.55 (d, J=9.3 Hz, 1H), 8.51 (dt, J=7.9, 1.0 Hz, 1H), 8.12 (dt, J=9.0, 2.1 Hz, 1H), 8.02 (td, J=7.6, 1.8 Hz, 1H), 7.53 (ddd, J=7.5, 4.8, 1.2 Hz, 1H), 7.08 (dt, J=9.0, 2.1 Hz, 1H), 3.86 (s, 3H). [M+1]$^+$=307.1.

Example 6. 4-Chloro-N-(6-(pyridin-2-yl)pyridazin-3-yl)benzamide

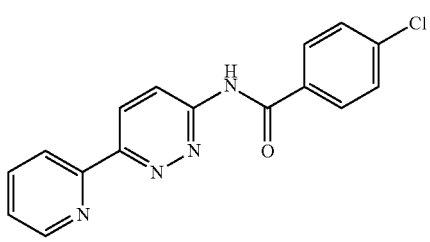 [SMILES: O=C(Nc1ccc(-c2ccccn2)nn1)c1ccc(Cl)cc1]

$^1$H NMR (500 MHz, DMSO-d6): 11.74 (s, 1H), 8.75 (ddd, J=4.8, 1.7, 0.9 Hz, 1H), 8.58 (q, J=9.4 Hz, 2H), 8.52 (dd, J=8.0, 1.0 Hz, 1H), 8.11 (m, 2H), 8.02 (td, J=7.6, 1.7 Hz, 1H), 7.64 (m, 2H), 7.54 (ddd, J=7.5, 4.8, 1.1 Hz, 1H). [M+1]$^+$=311.1.

Example 7. 2-Chloro-N-(6-(pyridin-2-yl)pyridazin-3-yl)benzamide

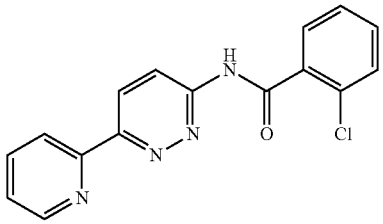 [SMILES: O=C(Nc1ccc(-c2ccccn2)nn1)c1ccccc1Cl]

$^1$H NMR (500 MHz, DMSO-d6): 11.86 (s, 1H), 8.75 (ddt, J=4.8, 1.7, 0.8 Hz, 1H), 8.61 (d, J=9.3 Hz, 1H), 8.59 (d, J=9.4 Hz, 1H), 8.51 (dq, J=7.9, 0.8 Hz, 1H), 8.02 (tdd, J=8.0, 1.8, 0.6 Hz, 1H), 7.67 (dd, J=7.4, 1.6 Hz, 1H), 7.59 (d, J=8.0 Hz, 1H), 7.54 (m, 2H), 7.47 (tdd, J=7.5, 1.3, 0.7 Hz, 1H). [M+1]$^+$=311.1.

Example 8. N-(6-(Pyridin-2-yl)pyridazin-3-yl)pyrimidine-2-carboxamide

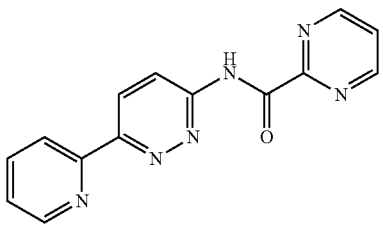 [SMILES: O=C(Nc1ccc(-c2ccccn2)nn1)c1ncccn1]

$^1$H NMR (600 MHz, DMSO-d6): 11.20 (s, 1H), 9.08 (d, J=4.9 Hz, 2H), 8.73 (ddd, J=4.8, 1.8, 0.7 Hz, 1H), 8.66 (d, J=9.6 Hz, 1H), 8.63 (d, J=9.6 Hz, 1H), 8.51 (dt, J=8.0, 1.1 Hz, 1H), 8.00 (td, J=7.7, 1.8 Hz, 1H), 7.79 (t, J=4.9 Hz, 1H), 7.52 (ddd, J=7.5, 4.8, 1.2 Hz, 1H). [M+1]$^+$=279.2.

Example 9. N-(6-(Pyridin-2-yl)pyridazin-3-yl)pyridazine-3-carboxamide

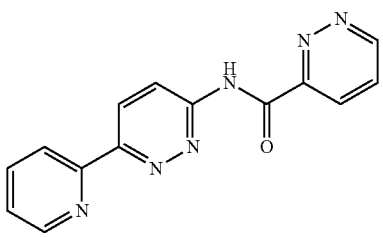 [SMILES: O=C(Nc1ccc(-c2ccccn2)nn1)c1cccnn1]

$^1$H NMR (600 MHz, DMSO-d6): 11.35 (s, 1H), 9.51 (dd, J=5.0, 1.6 Hz, 1H), 8.73 (ddd, J=5.1, 1.7, 0.8 Hz, 1H), 8.64 (d, J=3.7 Hz, 1H), 8.53 (dt, J=8.0, 1.2 Hz, 1H), 8.39 (dd, J=8.5, 1.6 Hz, 1H), 8.26 (s, 1H), 8.01 (m, 2H), 7.52 (ddd, J=7.4, 4.7, 1.1 Hz, 1H), 7.41 (dd, J=8.4, 4.3 Hz, 1H). [M+1]$^+$=279.2.

Example 10. 4-Fluoro-N-(6-(pyridin-2-yl)pyridazin-3-yl)picolinamide

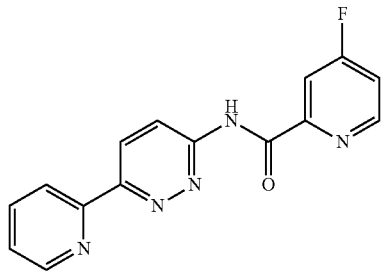 [SMILES: O=C(Nc1ccc(-c2ccccn2)nn1)c1cc(F)ccn1]

¹H NMR (600 MHz, CDCl₃): 10.99 (s, 1H), 8.78 (d, J=9.3 Hz, 1H), 8.72 (ddd, J=4.8, 1.7, 0.9 Hz, 1H), 8.70 (m, 1H), 8.67 (d, J=8.9 Hz, 1H), 8.64 (dt, J=7.0, 1.0 Hz, 1H), 8.03 (dd, J=8.9, 2.6 Hz, 1H), 7.89 (td, J=7.6, 1.8 Hz, 1H), 7.39 (ddd, J=7.5, 4.8, 1.2 Hz, 1H), 7.28 (ddd, J=8.0, 5.5, 2.6 Hz, 1H). [M+1]⁺=296.1.

Example 11. 5-Fluoro-N-(6-(pyridin-2-yl)pyridazin-3-yl)picolinamide

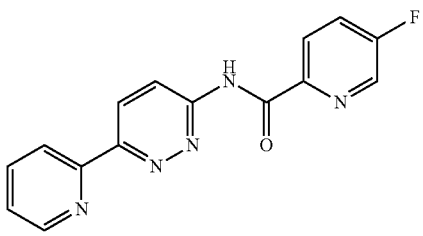 [SMILES: O=C(Nc1ccc(-c2ccccn2)nn1)c1ccc(F)cn1]

¹H NMR (600 MHz, CDCl₃): 10.89 (s, 1H), 8.79 (d, J=9.3 Hz, 1H), 8.73 (ddd, J=4.9, 1.9, 0.9 Hz, 1H), 8.70 (d, J=9.5 Hz, 1H), 8.67 (dt, J=8.0, 1.1 Hz, 1H), 8.55 (d, J=2.8 Hz, 1H), 8.37 (ddd, J=8.7, 4.5, 0.6 Hz, 1H), 7.92 (td, J=7.7, 1.8 Hz, 1H), 7.64 (ddd, J=8.7, 7.9, 2.7 Hz, 1H), 7.42 (ddd, J=7.7, 4.9, 1.2 Hz, 1H). [M+1]⁺=296.1.

Example 12. 6-Fluoro-N-(6-(pyridin-2-yl)pyridazin-3-yl)picolinamide

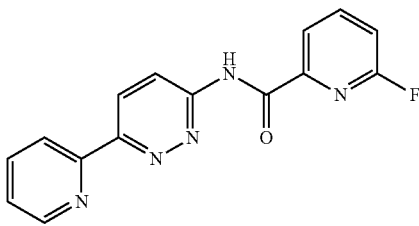 [SMILES: O=C(Nc1ccc(-c2ccccn2)nn1)c1cccc(F)n1]

¹H NMR (600 MHz, CDCl₃): 10.66 (s, 1H), 8.79 (d, J=9.3 Hz, 1H), 8.74 (d, J=9.0 Hz, 1H), 8.73 (ddd, J=5.0, 1.9, 1.0 Hz, 1H), 8.69 (dt, J=7.9, 0.7 Hz, 1H), 8.23 (ddd, J=7.3, 2.1, 0.8 Hz, 1H), 8.07 (q, J=7.5 Hz, 1H), 7.95 (td, J=7.8, 1.8 Hz, 1H), 7.44 (ddd, J=7.6, 4.9, 1.1 Hz, 1H), 7.22 (ddd, J=8.2, 2.6, 0.8 Hz, 1H). [M+1]⁺=296.1.

Example 13. 1-Methyl-N-(6-(pyridin-2-yl)pyridazin-3-yl)-1H-imidazole-2-carboxamide

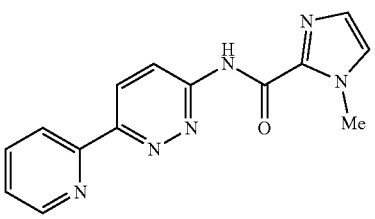 [SMILES: Cn1ccnc1C(=O)Nc1ccc(-c2ccccn2)nn1]

¹H NMR (600 MHz, CDCl₃): 8.62 (d, J=1.4 Hz, 1H), 8.57 (d, J=9.4 Hz, 1H), 8.52 (dt, J=7.9, 0.7 Hz, 1H), 8.50 (d, J=9.3 Hz, 1H), 7.85 (td, J=7.5, 1.7 Hz, 1H), 7.35 (ddd, J=7.4, 5.5, 1.6 Hz, 1H), 7.09 (d, J=1.0 Hz, 1H), 7.06 (d, J=0.9 Hz, 1H), 4.06 (s, 3H). [M+1]⁺=281.1.

Example 14. 1-Methyl-N-(6-(pyridin-2-yl)pyridazin-3-yl)-1H-imidazole-4-carboxamide

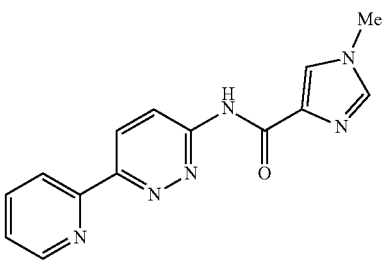 [SMILES: Cn1cnc(C(=O)Nc2ccc(-c3ccccn3)nn2)c1]

¹H NMR (600 MHz, CDCl₃): 8.74 (d, J=9.3 Hz, 1H), 8.70 (ddd, J=4.7, 1.6, 0.8 Hz, 1H), 8.62 (dt, J=7.2, 1.2 Hz, 1H), 8.59 (d, J=9.4 Hz, 1H), 7.87 (td, J=7.9, 1.9 Hz, 1H), 7.69 (d, J=1.3 Hz, 1H), 7.48 (d, J=1.4 Hz, 1H), 7.37 (ddd, J=7.7, 4.7, 1.2 Hz, 1H), 3.80 (s, 3H). [M+1]⁺=281.1.

Example 15. 1-Methyl-N-(6-(pyridin-2-yl)pyridazin-3-yl)-1H-imidazole-5-carboxamide

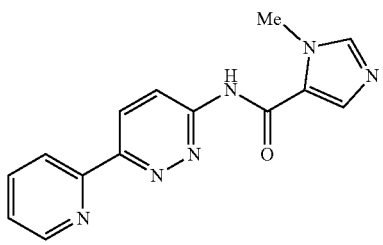 [SMILES: Cn1cncc1C(=O)Nc1ccc(-c2ccccn2)nn1]

¹H NMR (600 MHz, DMSO-d6): 11.48 (s, 1H), 8.72 (d, J=4.6 Hz, 1H), 8.50 (t, J=9.4 Hz, 2H), 8.15 (s, 1H), 7.97 (m, 2H), 7.50 (dd, J=7.4, 3.7 Hz, 1H), 3.89 (s, 3H). [M+1]⁺=281.1.

Example 16. N-(6-(Pyridin-2-yl)pyridazin-3-yl)thiazole-5-carboxamide

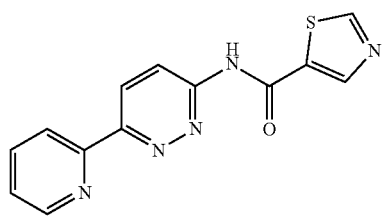 [SMILES: O=C(Nc1ccc(-c2ccccn2)nn1)c1cncs1]

¹H NMR (600 MHz, DMSO-d6): 11.99 (s, 1H), 9.36 (s, 1H), 8.97 (s, 1H), 8.73 (ddd, J=4.8, 1.8, 0.9 Hz, 1H), 8.58 (d, J=9.3 Hz, 1H), 8.51 (dt, J=7.9, 1.1 Hz, 1H), 8.50 (d, J=9.4 Hz, 1H), 8.00 (td, J=7.8, 1.8 Hz, 1H), 7.52 (ddd, J=7.5, 4.8, 1.2 Hz, 1H). [M+1]⁺=284.1.

Example 17. 4-Fluoro-N-(6-(pyridin-3-yl)pyridazin-3-yl)benzamide

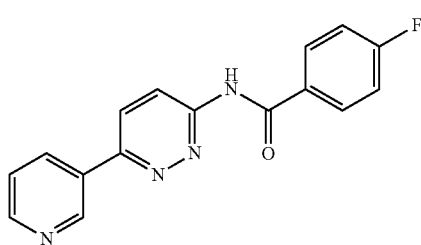 [SMILES: O=C(Nc1ccc(-c2cccnc2)nn1)c1ccc(F)cc1]

¹H NMR (400 MHz, DMSO-d6) δ 11.17 (s, 1H), 9.24 (s, 1H), 8.62 (d, 1H), 8.46 (d, 1H), 8.30 (d, 1H), 8.16 (m, 2H), 7.37 (m, 2H). LCMS: m/z calculated for C16H11FN4O: 294.09; measured: 295.1.

Example 18. 4-Fluoro-N-(6-(o-tolyl)pyridazin-3-yl)benzamide

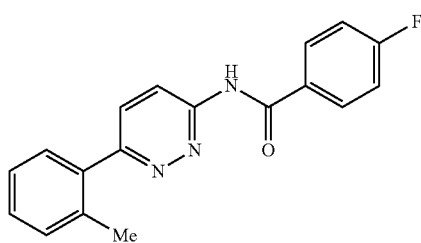 [SMILES: Cc1ccccc1-c1ccc(NC(=O)c2ccc(F)cc2)nn1]

¹H NMR (400 MHz, DMSO-d6) δ 11.60 (s, 1H), 8.44 (d, J=9.2 Hz, 1H), 8.20-8.16 (m, 2H), 7.89 (d, J=9.3 Hz, 1H), 7.46 (d, 1H), 7.40-7.34 (m, 5H), 2.34 (s, 3H). LCMS: m/z calculated for C18H14FN3O: 307.11; measured (m+1): 308.1.

Example 19. 4-Fluoro-N-(6-(2-methoxyphenyl)pyridazin-3-yl)benzamide

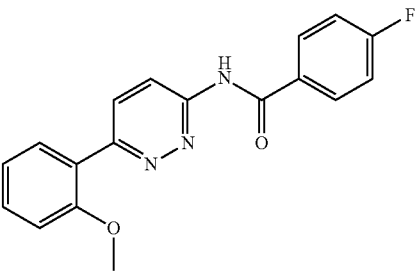 [SMILES: COc1ccccc1-c1ccc(NC(=O)c2ccc(F)cc2)nn1]

¹H NMR (400 MHz, DMSO-d6) δ 11.52 (s, 1H), 8.38 (d, J=9.5 Hz, 1H), 8.20-8.16 (m, 2H), 8.09 (d, J=9.5 Hz, 1H), 7.77-7.74 (m, 1H), 7.55 (m, 1H), 7.40-7.36 (m, 2H), 7.21 (d, 1H), 7.13 (t, 1H), 3.85 (s, 3H). LCMS: m/z calculated for C18H14FN3O2: 323.11; measured (m+1): 324.1.

Example 20. 4-Fluoro-N-(6-(2-fluorophenyl)pyridazin-3-yl)benzamide

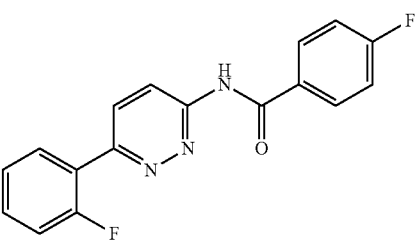 [SMILES: O=C(Nc1ccc(-c2ccccc2F)nn1)c1ccc(F)cc1]

¹H NMR (400 MHz, DMSO-d6) δ 11.63 (s, 1H), 8.50 (m, 1H), 8.20-8.16 (m, 2H), 8.12-8.09 (m, 1H), 8.00-7.96 (m, 1H), 7.61-7.55 (m, 1H), 7.43-7.36 (m, 4H). LCMS: m/z calculated for C17H11F2N3O: 311.29; measured (m+1): 312.1.

Example 21. N,N-Dimethyl-2-(6-(pyridin-2-yl)pyridazin-3-yloxy)acetamide

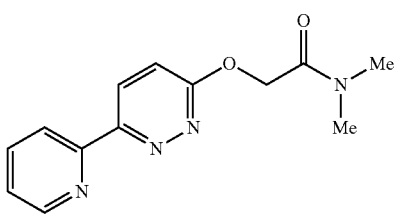 [SMILES: CN(C)C(=O)COc1ccc(-c2ccccn2)nn1]

¹H NMR (500 MHz, CDCl₃): 8.62 (d, J=4.7 Hz, 1H), 8.38 (d, J=9.8 Hz, 1H), 8.10 (d, J=8.1 Hz, 1H), 7.74 (td, J=7.7, 1.1 Hz, 1H), 7.29 (m, 1H), 7.06 (d, J=9.8 Hz, 1H), 5.07 (s, 2H), 3.13 (s, 3H), 3.02 (s, 3H). [M+1]⁺=259.2.

Example 22. 1-(Piperidin-1-yl)-2-(6-(pyridin-2-yl)pyridazin-3-yloxy)ethanone

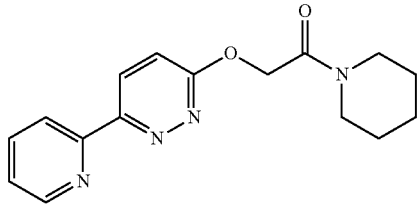 [SMILES: O=C(COc1ccc(-c2ccccn2)nn1)N1CCCCC1]

¹H NMR (500 MHz, CDCl₃): 8.62 (m, 1H), 8.37 (d, J=9.7 Hz, 1H), 8.11 (dd, J=8.0, 0.8 Hz, 1H), 7.74 (td, J=7.5, 1.7 Hz, 1H), 7.29 (m, 1H), 7.06 (d, J=9.7 Hz, 1H), 5.07 (s, 2H), 3.60 (t, J=5.5 Hz, 2H), 3.47 (t, J=5.5 Hz, 2H), 1.68 (m, 4H), 1.60 (m, 2H). [M+1]⁺=299.2.

Example 23. Ethyl 2-(6-(pyridin-2-yl)pyridazin-3-yloxy)acetate

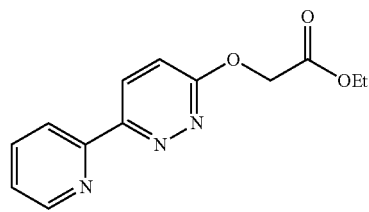 [SMILES: CCOC(=O)COc1ccc(-c2ccccn2)nn1]

¹H NMR (500 MHz, CDCl₃): 8.63 (m, 1H), 8.39 (d, J=9.8 Hz, 1H), 8.10 (d, J=8.0 Hz, 1H), 7.77 (td, J=7.7, 1.6 Hz, 1H), 7.32 (ddd, J=7.5, 4.9, 0.9 Hz, 1H), 7.07 (d, J=9.8 Hz, 1H), 4.98 (s, 2H), 4.27 (q, J=7.1 Hz, 2H), 1.30 (t, J=7.1 Hz, 3H). [M+1]⁺=259.1.

Example 24. N-Methyl-N-phenyl-2-(6-(pyridin-2-yl)pyridazin-3-yloxy)acetamide

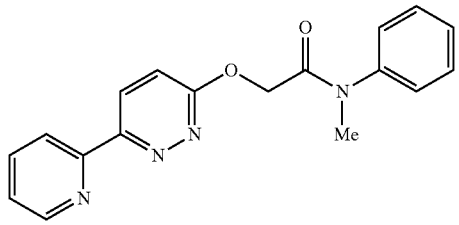 [SMILES: CN(C(=O)COc1ccc(-c2ccccn2)nn1)c1ccccc1]

¹H NMR (500 MHz, CDCl₃): 8.61 (ddd, J=4.7, 1.5, 0.8 Hz, 1H), 8.34 (d, J=9.7 Hz, 1H), 8.08 (d, J=8.0 Hz, 1H), 7.74 (m, 1H), 7.49 (t, J=7.6 Hz, 2H), 7.41 (m, 3H), 7.29 (ddd, J=7.5, 4.8, 0.9 Hz, 1H), 7.01 (d, J=9.8 Hz, 1H), 4.75 (s, 2H), 3.34 (s, 3H). [M+1]⁺=321.1.

Example 25. 2-(6-(Pyridin-2-yl)pyridazin-3-yloxy)-N-o-tolylacetamide

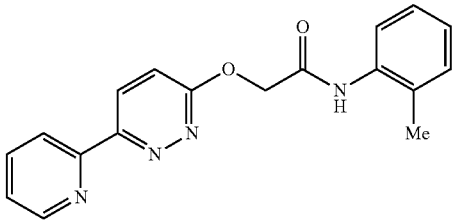 [SMILES: Cc1ccccc1NC(=O)COc1ccc(-c2ccccn2)nn1]

¹H NMR (500 MHz, CDCl₃): 8.64 (d, J=4.8 Hz, 1H), 8.60 (br, s, 1H), 8.49 (d, J=9.7 Hz, 1H), 8.21 (d, J=8.0 Hz, 1H), 7.96 (d, J=8.0 Hz, 1H), 7.80 (td, J=7.7, 1.3 Hz, 1H), 7.34 (dd, J=7.2, 4.9 Hz, 1H), 7.17 (m, 2H), 7.04 (t, J=7.4 Hz, 1H), 5.11 (s, 2H), 2.25 (s, 3H). [M+1]⁺=321.2.

Example 26. 2-(6-(Pyridin-2-yl)pyridazin-3-yloxy)acetamide

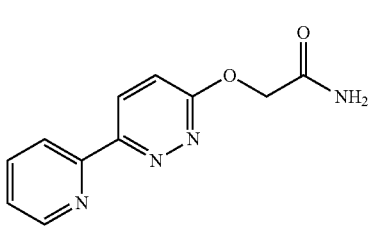 [SMILES: NC(=O)COc1ccc(-c2ccccn2)nn1]

¹H NMR (500 MHz, DMSO-d6): 8.68 (d, J=4.8 Hz, 1H), 8.32 (d, J=9.7 Hz, 1H), 8.06 (d, J=8.0 Hz, 1H), 7.94 (td, J=7.6, 1.5 Hz, 1H), 7.65 (s, 1H), 7.48 (dd, J=6.8, 5.2 Hz, 1H), 7.28 (s, 1H), 7.10 (d, J=9.7 Hz, 1H), 4.75 (s, 2H). [M+1]⁺=231.2.

Example 27. N-Ethyl-2-(6-(pyridin-2-yl)pyridazin-3-yloxy)acetamide

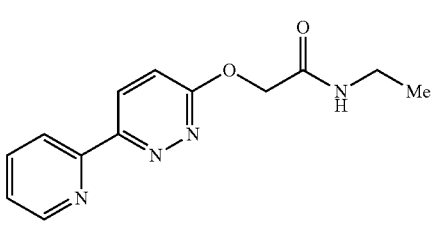 [SMILES: CCNC(=O)COc1ccc(-c2ccccn2)nn1]

¹H NMR (500 MHz, DMSO-d6): 8.68 (d, J=4.8 Hz, 1H), 8.32 (d, J=9.7 Hz, 1H), 8.18 (br, t, J=5.3 Hz, 1H), 8.06 (d, J=7.9 Hz, 1H), 7.94 (td, J=7.7, 1.6 Hz, 1H), 7.48 (dd, J=7.2, 5.0 Hz, 1H), 7.10 (d, J=9.8 Hz, 1H), 4.75 (s, 2H), 3.12 (qd, J=7.2, 5.7 Hz, 2H), 1.04 (t, J=7.3 Hz, 3H). [M+1]⁺=259.1.

Example 28. 2-((6-(Pyridin-2-yl)pyridazin-3-yloxy)methyl)oxazole

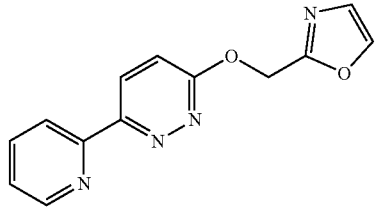

¹H NMR (600 MHz, CDCl₃): 8.53 (ddd, J=4.8, 1.9, 0.8 Hz, 1H), 8.34 (dd, J=8.9, 0.7 Hz, 1H), 8.26 (dd, J=2.5, 0.7 Hz, 1H), 8.00 (s, 1H), 7.89 (ddd, J=8.2, 7.3, 1.9 Hz, 1H), 7.83 (dt, J=8.1, 1.0 Hz, 1H), 7.72 (ddd, J=8.8, 2.5, 0.5 Hz, 1H), 7.32 (ddd, J=7.4, 4.9, 1.2 Hz, 1H), 2.98 (s, 2H). [M+1]⁺=255.1.

Example 29. N,N-Dimethyl-2-(6-(pyridin-2-yl)pyridazin-3-yloxy)ethanamine

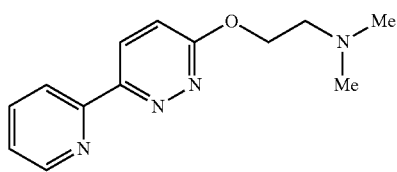 [SMILES: CN(C)CCOc1ccc(-c2ccccn2)nn1]

¹H NMR (600 MHz, CDCl₃): 8.63 (ddd, J=4.8, 1.8, 1.0 Hz, 1H), 8.41 (d, J=9.7 Hz, 1H), 8.18 (dt, J=8.1, 0.9 Hz, 1H), 7.81 (dt, J=7.6, 1.8 Hz, 1H), 7.33 (ddd, J=7.5, 4.8, 1.2 Hz, 1H), 7.05 (d, J=9.7 Hz, 1H), 4.89 (t, J=6.6 Hz, 1H), 3.91 (t, J=6.7 Hz, 1H), 3.39 (s, 6H). [M+1]⁺=245.2.

Example 30. 3-(Pyridin-2-yl)-6-(pyridin-2-ylmethoxy)pyridazine

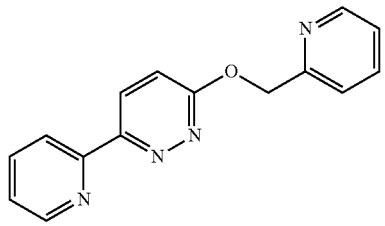 [SMILES: c1ccc(COc2ccc(-c3ccccn3)nn2)nc1]

¹H NMR (600 MHz, DMSO-d6): 8.62 (ddd, J=4.8, 1.7, 0.9 Hz, 1H), 8.58 (ddd, J=4.8, 1.7, 0.8 Hz, 1H), 8.39 (d, J=9.7 Hz, 1H), 8.11 (dt, J=8.0, 1.0 Hz, 1H), 7.74 (ddd, J=7.9, 7.5, 1.8 Hz, 1H), 7.65 (td, J=7.7, 1.8 Hz, 1H), 7.29 (ddd, J=7.4, 4.8, 1.1 Hz, 1H), 7.27 (m, 1H), 7.20 (ddd, J=7.4, 4.9, 1.0 Hz, 1H), 7.09 (d, J=9.7 Hz, 1H), 5.59 (s, 2H). [M+1]⁺=265.2.

Example 31. N-Methyl-2-(6-(pyridin-2-yl)pyridazin-3-yloxy)acetamide

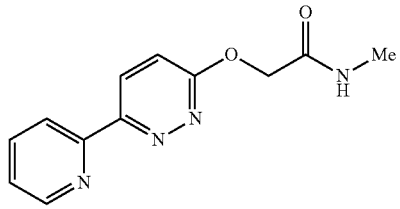 [SMILES: CNC(=O)COc1ccc(-c2ccccn2)nn1]

¹H NMR (500 MHz, DMSO-d6): 8.68 (d, J=4.8 Hz, 1H), 8.32 (d, J=9.7 Hz, 1H), 8.08 (q, J=4.2 Hz, 1H), 8.05 (dd, J=8.0, 0.9 Hz, 1H), 7.94 (td, J=7.9, 1.6 Hz, 1H), 7.48 (ddd, J=7.4, 4.8, 1.0 Hz, 1H), 7.10 (d, J=9.7 Hz, 1H), 4.76 (s, 2H), 2.62 (d, J=4.6 Hz, 3H). [M+1]⁺=245.2.

Example 32. 3-((1-Methyl-1H-imidazol-2-yl)methoxy)-6-(pyridin-2-yl)pyridazine

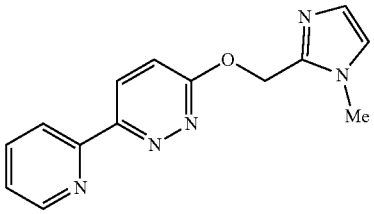 [SMILES: Cn1ccnc1COc1ccc(-c2ccccn2)nn1]

¹H NMR (600 MHz, CDCl₃): 8.67 (ddd, J=4.8, 1.7, 0.9 Hz, 1H), 8.56 (dt, J=8.0, 1.1 Hz, 1H), 8.51 (d, J=9.2 Hz, 1H), 7.85 (td, J=7.6, 1.8 Hz, 1H), 7.35 (ddd, J=7.5, 4.8, 1.2 Hz, 1H), 7.15 (d, J=9.2 Hz, 1H), 7.10 (d, J=1.2 Hz, 1H), 6.97 (d, J=1.2 Hz, 1H), 5.73 (s, 2H), 3.80 (s, 3H). [M+1]⁺=268.1.

Example 33. 3-((1-Methyl-1H-imidazol-5-yl)methoxy)-6-(pyridin-2-yl)pyridazine

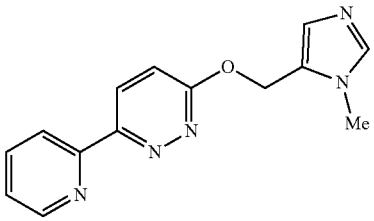 [SMILES: Cn1cncc1COc1ccc(-c2ccccn2)nn1]

¹H NMR (600 MHz, CDCl₃): 8.67 (ddd, J=4.8, 1.7, 0.9 Hz, 1H), 8.57 (dt, J=8.0, 0.9 Hz, 1H), 8.51 (d, J=9.2 Hz, 1H), 7.85 (td, J=7.7, 1.8 Hz, 1H), 7.59 (s, 1H), 7.36 (ddd, J=7.4, 4.8, 1.1 Hz, 1H), 7.25 (m, 1H), 5.65 (s, 2H), 3.75 (s, 3H). [M+1]⁺=268.1.

Example 34. 2-((6-(Pyridin-2-yl)pyridazin-3-yloxy)methyl)thiazole

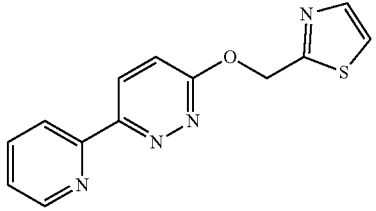 [SMILES: c1ccc(-c2ccc(OCc3nccs3)nn2)nc1]

¹H NMR (600 MHz, CDCl₃): 8.68 (ddd, J=4.8, 1.7, 0.9 Hz, 1H), 8.59 (dt, J=8.0, 1.0 Hz, 1H), 8.56 (d, J=9.2 Hz, 1H), 7.86 (td, J=7.7, 1.8 Hz, 1H), 7.84 (d, J=3.2 Hz, 1H), 7.40 (d, J=3.3 Hz, 1H), 7.37 (ddd, J=7.6, 4.9, 1.2 Hz, 1H), 7.22 (d, J=9.2 Hz, 1H), 5.97 (s, 2H). [M+1]⁺=271.1.

Example 35. 2-Fluoro-N-(6-(pyridin-2-yl)pyridazin-3-yl)benzenesulfonamide

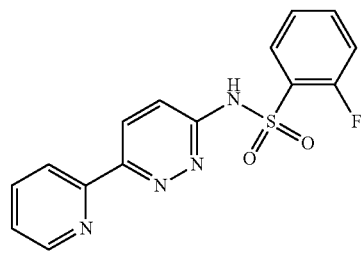 [SMILES: O=S(=O)(Nc1ccc(-c2ccccn2)nn1)c1ccccc1F]

¹H NMR (600 MHz, DMSO-d6): 8.69 (ddd, J=4.7, 1.5, 0.7 Hz, 1H), 8.65 (ddd, J=4.8, 1.8, 1.0 Hz, 1H), 8.62 (dd, J=8.7, 0.8 Hz, 1H), 8.55 (m, 1H), 8.51 (d, J=9.6 Hz, 1H), 8.01 (dd, J=7.9, 1.4 Hz, 1H), 7.80 (td, J=7.6, 0.9 Hz, 1H), 7.66 (d, J=9.5 Hz, 1H), 7.61 (dd, J=4.7, 1.0 Hz, 1H), 7.42 (ddd, J=7.4, 5.1, 1.5 Hz, 1H). [M+1]⁺=331.1.

Example 36. 4-Fluoro-N-(6-(pyridin-2-yl)pyridazin-3-yl)benzenesulfonamide

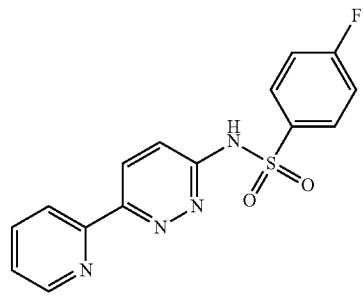 [SMILES: O=S(=O)(Nc1ccc(-c2ccccn2)nn1)c1ccc(F)cc1]

¹H NMR (600 MHz, CDCl₃): 8.69 (dd, J=4.8, 1.5, 0.9 Hz, 1H), 8.53 (d, J=9.9 Hz, 1H), 8.12 (m, 1H), 8.04 (m, 1H), 7.95 (td, J=7.9, 1.8 Hz, 2H), 7.92 (m, 1H), 7.50 (ddd, J=7.4, 4.8, 1.0 Hz, 1H), 7.37 (t, J=8.8 Hz, 2H). [M+1]⁺=331.1.

Example 37. 3-Chloro-4-fluoro-N-(6-(pyridin-2-yl)pyridazin-3-yl)benzamide

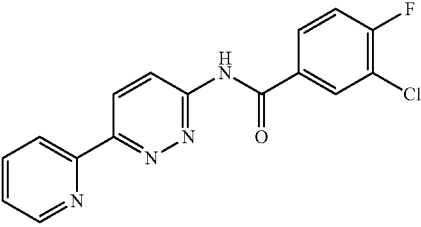 [SMILES: O=C(Nc1ccc(-c2ccccn2)nn1)c1ccc(F)c(Cl)c1]

¹H NMR (600 MHz, DMSO-d6): 11.76 (s, 1H), 8.73 (ddd, J=4.7, 1.4, 0.8 Hz, 1H), 8.58 (d, J=9.5 Hz, 1H), 8.52 (d, J=9.1 Hz, 1H), 8.50 (dt, J=7.5, 1.0 Hz, 1H), 8.32 (dd, J=7.3, 2.0 Hz, 1H), 8.10 (m, 1H), 8.01 (td, J=7.7, 1.8 Hz, 1H), 7.59 (t, J=9.1 Hz, 1H), 7.52 (ddd, J=7.7, 4.8, 1.1 Hz, 1H). [M+1]⁺=329.1.

Example 38. 3-(((6-(Pyridin-2-yl)pyridazin-3-yl)oxy)methyl)isoxazole

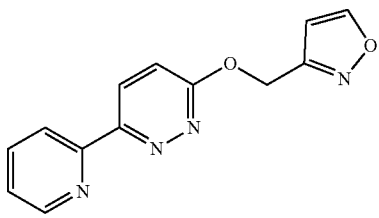 [SMILES: c1ccc(-c2ccc(OCc3ccon3)nn2)nc1]

¹H NMR (400 MHz, CDCl₃) δ 8.68 (ddd, J=4.9, 1.9, 0.9 Hz, 1H), 8.58 (dt, J=8.1, 0.9 Hz, 1H), 8.56 (d, J=9.2 Hz, 1H), 7.88 (td, J=7.7, 1.8 Hz, 1H), 7.47 (d, J=1.9 Hz, 1H), 7.38 (ddd, J=7.5, 4.8, 1.1 Hz, 1H), 7.13 (d, J=9.2 Hz, 1H), 6.44 (d, J=1.9 Hz, 1H), 5.67 (s, 2H), 3.98 (s, 3H). MS 255 (M+1).

Example 39. (S)-1-phenyl-2{(6-(pyridin-2-yl)pyridazin-3-yl)oxy)ethan-1-amine

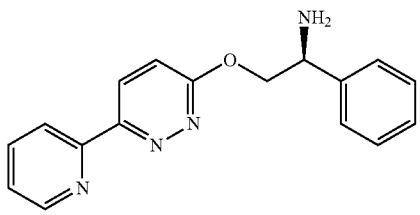 [SMILES: N[C@H](COc1ccc(-c2ccccn2)nn1)c1ccccc1]

¹H NMR (400 MHz, CDCl₃) δ 8.66 (ddd, J=4.8, 1.6, 0.8 Hz, 1H), 8.56 (dt, J=8.0, 0.8 Hz, 1H), 8.49 (d, J=9.3 Hz, 1H), 7.83 (td, J=7.9, 1.8 Hz, 1H), 7.48 (m, 2H), 7.40-7.28 (m, 4H), 7.11 (d, J=9.2 Hz, 1H), 4.79 (dd, J=10.4, 4.0 Hz, 1H), 4.60 (dd, J=10.4, 8.4 Hz, 1H), 4.52 (dd, J=8.4, 4.0 Hz, 1H), 1.74 (s, br, 2H). MS 293 (M+1).

Example 40. 3-(((6-(pyridin-2-yl)pyridazin-3-yl)oxy)methyl)isoquinoline

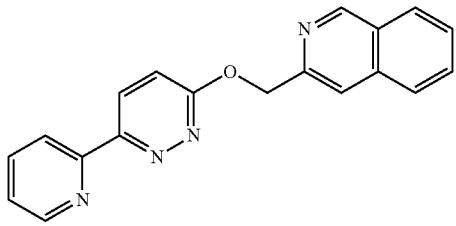 [SMILES: c1ccc(-c2ccc(OCc3cc4ccccc4cn3)nn2)nc1]

¹H NMR (400 MHz, CDCl₃) δ 9.32 (s, 1H), 8.67 (ddd, J=4.8, 1.7, 0.8 Hz, 1H), 8.58 (dt, J=8.0, 0.9 Hz, 1H), 8.53 (d, J=9.2 Hz, 1H), 8.01 (d, J=8.6 Hz, 1H), 7.91 (s, 1H), 7.86 (d, J=8.2 Hz, 1H), 7.84 (td, J=7.7, 1.7 Hz, 1H), 7.72 (t, J=8.0 Hz, 1H), 7.63 (t, J=8.1 Hz, 1H), 7.35 (ddd, J=1.1 Hz, 1H), 5.93 (s, 2H). MS 315 (M+1).

Example 41. 2-(((6-(pyridin-2-yl)pyridazin-3-yl)oxy)methyl)benzo[d]oxazole

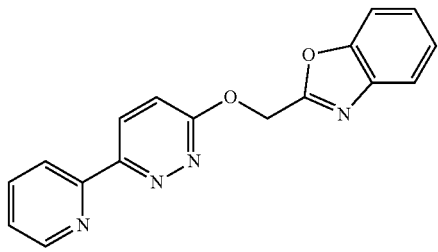 [SMILES: c1ccc(-c2ccc(OCc3nc4ccccc4o3)nn2)nc1]

¹H NMR (400 MHz, CDCl₃) δ 8.68 (d, br, J=4.7 Hz, 1H), 8.58 (d, J=9.2 Hz, 1H), 8.56 (dt, J=8.0, 0.8 Hz, 1H), 7.85 (td, J=7.6, 1.7 Hz, 1H), 7.76 (m, 1H), 7.57 (m, 1H), 7.40-7.33 (m, 3H), 7.29 (d, J=9.1 Hz, 1H), 5.91 (s, 2H). MS 305 (M+1).

Example 42. 3-(2-(1H-pyrazol-1-yl)ethoxy)-6-(pyridin-2-yl)pyridazine

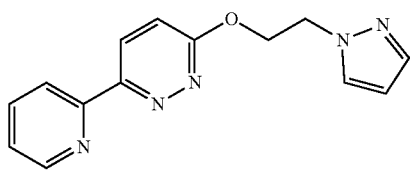 [SMILES: c1ccc(-c2ccc(OCCn3cccn3)nn2)nc1]

¹H NMR (400 MHz, CDCl₃) δ 8.67 (d, br, J=4.1 Hz, 1H), 8.55 (d, J=8.1 Hz, 1H), 8.49 (d, J=9.2 Hz, 1H), 7.84 (td, J=7.8, 1.7 Hz, 1H), 7.56 (d, J=1.6 Hz, 1H), 7.49 (d, J=2.2 Hz, 1H), 7.35 (ddd, J=7.6, 4.6, 1.0 Hz, 1H), 7.09 (d, J=9.2 Hz, 1H), 6.27 (t, J=2.1 Hz, 1H), 4.99 (t, J=5.3 Hz, 2H), 4.65 (t, J=5.2 Hz, 2H). MS 268 (M+1).

Example 43. 3-(pyridin-2-yl)-6-(2-(pyrrolidin-1-yl)ethoxy)pyridazine

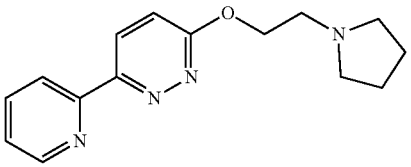 [SMILES: c1ccc(-c2ccc(OCCN3CCCC3)nn2)nc1]

¹H NMR (400 MHz, CDCl₃) δ 8.66 (ddd, J=4.8, 1.7, 0.9 Hz, 1H), 8.56 (dt, J=8.0, 1.0 Hz, 1H), 8.46 (d, J=9.2 Hz, 1H), 7.83 (td, J=7.8, 1.8 Hz, 1H), 7.33 (ddd, J=7.5, 4.9, 1.2 Hz, 1H), 7.13 (d, J=9.2 Hz, 1H), 4.73 (t, J=5.7 Hz, 2H), 2.98 (t, J=5.7 Hz, 2H), 2.64 (m, 4H), 1.82 (m, 4H). MS 271 (M+1).

Example 44. (1R,2R)-2-((6-(pyridin-2-yl)pyridazin-3-yl)oxy)cyclohexan-1-amine

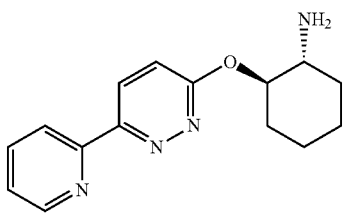 [SMILES: N[C@@H]1CCCC[C@H]1Oc1ccc(-c2ccccn2)nn1]

¹H NMR (400 MHz, CDCl₃) δ 8.62 (ddd, J=4.8, 1.8, 0.9 Hz, 1H), 8.46 (dt, J=8.1, 1.0 Hz, 1H), 8.28 (d, J=9.3 Hz, 1H), 7.79 (td, J=7.7, 1.8 Hz, 1H), 7.28 (ddd, J=7.4, 4.8, 1.1 Hz, 1H), 6.85 (d, J=9.3 Hz, 1H), 5.40 (s, br, 1H), 3.80 (m, 1H), 3.55 (ddd, J=10.7, 9.5, 4.5 Hz, 1H), 2.16 (m, 2H), 1.77 (m, 2H), 1.52-1.25 (m, 5H).

Example 45. 3-(3-(1H-imidazol-1-yl)propoxy)-6-(pyridin-2-yl)pyridazine

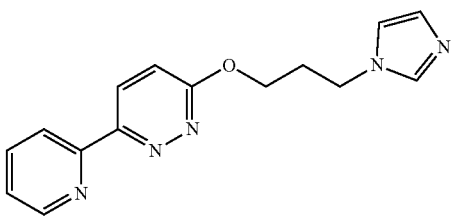 [SMILES: c1ccc(-c2ccc(OCCCn3ccnc3)nn2)nc1]

¹H NMR (400 MHz, CDCl₃) δ 8.67 (dd, J=4.7, 0.7 Hz, 1H), 8.55 (d, J=8.0 Hz, 1H), 8.51 (d, J=9.2 Hz, 1H), 7.84 (td, J=7.6, 1.8 Hz, 1H), 7.52 (s, 1H), 7.35 (ddd, J=7.6, 4.9, 1.1 Hz, 1H), 7.09 (d, J=9.3 Hz, 1H), 7.07 (s, 1H), 6.96 (t, J=1.0 Hz, 1H), 4.62 (t, J=6.0 Hz, 2H), 4.19 (t, J=7.0 Hz, 2H), 2.36 (quint, J=6.5 Hz, 2H). MS 282 (M+1).

Example 46. 3-(2-(1H-pyrrol-1-yl)ethoxy)-6-(pyridin-2-yl)pyridazine

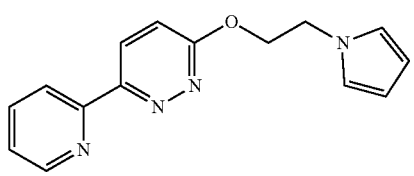 [SMILES: c1ccc(-c2ccc(OCCn3cccc3)nn2)nc1]

¹H NMR (400 MHz, CDCl₃) δ 8.67 (ddd, J=4.9, 1.8, 1.0 Hz, 1H), 8.56 (dt, J=8.0, 1.0 Hz, 1H), 8.51 (d, J=9.3 Hz, 1H), 7.85 (td, J=7.7, 1.8 Hz, 1H), 7.36 (ddd, J=7.5, 4.9, 1.2 Hz, 1H), 7.11 (d, J=9.2 Hz, 1H), 6.77 (t, J=2.1 Hz, 2H), 6.18 (t, J=2.1 Hz, 2H), 4.87 (t, J=5.4 Hz, 2H), 4.38 (t, J=5.4 Hz, 2H). MS 267 (M+1).

Example 47. 1-(2-((6-(pyridin-2-yl)pyridazin-3-yl)oxy)ethyl)-1H-benzo[d]imidazole

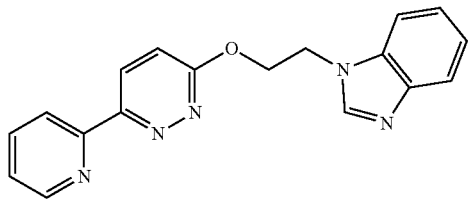 [SMILES: c1ccc(-c2ccc(OCCn3cnc4ccccc43)nn2)nc1]

¹H NMR (400 MHz, CDCl₃) δ 8.67 (d, J=4.8 Hz, 1H), 8.53 (d, J=8.0 Hz, 1H), 8.50 (d, J=9.3 Hz, 1H), 8.03 (s, 1H), 7.84 (m, 2H), 7.49 (dd, J=7.1, 1.5 Hz, 1H), 7.38-7.28 (m, 3H), 7.06 (d, J=9.2 Hz, 1H), 4.98 (t, J=5.3 Hz, 2H), 4.70 (t, J=5.3 Hz, 2H). MS 318 (M+1).

Example 48. 1-(2-((6-(pyridin-2-yl)pyridazin-3-yl)oxy)ethyl)-1H-pyrrole-2,5-dione

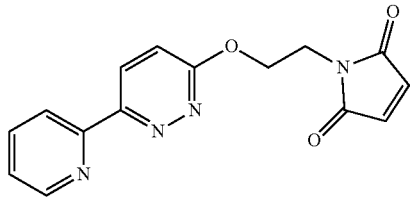 [SMILES: O=C1C=CC(=O)N1CCOc1ccc(-c2ccccn2)nn1]

¹H NMR (400 MHz, CDCl₃) δ 8.65 (ddd, J=4.8, 1.5, 1.0 Hz, 1H), 8.45 (d, J=9.8 Hz, 1H), 8.08 (d, J=8.1 Hz, 1H), 7.80 (td, J=7.8, 1.7 Hz, 1H), 7.35 (ddd, J=7.6, 4.8, 1.1 Hz, 1H), 7.07 (d, J=9.7 Hz, 1H), 3.94-3.79 (m, 4H), 3.28 (dd, J=18.2, 9.5 Hz, 1H), 3.09 (dd, J=18.2, 5.0 Hz, 1H). MS 315 (M+1+H₂O).

Example 49. 2-methyl-1-(2-((6-(pyridin-2-yl)pyridazin-3-yl)oxy)ethyl)-1H-benzo[d]imidazole

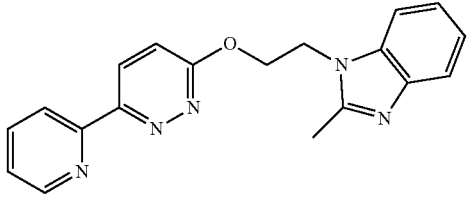 [SMILES: Cc1nc2ccccc2n1CCOc1ccc(-c2ccccn2)nn1]

¹H NMR (400 MHz, CDCl₃) δ 8.55 (ddd, J=4.9, 1.6, 1.0 Hz, 1H), 8.25 (d, J=9.7 Hz, 1H), 7.62 (m, 2H), 7.33 (m, 2H), 7.26-7.14 (m, 3H), 7.01 (d, J=9.7 Hz, 1H), 4.62 (m, 4H), 2.55 (s, 3H). MS 332 (M+1).

Example 50. 3-(2-(1H-imidazol-1-yl)ethoxy)-6-(pyridin-2-yl)pyridazine

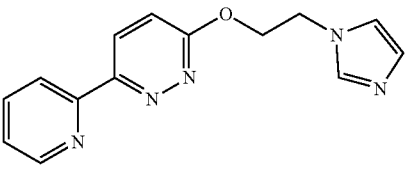 [SMILES: c1ccc(-c2ccc(OCCn3ccnc3)nn2)nc1]

¹H NMR (400 MHz, CDCl₃) δ 8.67 (ddd, J=4.8, 1.6, 0.8 Hz, 1H), 8.54 (dt, J=8.0, 1.0 Hz, 1H), 8.52 (d, J=9.2 Hz, 1H), 7.85 (td, J=7.8, 1.8 Hz, 1H), 7.59 (s, 1H), 7.35 (ddd, J=7.5, 4.8, 1.1 Hz, 1H), 7.11 (d, J=9.2 Hz, 1H), 7.08 (t, J=1.2 Hz, 1H), 7.04 (t, J=1.2 Hz, 1H), 4.87 (t, J=5.4 Hz, 2H), 4.45 (t, J=5.2 Hz, 2H). MS 268 (M+1).

Example 51. (R)-3-(2-methoxy-2-phenylethoxy)-6-(pyridin-2-yl)pyridazine

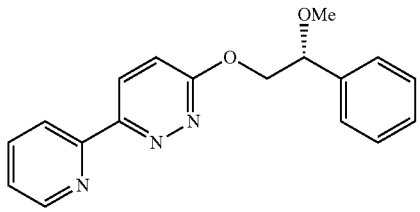 [SMILES: CO[C@@H](COc1ccc(-c2ccccn2)nn1)c1ccccc1]

¹H NMR (400 MHz, CDCl₃) δ 8.66 (ddd, J=4.8 1.7, 0.9 Hz, 1H), 8.55 (td, J=8.1, 1.0 Hz, 1H), 8.47 (d, J=9.2 Hz, 1H), 7.83 (td, J=7.6, 1.7 Hz, 1H), 7.46-7.27 (m, 6H), 7.15 (d, J=9.2 Hz, 1H), 4.73 (m, 2H), 3.65 (m, 1H), 3.35 (s, 3H). MS 308 (M+1).

Example 52. 1-(2-((6-(pyridin-2-yl)pyridazin-3-yl)oxy)ethyl)pyrrolidin-2-one

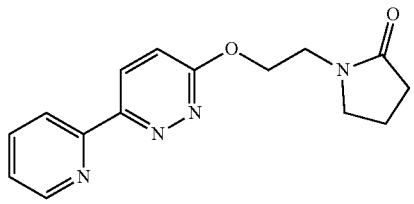 [SMILES: O=C1CCCN1CCOc1ccc(-c2ccccn2)nn1]

¹H NMR (400 MHz, CDCl₃) δ 8.66 (ddd, J=4.8, 1.7, 0.9 Hz, 1H), 8.55 (dt, J=8.0, 0.9 Hz, 1H), 8.48 (d, J=9.2 Hz, 1H), 7.83 (td, J=7.7, 1.8 Hz, 1H), 7.34 (ddd, J=7.5, 4.9, 1.2 Hz, 1H), 7.09 (d, J=9.2 Hz, 1H), 4.62 (t, J=6.2 Hz, 2H), 3.51 (t, J=7.1 Hz, 2H), 3.44 (t, J=7.1 Hz, 2H), 2.39 (t, J=7.9 Hz, 2H), 2.13 (m, 2H), 2.04 (m, 2H). MS 285 (M+1).

Example 53. (1S,2S)-2-((6-(pyridin-2-yl)pyridazin-3-yl)oxy)cyclohexan-1-amine

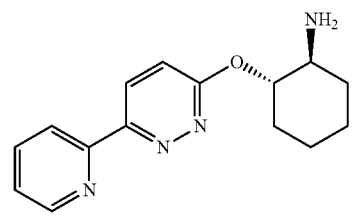 [SMILES: N[C@H]1CCCC[C@@H]1Oc1ccc(-c2ccccn2)nn1]

¹H NMR (400 Hz, DMSO) δ: 2.38 (m, 1H), 2.10 (m, 1H), 1.75 (m, 2H), 1.30-1.55 (m, 4H), 5.23-5.30 (m, 1H), 7.33 (d, J=9 Hz, 1H), 7.50 (ddd, J=8 Hz, 5 Hz, 1 Hz, 1H), 7.99 (td, J=8 Hz, 2 Hz, 1H), 8.42 (d, J=8 Hz, 1H), 8.48 (d, J=9 Hz, 1H), 8.71 (d, J=4 Hz, 1H). MS 271 (M+1).

Example 54. (R)-3-((1-methylpyrrolidin-3-yl)oxy)-6-(pyridin-2-yl)pyridazine

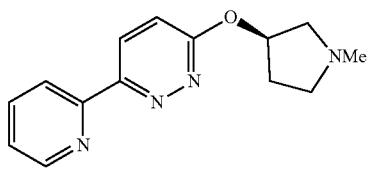 [SMILES: CN1CC[C@@H](Oc2ccc(-c3ccccn3)nn2)C1]

¹H NMR (400 Hz, CDCl₃) δ: 2.03-2.14 (m, 1H), 2.33-2.40 (m, 1H), 2.41 (s, 3H), 2.46-2.56 (m, 1H), 2.77-2.84 (m, 1H), 2.91-3.03 (m, 2H), 5.71-5.77 (m, 1H), 7.09 (d, J=9 Hz, 1H), 7.30-7.35 (m, 1H), 7.82 (td, J=8 Hz, 2 Hz, 1H), 8.46 (d, J=9 Hz, 1H), 8.56 (d, J=8 Hz, 1H), 8.66 (d, J=5 Hz, 1H). MS 257 (M+1).

Example 55. (1R,2R)—N,N-dimethyl-2-((6-(pyridin-2-yl)pyridazin-3-yl)oxy)cyclopentan-1-amine

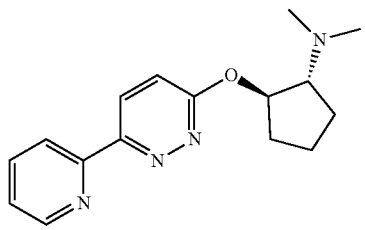 [SMILES: CN(C)[C@@H]1CCC[C@H]1Oc1ccc(-c2ccccn2)nn1]

¹H NMR (400 Hz, CDCl₃) δ: 1.57-1.85 (m, 4H), 1.98-2.07 (m, 1H), 2.35 (s, 6H), 2.95-3.07 (m, 2H), 5.63-5.70 (m, 1H), 7.06 (d, J=9.2 Hz, 1H), 7.33 (ddd, J=8 Hz, 5 Hz, 1 Hz, 1H), 7.83 (td, J=8 Hz, 2 Hz, 1H), 8.46 (d, J=9 Hz, 1H), 8.57 (dt, J=8 Hz, 1 Hz, 1H), 8.66 (ddd, J=5 Hz, 2 Hz, 1 Hz, 1H). MS 284 (M+1).

Example 56. 3-(piperidin-3-yloxy)-6-(pyridin-2-yl)pyridazine

¹H NMR (400 Hz, CDCl₃) δ: 1.52-1.64 (m, 1H), 1.80-1.96 (m, 2H), 2.10-2.20 (m, 1H), 2.78-2.94 (m, 2H), 2.80-3.05 (m, 1H), 3.26-3.32 (m, 1H), 5.35-5.42 (m, 1H), 7.09 (d, J=9 Hz, 1H), 7.33 (ddd, J=7 Hz, 5 Hz, 1 Hz, 1H), 7.83 (td, J=8 Hz, 2 Hz, 1H), 8.47 (d, J=9 Hz, 1H), 8.56 (dt, J=8 Hz, 1 Hz, 1H), 8.66 (ddd, J=5 Hz, 2 Hz, 1 Hz, 1H). MS 257 (M+1).

Example 57. (1S,2S)—N,N-dimethyl-2-((6-(pyridin-2-yl)pyridazin-3-yl)oxy)cyclohexan-1-amine

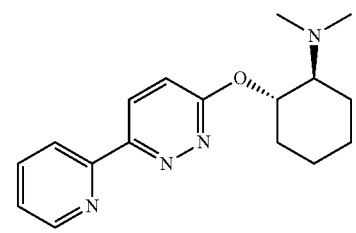 [SMILES: CN(C)[C@H]1CCCC[C@@H]1Oc1ccc(-c2ccccn2)nn1]

¹H NMR (400 Hz, CDCl₃) δ: 1.20-1.47 (m, 5H), 1.70-1.85 (m, 2H), 1.89-1.98 (m, 1H), 2.36 (s, 6H), 2.73-2.82 (m, 1H), 5.55-5.64 (m, 1H), 7.09 (d, J=9 Hz, 1H), 7.33 (ddd, J=8 Hz, 5 Hz, 1 Hz, 1H), 7.83 (td, J=8 Hz, 2 Hz, 1H), 8.46 (d, J=9 Hz, 1H), 8.57 (dt, J=8 Hz, 1 Hz, 1H), 8.66 (ddd, J=5 Hz, 2 Hz, 1 Hz, 1H). MS 299 (M+1).

Example 58.
N-benzyl-6-(pyridin-2-yl)pyridazin-3-amine

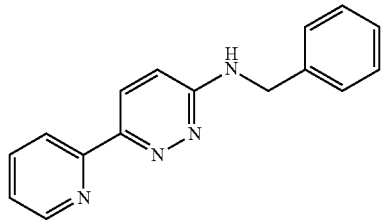 [SMILES: c1ccc(CNc2ccc(-c3ccccn3)nn2)cc1]

A mixture of 1,4-dioxane (5 cm³), benzylamine (147 mg, 1.4 mmol), potassium bis-(trimethylsilyl)amide (KHMDS, 263.1 mg, 1.3 mmol) and 3-chloro-6-(2-pyridinyl)pyridazine (97.0 mg, 0.5 mmol) was purged with argon for 10-15 minutes. Brett-phos (13.7 mg, 1.5 mol %) was added and the reaction mixture was stirred and heated at 100° C. for three days. The solution was cooled, saturated aqueous NaHCO₃ (10 cm³) and dichloromethane (DCM, 25 cm³) were added, and the phases were separated. The aqueous phase was extracted twice with DCM (25 cm³), and the organic phases were combined, dried over Na₂SO₄, and filtered. Removal of the solvent in vacuo gave a yellow solid. The compound was purified using a silica column from ethyl acetate and triethylamine (99:1) to give the desired compound (53 mg, 40%). ¹H NMR (400 MHz, CDCl₃) δ 8.62 (ddd, J=4.8, 1.8, 0.9 Hz, 1H), 8.53 (dt, J=8.0, 1.0 Hz, 1H), 8.27 (d, J=9.3 Hz, 1H), 7.79 (td, J=7.6, 1.8 Hz, 1H), 7.43-7.27 (m, 6H), 6.75 (d, J=9.3 Hz, 1H), 5.15 (br, t, J=5.3 Hz, 1H), 4.73 (d, J=5.7 Hz, 2H). MS 263 (M+1).

Example 59. N-(2-(dimethylamino)ethyl)-N-(6-(pyridin-2-yl)pyridazin-3-yl)benzamide

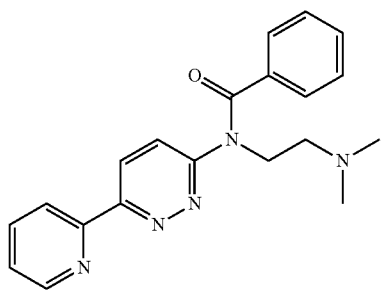 [SMILES: CN(C)CCN(C(=O)c1ccccc1)c1ccc(-c2ccccn2)nn1]

Step 1. N1,N1-dimethyl-N2-(6-(pyridin-2-yl)pyridazin-3-yl)ethane-1,2-diamine

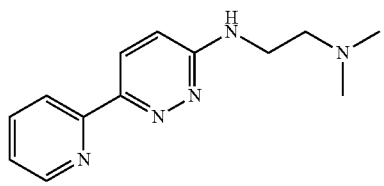 [SMILES: CN(C)CCNc1ccc(-c2ccccn2)nn1]

3-Chloro-6-(2-pyridinyl)pyridazine (99.6 mg, 0.52 mmol), ammonium chloride (31.1 mg, 0.58 mmol) and N,N-dimethylethylenediamine (275 µl, 2.51 mmol) in 1-butanol (5 cm³) were heated to 130° C. for 24 hours. The solvent was removed in vacuo and to the residue was added ethyl acetate: H₂O (2:1, 5 cm³). The aqueous layer was extracted with EtOAc (2×5 cm³) and the organic fractions combined and dried over Na₂SO₄. The reaction mixture was filtered and concentrated in vacuo. The compound was purified using a silica column from ethyl acetate, methanol, and triethylamine (8:2:2) to give the desired compound (61 mg, 50%). ¹H NMR (400 MHz, CDCl₃) δ 8.60 (ddd, J=4.8, 1.7, 0.9 Hz, 1H), 8.51 (dt, J=8.1, 1.0 Hz, 1H), 8.23 (d, J=9.3 Hz, 1H), 7.77 (td, J=7.6, 1.7 Hz, 1H), 7.25 (ddd, J=7.5, 4.9, 1.2 Hz, 1H), 6.76 (d, J=9.4 Hz, 1H), 5.45 (br, t, J=5.2 Hz, 1H), 3.60 (q, J=5.3 Hz, 2H), 2.61 (t, J=5.8 Hz, 2H), 2.28 (s, 6H). MS 244 (M+1).

Step 2. N-(2-(dimethylamino)ethyl)-N-(6-(pyridin-2-yl)pyridazin-3-yl)benzamide

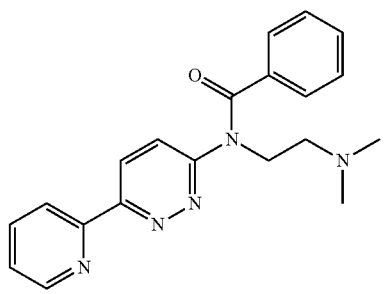 [SMILES: CN(C)CCN(C(=O)c1ccccc1)c1ccc(-c2ccccn2)nn1]

The N1,N1-dimethyl-N2-(6-(pyridin-2-yl)pyridazin-3-yl)ethane-1,2-diamine from Step 1 (40.2 mg, 0.17 mmol), DMAP (4.5 mg, 0.037 mmol) and triethylamine (41.8 µL, 0.3 mmol) were dissolved in dichloromethane (1 cm³) and cooled to 0° C. Benzoyl chloride (46.5 µL, 0.4 mmol) was added dropwise to the stirring solution. The reaction mixture was slowly warmed to room temperature with stirring for 5 hours. To the solution was added DCM (2 cm³) and sat. aqueous NH₄C₁ (1 cm³) and the organic layer was extracted. The aqueous layer was extracted with DCM (2×2 cm³) and the organic fractions were combined, dried over Na₂SO₄, filtered, and evaporated under reduced pressure. The resulting residue was purified using a basic alumina column from dichloromethane and methanol (95:5) and gave a yellow solid (34.7 mg, 59%). ¹H NMR (400 MHz, CDCl₃) δ 8.65-8.62 (m, 2H), 8.25 (d, 1H, J=9.0 Hz), 7.86 (td, 1H, J=8.0, 2.0 Hz), 7.43 (brs, 1H), 7.41 (m, 1H), 7.38-7.32 (m, 2H), 7.28-7.24 (m, 2H), 7.11 (d, 1H, J=9.0 Hz), 4.40 (t, 2H, J=7.0 Hz), 2.70 (t, 2H, J=7.0 Hz), 2.18 (s, 6H), MS 348 (M+1).

The compounds of Example 60-65 were prepared according to the procedures described in Example 58 or Example 59, using the appropriate starting materials.

Example 60. N$^1$,N$^1$-dimethyl-N$^3$-(6-(pyridin-2-yl)pyridazin-3-yl)propane-1,3-diamine

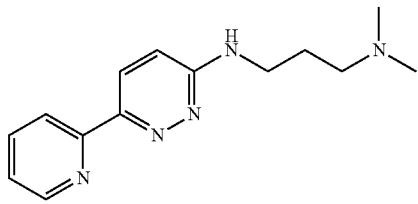 [SMILES: CN(C)CCCNc1ccc(-c2ccccn2)nn1]

$^1$H NMR (400 MHz, CDCl$_3$) δ 8.61 (brd, 1H, J=4.5 Hz), 8.52 (brd, 1H, J=8.0 Hz), 8.23 (d, 1H, J=9.5 Hz), 7.78 (td, 1H, J=8.0, 1.5 Hz), 7.27-7.24 (m, 1H), 6.72 (d, 1H, J=9.5 Hz), 6.09 (s, 1H), 3.57 (q, 2H, J=6.0 Hz), 2.45 (t, 2H, J=6.5 Hz), 2.26 (s, 6H), 1.84 (quint, 2H, J=6.5 Hz). MS 258 (M+1).

Example 61. N$^1$,N$^1$,N$^3$-trimethyl-N$^3$-(6-(pyridin-2-yl)pyridazin-3-yl)propane-1,3-diamine

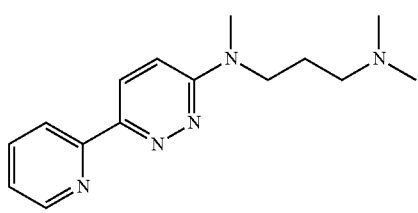 [SMILES: CN(C)CCCN(C)c1ccc(-c2ccccn2)nn1]

$^1$H NMR (400 MHz, CDCl$_3$) δ 8.61 (brd, 1H, J=5.0 Hz), 8.54 (brd, 1H, J=8.0 Hz), 8.26 (d, 1H, J=9.5 Hz), 7.78 (td, 1H, J=8.0, 2.0 Hz), 7.24 (ddd, 1H, J=7.5, 5.0, 1.0 Hz), 6.95 (d, 1H, J=10.0 Hz), 3.70 (t, 2H, J=7.0 Hz), 3.21 (s, 3H), 2.31 (t, 2H, J=7.0 Hz), 2.22 (s, 6H), 1.83 (quint, 2H, J=7.0 Hz). MS 272 (M+1).

Example 62. N-(3-(1H-imidazol-1-yl)propyl)-6-(pyridin-2-yl)pyridazin-3-amine

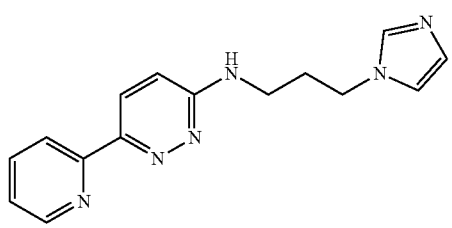 [SMILES: c1ccc(-c2ccc(NCCCn3ccnc3)nn2)nc1]

$^1$H NMR (400 MHz, CDCl$_3$) δ 8.62 (ddd, J=4.9, 1.8, 1.0 Hz, 1H), 8.50 (dt, J=8.0, 1.0 Hz, 1H), 8.26 (d, J=9.3 Hz, 1H), 7.79 (td, J=7.6, 1.8 Hz, 1H), 7.51 (s, 1H), 7.28 (ddd, J=7.4, 4.8, 1.1 Hz, 1H), 7.07 (s, 1H), 6.95 (s, 1H), 6.73 (d, J=9.3 Hz, 1H), 5.16 (br, t, J=5.5 Hz, 1H), 4.11 (t, J=7.0 Hz, 2H), 3.55 (q, J=6.6 Hz, 2H), 2.23 (quint, J=6.9 Hz, 2H). MS 281 (M+1).

Example 63. N$^1$,N$^1$,N$^2$-trimethyl-N$^2$-(6-(pyridin-2-yl)pyridazin-3-yl)ethane-1,2-diamine

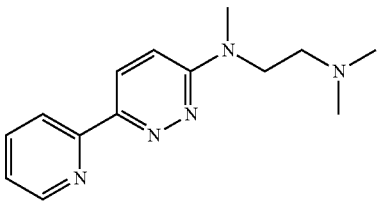 [SMILES: CN(C)CCN(C)c1ccc(-c2ccccn2)nn1]

$^1$H NMR (CDCl$_3$, 400 MHz): δ 8.60 (brd, 1H, J=5.0 Hz), 8.53 (brd, 1H, J=8.0 Hz), 8.26 (d, 1H, J=9.5 Hz), 7.76 (td, 1H, J=8.0, 1.5 Hz), 7.24 (ddd, 1H, J=7.5, 5.0, 1.0 Hz), 6.88 (d, 1H, J=9.5 Hz), 3.81 (t, 2H, J=14.0 Hz), 3.20 (s, 3H), 2.58 (t, 2H, J=14.0 Hz), 2.30 (s, 6H), MS 258 (M+1).

Example 64. N-(3-(dimethylamino)propyl)-N-(6-(pyridin-2-yl)pyridazin-3-yl)benzamide

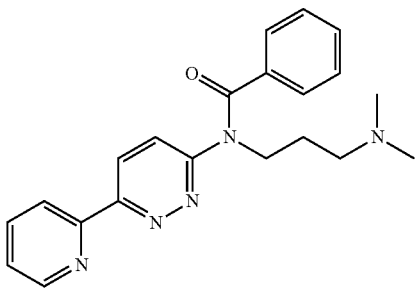 [SMILES: CN(C)CCCN(C(=O)c1ccccc1)c1ccc(-c2ccccn2)nn1]

$^1$H NMR (CDCl$_3$, 400 MHz): δ 8.62 (m, 2H), 8.27 (brd, 1H, J=8.5 Hz), 7.85 (brt, 1H, J=7.5 Hz), 7.42-7.26 (m, 6H), 7.13 (d, 1H, J=8.5 Hz), 4.32 (t, 2H, J=6.5 Hz), 2.36 (t, 2H, J=6.5 Hz), 2.16 (s, 6H), 1.97-1.91 (m, 2H). MS 362 (M+1).

Example 65. N-(3-(dimethylamino)propyl)-4-fluoro-N-(6-(pyridin-2-yl)pyridazin-3-yl)benzamide

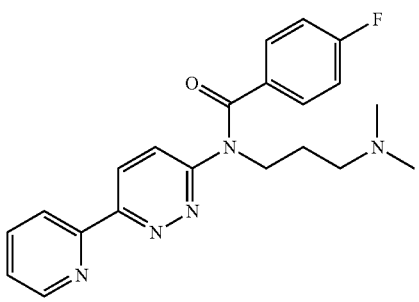 [SMILES: CN(C)CCCN(C(=O)c1ccc(F)cc1)c1ccc(-c2ccccn2)nn1]

$^1$H NMR (CDCl$_3$, 400 MHz): δ 8.66 (d, 1H, J=5.0 Hz), 8.62 (d, 1H, J=8.0 Hz), 8.33 (d, 1H, J=9.0 Hz), 7.86 (td, 1H, J=8.0, 2.0 Hz), 7.44-7.41 (m, 2H), 7.37 (ddd, 1H, J=7.5, 5.0, 1.0 Hz), 7.15 (d, 1H, J=9.0 Hz), 6.97-6.92 (m, 2H), 4.30 (t, 2H, J=7.5 Hz), 2.36 (t, 2H, J=7.0 Hz), 2.17 (s, 6H), 1.95 (quint, 2H, J=7.5 Hz). MS 380 (M+1).

Example 66. EAAT2 Cellular Assay

All of the compounds were initially evaluated in PA-EAAT2 cells, a primary astrocyte stably expressing human EAAT2 mRNAs (Kong et al., *J Clin Invest.* 2014:1255-67). Cells were treated with compound at 0.25 µM, 0.5 µM, 1 µM, 2.5 µM, 5 µM, 10 µM, and 25 µM for 24 hr and then harvested for measuring EAAT2 protein levels by Western blot analysis. Table 1 shows the fold increases in EAAT2 protein levels relative to DMSO controls at indicated concentration that reaches maximum activity.

TABLE 1

| Structure | Fold increase for EAAT2 at indicated concentration (maximum activity) |
|---|---|
| [structure] | 2.5 ± 0.3 (0.25 µM) |
| [structure] | 2.1 ± 0.2 (10 µM) |
| [structure] | 1.9 ± 0.1 (2.5 µM) |
| [structure] | 2.9 ± 0.2 (2.5 µM) |
| [structure] | 3.0 ± 0.1 (5 µM) |

TABLE 1-continued

| Structure | Fold increase for EAAT2 at indicated concentration (maximum activity) |
|---|---|
| [structure] | 1.8 ± 0.2 (10 µM) |
| [structure] | 2.6 ± 0.2 (0.25 µM) |
| [structure] | 2.4 ± 0.2 (0.5 µM) |
| [structure] | 1.7 ± 0.1 (0.5 µM) |
| [structure] | 1.5 ± 0.1 (0.5 µM) |
| [structure] | 1.9 ± 0.1 (0.5 µM) |

TABLE 1-continued
| Structure | Fold increase for EAAT2 at indicated concentration (maximum activity) |
|---|---|
| 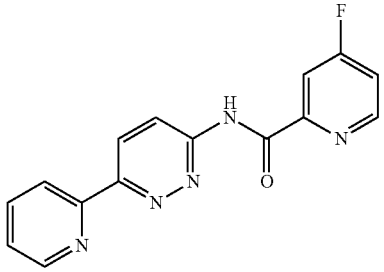 [SMILES: O=C(Nc1ccc(-c2ccccn2)nn1)c1cc(F)ccn1] | 1.7 ± 0.1 (0.25 µM) |
| 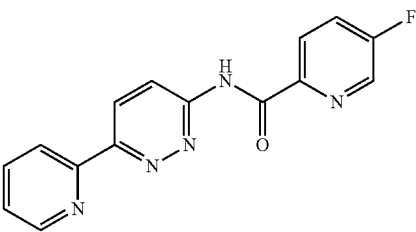 [SMILES: O=C(Nc1ccc(-c2ccccn2)nn1)c1ccc(F)cn1] | 1.9 ± 0.2 (0.25 µM) |
| 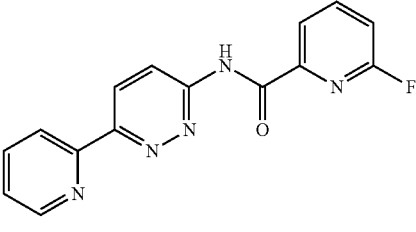 [SMILES: O=C(Nc1ccc(-c2ccccn2)nn1)c1cccc(F)n1] | 1.6 ± 0.1 (0.25 µM) |
| 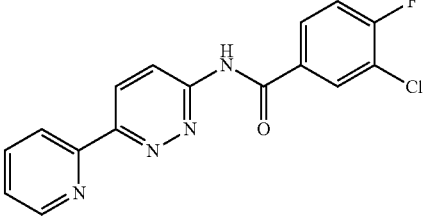 | 2.2 ± 0.4 (0.25 µM) |
| 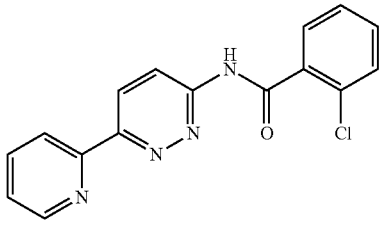 [SMILES: O=C(Nc1ccc(-c2ccccn2)nn1)c1ccccc1Cl] | 2.0 ± 0.2 (5 µM) |
| 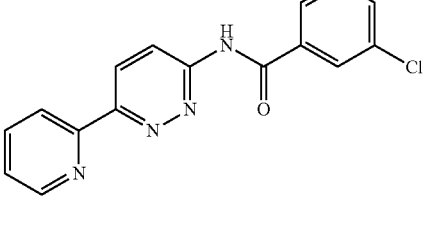 | 1.5 ± 0.1 (1 µM) |
TABLE 1-continued
| Structure | Fold increase for EAAT2 at indicated concentration (maximum activity) |
|---|---|
| 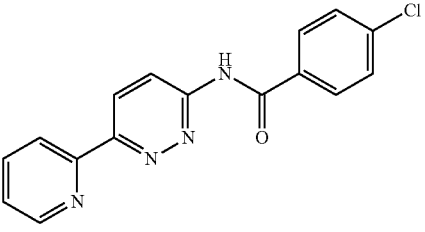 [SMILES: O=C(Nc1ccc(-c2ccccn2)nn1)c1ccc(Cl)cc1] | 1.5 ± 0.2 (1 µM) |
| 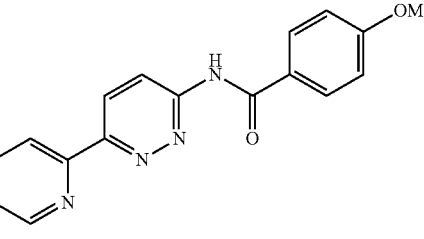 | 2.1 ± 0.2 (10 µM) |
| 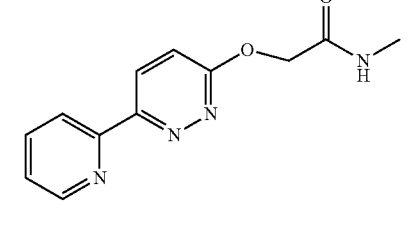 | 2.3 ± 0.1 (0.25 µM) |
| 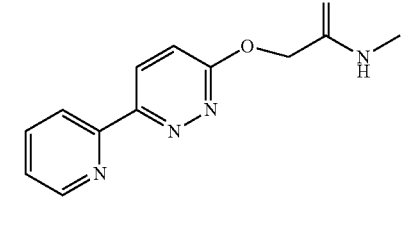 | 1.8 ± 0.1 (10 µM) |
| 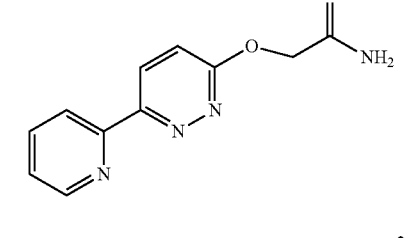 | 1.8 ± 0.2 (10 µM) |
| 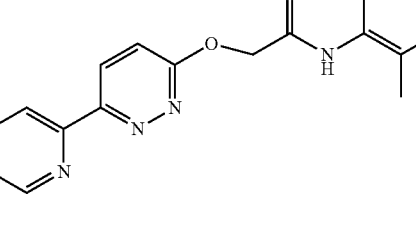 | 2.4 ± 0.2 (10 µM) |

TABLE 1-continued

| Structure | Fold increase for EAAT2 at indicated concentration (maximum activity) |
|---|---|
| (pyridine-pyridazine-O-CH2-C(=O)-N(Me)-phenyl) | 2.2 ± 0.3 (10 μM) |
| (pyridine-pyridazine-O-CH2-C(=O)-piperidine) | 2.6 ± 0.1 (10 μM) |
| (pyridine-pyridazine-O-CH2-C(=O)-N(Me)2) | 2.9 ± 0.2 (5 μM) |
| (pyridine-pyridazine-NH-C(=O)-thiazole) | 1.9 ± 0.1 (5 μM) |
| (pyridine-pyridazine-O-CH2-thiazole) | 2.2 ± 0.3 (10 μM) |
| (pyridine-pyridazine-O-CH2-N-methylimidazole) | 1.7 ± 0.1 (5 μM) |
| (pyridine-pyridazine-O-CH2-N-methylimidazole isomer) | 1.9 ± 0.1 (5 μM) |
| (pyridine-pyridazine-O-CH(Me)-pyridine) | 1.7 ± 0.1 (5 μM) |
| (pyridine-pyridazine-NH-CH2CH2-N(Me)2) | 2.4 ± 0.2 (5 μM) |
| (pyridine-pyridazine-NH-CH2-phenyl) | 3.1 ± 0.3 (10 μM) |
| (pyridine-pyridazine-NH-CH2CH2CH2-imidazole) | 3.3 ± 0.2 (5 μM) |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

It is further appreciated that certain features of the invention, which are, for clarity, described in the context of separate embodiments, can also be provided in combination in a single embodiment. Conversely, various features of the

What is claimed is:

1. A compound of Formula (11a):

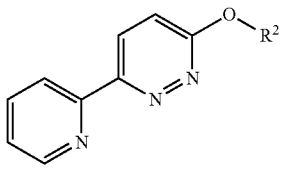

or a pharmaceutically acceptable salt thereof, wherein:
$R^2$ is —$(CHR^E)_nR^5$;
$R^5$ is selected from one of the following:
(i) $NR^CR^D$, wherein $R^C$ is selected from $C_{1-6}$ alkyl and $R^D$ is selected from H and $C_{1-6}$ alkyl, or $R^C$ and $R^D$ attached to the same N atom, together with the N atom to which they are attached, form a 4-6 membered heterocycloalkyl group;
(ii) $C(O)NR^CR^D$, wherein $R^C$ is selected from $C_{1-6}$ alkyl and 6-10 membered aryl optionally substituted with 1, 2, 3, or 4 independently selected $R^6$ groups, and $R^D$ is selected from H, $C_{1-6}$ alkyl, and 6-10 membered aryl optionally substituted with 1, 2, 3, or 4 independently selected $R^6$ groups; or $R^C$ and $R^D$ attached to the same N atom, together with the N atom to which they are attached, form a 4-6 membered heterocycloalkyl group optionally substituted with 1, 2, or 3 independently selected $R^6$ groups; or
(iii) $C(O)OR^C$, wherein $R^C$ is $C_{1-6}$ alkyl;
$R^E$ is selected from the group consisting of H, $C_{1-6}$ alkyl, $C_{1-6}$ alkoxy, and amino, wherein said $C_{1-6}$ alkyl is optionally substituted by 1, 2, 3, or 4 independently selected $R^6$ groups;
each $R^6$ is independently selected from OH, $NO_2$, CN, halo, $C_{1-6}$ alkyl, $C_{2-6}$ alkenyl, $C_{2-6}$ alkynyl, $C_{1-4}$ haloalkyl, $C_{1-6}$ alkoxy, $C_{1-6}$ haloalkoxy, cyano-$C_{1-3}$ alkyl, HO—$C_{1-3}$ alkyl, amino, $C_{1-6}$ alkylamino, di($C_{1-6}$ alkyl)amino, thio, $C_{1-6}$ alkylthio, $C_{1-6}$ alkylsulfinyl, $C_{1-6}$ alkylsulfonyl, carbamyl, $C_{1-6}$ alkylcarbamyl, di($C_{1-6}$ alkyl)carbamyl, carboxy, $C_{1-6}$ alkylcarbonyl, $C_{1-6}$ alkoxycarbonyl, $C_{1-6}$ alkylcarbonylamino, $C_{1-6}$ alkylsulfonylamino, aminosulfonyl, $C_{1-6}$ alkylaminosulfonyl, di($C_{1-6}$ alkyl)aminosulfonyl, aminosulfonylamino, $C_{1-6}$ alkylaminosulfonylamino, di($C_{1-6}$ alkyl)aminosulfonylamino, aminocarbonylamino, $C_{1-6}$ alkylaminocarbonylamino, and di($C_{1-6}$alkyl)aminocarbonylamino; and
n is 0, 1, 2, 3, 4, or 5.

2. The compound of claim 1, wherein $R^5$ is $NR^CR^D$, $R^C$ is selected from $C_{1-6}$ alkyl, and $R^D$ is selected from H and $C_{1-6}$ alkyl.

3. The compound of claim 2, wherein $R^C$ and $R^D$ are $CH_3$.

4. The compound of claim 1, wherein $R^5$ is $C(O)NR^CR^D$, wherein $R^C$ is selected from $C_{1-6}$ alkyl and 6-10 membered aryl optionally substituted with 1, 2, 3, or 4 independently selected $R^6$ groups, and $R^D$ is selected from H, $C_{1-6}$ alkyl, and 6-10 membered aryl optionally substituted with 1, 2, 3, or 4 independently selected $R^6$ groups; or $R^C$ and $R^D$ attached to the same N atom, together with the N atom to which they are attached, form a 4-6 membered heterocycloalkyl group optionally substituted with 1, 2, or 3 independently selected $R^6$ groups.

5. The compound of claim 4, wherein $R^C$ is selected from $C_{1-6}$ alkyl, and $R^D$ is selected from H and $C_{1-6}$ alkyl.

6. The compound of claim 4, wherein $R^C$ is selected from $C_{1-6}$ alkyl and phenyl optionally substituted with $C_{1-6}$ alkyl, and $R^D$ is selected from H, $C_{1-6}$ alkyl, and phenyl optionally substituted with $C_{1-6}$ alkyl.

7. The compound of claim 1, wherein $R^5$ is $NR^CR^D$, and $R^C$ and $R^D$ attached to the same N atom, together with the N atom to which they are attached, form a 4-6 membered heterocycloalkyl group.

8. The compound of claim 1, wherein $R^5$ is $C(O)OR^C$, wherein $R^C$ is $C_{1-6}$ alkyl.

9. The compound of claim 1, wherein n is 1 or 2.

10. A compound selected from the group consisting of:

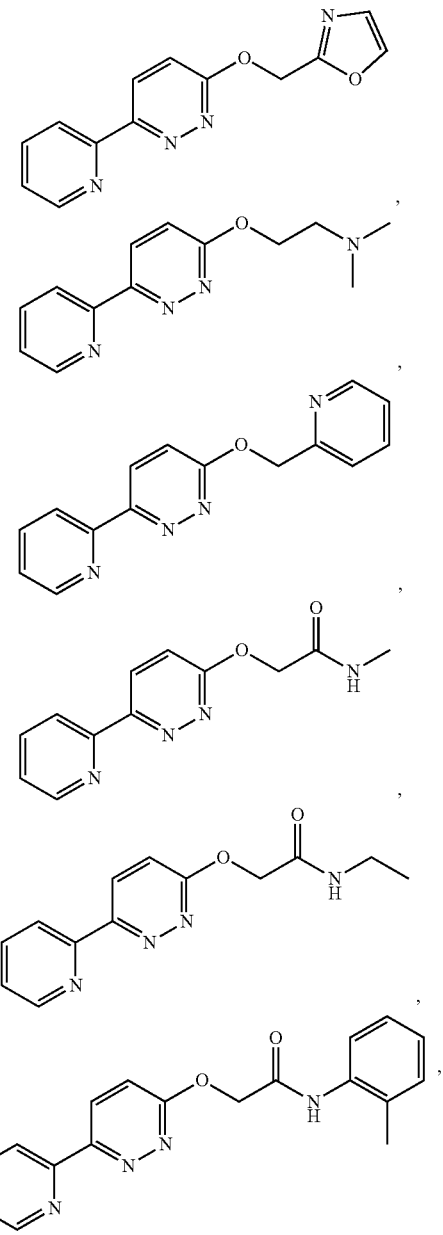

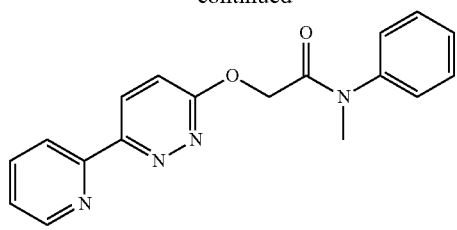
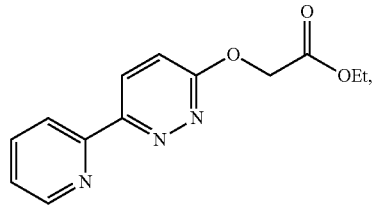
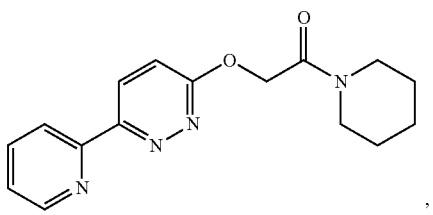
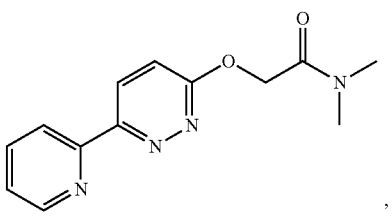
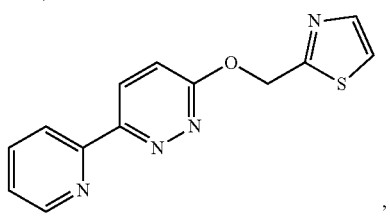
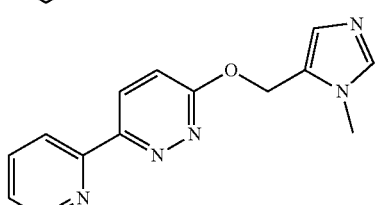
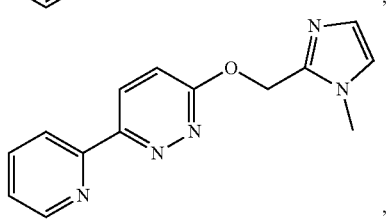
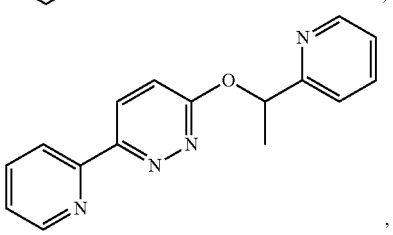
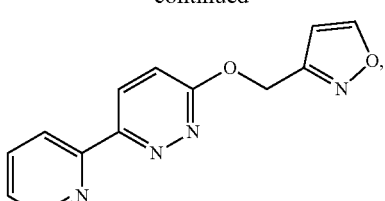
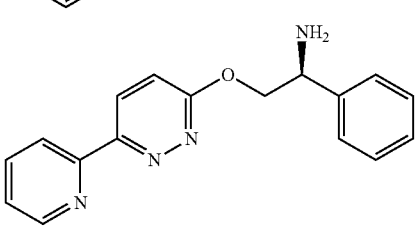
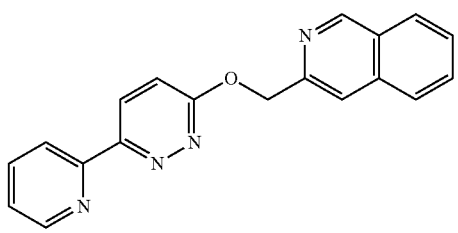
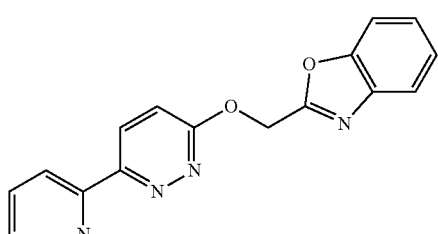
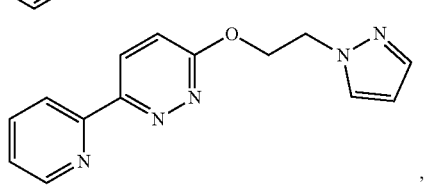
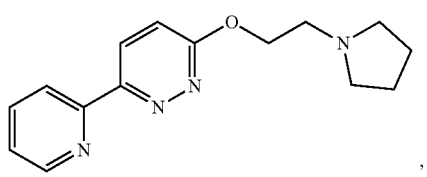
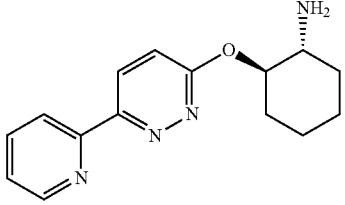
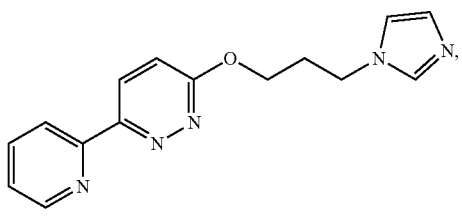

99
-continued
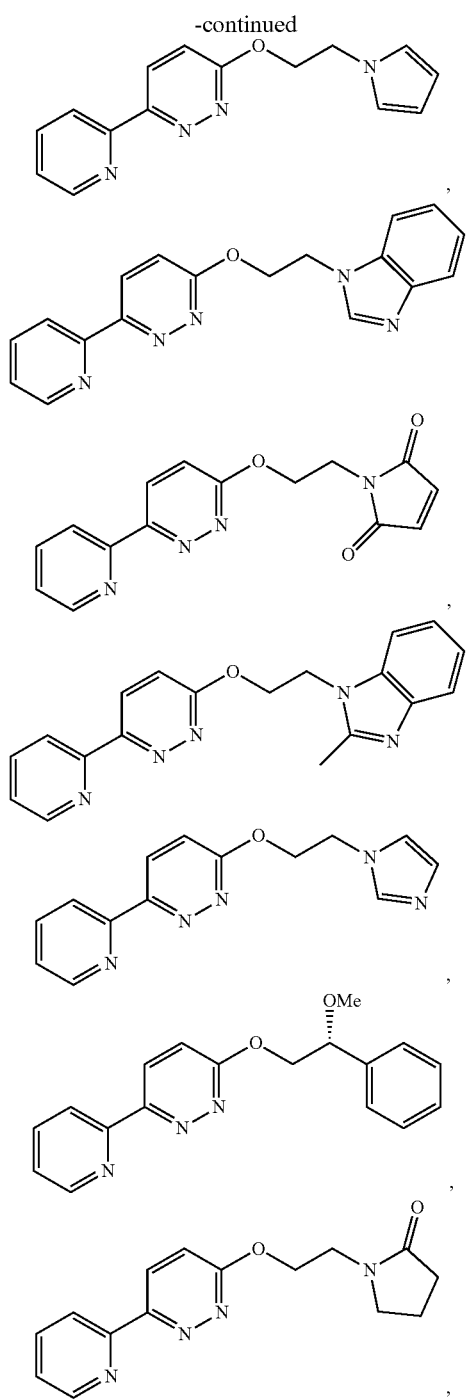
100
-continued
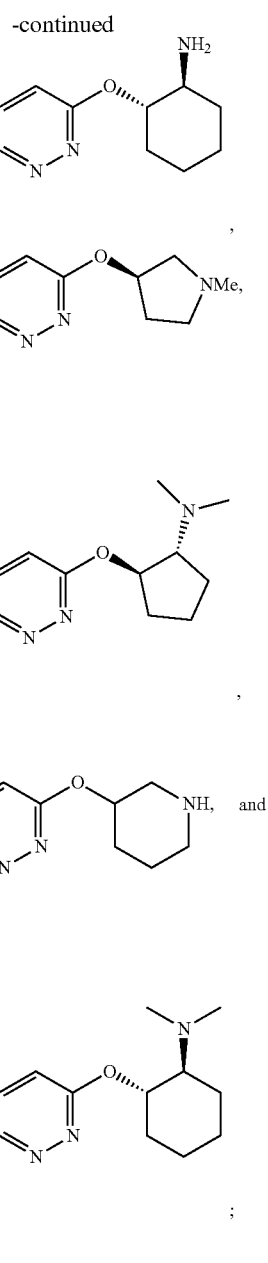
or a pharmaceutically acceptable salt thereof.
11. A pharmaceutical composition comprising a compound of claim 1 or a pharmaceutically acceptable salt thereof, and a pharmaceutically acceptable excipient.
* * * * *